US006699861B1

United States Patent
Skelton et al.

(10) Patent No.: US 6,699,861 B1
(45) Date of Patent: Mar. 2, 2004

(54) ANTI-QUINAZOLINE COMPOUNDS

(75) Inventors: Lorraine Skelton, Sutton (GB); Vassilis Bavetsias, Sutton (GB); Ann Jackman, Sutton (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 09/914,010

(22) PCT Filed: Feb. 24, 2000

(86) PCT No.: PCT/GB00/00655

§ 371 (c)(1),
(2), (4) Date: Oct. 19, 2001

(87) PCT Pub. No.: WO00/50417

PCT Pub. Date: Aug. 31, 2000

(30) Foreign Application Priority Data

Feb. 24, 1999 (GB) .............................................. 9904275

(51) Int. Cl.$^7$ ................... C07D 239/88; C07D 239/93; C07D 239/94; C07D 31/517; A61D 35/00
(52) U.S. Cl. ............................. 514/234.5; 514/252.17; 514/267; 514/266.2; 514/266.21; 514/266.22; 514/266.23; 544/116; 544/119; 544/249; 544/284
(58) Field of Search .................................. 544/116, 119, 544/249, 284; 514/234.5, 252.17, 267, 266.2, 266.21, 266.22, 266.23

(56) References Cited

FOREIGN PATENT DOCUMENTS

| EP | 0 239 362 A2 | 9/1987 |
| EP | 0 284 338 | 9/1988 |
| EP | 0 339 976 A1 | 11/1989 |
| EP | 0 373 891 A2 | 6/1990 |
| EP | 0 459 730 A2 | 12/1991 |
| EP | 0 509 643 A1 | 10/1992 |
| EP | 0 562 734 A1 | 9/1993 |
| GB | 2 065 653 | 7/1981 |
| WO | WO 94/07869 | 4/1994 |
| WO | WO 94/11354 | 5/1994 |

OTHER PUBLICATIONS

Pfleider and Rokos, ed., "Aminomethyl pyridine analogues of the quinazoline antifolate ICI 198583 with a folate–independent locus of action", Chemistry and Biology of the Pteridines and Antifolates 1997, pp. 209–212.

A novel class of lipophilic quinazoline–based folic acid analogues: "Cytotoxic agents with a folate–independent locus" British Journal of Cancer (1999) 79 (11/12), 1692–1701.

"Mechanistic studies with CB30865: A lipophilic quinazoline analogue of folic acid": Proceedings of the American Association for Cancer Research, vol. 37, Mar. 1996, pp. 394, Abstract #2691.

"Lipophilic pyridyl–quinazoline analogues of folic acid with different loci of action": British Journal of Cancer (1996) 73:28.

"Folate–based 3–pyridyl quinazolines of undefined mechanism of action as potential anti–tumour agents": Proceedings of the 9$^{th}$ NCI.EORTC Symposium on New Drugs in Cancer Therapy (1996), Abstract #307.

"Studies relating to the mechanism of action of CB30865: A lipophilic quinazoline–based analogue of folic acid": Proceedings of the American Association for Cancer Research, vol. 38, Mar. 1997, p. 48, Abstract#3200.

"Investigations into the mechanism of action of CB30865: A lipophilic quinazoline analogue of the antifolate ICI 198583": British Journal of Cancer (1997) 75 (Suppl 1) p. 5, Abstract 1.3.

"Lipophilic quinazoline analogues of folic acid with 3–pyridylamide replacing the glutamate: evidence for a non–folate locus": Proceedings of the American Association for Cancer Research, vol. 37, Mar. 1996, p. 394, Abstract 2690.

"Unusual mechanism of action of a folate–based 3–pyridyl quinazoline": Cytometry Suppl. 8, 43, 1996, Abstract CC10.

"Genomic alterations associated with acquired resistance to novel antitumor agents": Proceedings of the American Association for Cancer Research, vol. 39, Mar. 1998, p. 658, Abstract 658.

Extract from thesis from Dr. Lorraine Skelton which became open to public inspection on Aug. 28, 1999.

Skelton, Abstract entitled "Lipophilic inhibitors of thymidylate synthase: 2–pyridyl quinazolines": British Journal of Cancer 69:41 (1994). Abstract P66.

Jackman et al, Proceedings of the American Association for Cancer Research, p. 301, vol. 35, Mar. 1994, Abstract 1791.

Skelton et al, Proceedings of the American Association for Cancer Research, pp. 426 to 427, vol. 40, Mar. 1999. Abstract 2817.

(List continued on next page.)

Primary Examiner—Mark L Berch
(74) Attorney, Agent, or Firm—Nixon & Vanderhye P.C.

(57) ABSTRACT

Dihydroquinazoline derivatives of the formula (I)

where $R_3$ is —$(CH_2)_p$—A where p is from 1 to 4 and A is a 5- or 6-membered N-containing heterocyclic ring attached via the N atom or A is —NA'A" wherein A' and A" are the same or different and are each a $C_1$–$C_4$ alkyl group or their pharmaceutically acceptable salts possessing anti-cancer activity.

13 Claims, No Drawings

OTHER PUBLICATIONS

Jackman et al, CB300919, a new water-soluble quinazoline antitumour agent with activity in human tumour cell lines grown in the hollow-fibre mouse model: Clinical Cancer Research, p. 4562(s), vol. 6, Nov. 2000. Abstract 478.

Bavetsias et al, The design of water soluble analogues of CB30865, a quinazolin-4-one-based antitumour agent with an unknown mechanism of action: Clinical Cancer Research, p. 4532(s), vol. 6, Nov. 2000. Abstract 330.

Skelton et al, Cytometry 33:56-66 (1998).

ANTI-QUINAZOLINE COMPOUNDS

This invention relates to dihydroquinazoline derivatives, or pharmaceutically acceptable salts thereof, which possess anti-cancer activity. The invention includes dihydroquinazoline derivatives, processes for their manufacture, pharmaceutical compositions containing them and their use in the manufacture of a medicament for use in the treatment or prevention of cancer in a warm-blooded animal such as man.

It is known that inhibitors of enzymes which use folic acid derivatives often possess anti-cancer activity. Examples of such compounds include antimetabolites such as aminopterin and methotrexate. A newer compound of this type which showed considerable promise in clinical trials is known as CB3717 and is described in UK-B-2065653. Despite its promising activity against human breast, ovarian and liver cancer, however, CB3717 shows symptoms of toxicity in humans, particularly in relation to the liver and kidney (Cancer Treatment Reports, 1986, 70, 1335). A newer compound which possesses inhibitory activity against thymidylate synthase and which is showing promise in clinical trials is known as raltitrexed or ZD1694 (N-(5-[N-(3,4-dihydro-2-methyl-4-oxoquinazolin-6-ylmethyl)-N-methylamino]-2-thenoyl)-L-glutamic acid) and is described in EP-A-239362. The compound has been shown to possess promising activity against human breast, ovarian, colorectal and non-small cell lung cancer and against adenocarcinoma ($8^{th}$ NCI-EORTC Symposium, Amsterdam, March, 1994; Abstract Nos. 240 and 242 to 245).

Compounds of the ZD1694 and CB3717-type are believed to act as anti-tumour agents by inhibiting the enzyme thymidylate synthase, which catalyses the methylation of deoxyuridine monophosphate to produce thymidine monophosphate which is required for DNA synthesis. The anti-cancer activity of ZD1694 and CB3717 may be assessed in vitro by determining its inhibitory effect on that enzyme, and in cell cultures by its inhibitory effect on cancer cell lines such as the mouse leukaemia cell line L1210, the mouse lymphoma cell line L5178Y TK-/- and the human breast cancer cell line MCF-7.

Other compounds of the ZD1694 and CB3717-type have been described and claimed in EP-A-239362, EP-A-284338, EP-A-339976, EP-A-373891, EP-A-459730, EP-A-509643 and EP-A-562734, and in WO 93/19051, WO 94/07869 and WO 94/11354. These compounds may have their anti-cancer activity assessed by their activity against, for example, thymidylate synthase and the L1210, L5178Y TK-/- and MCF-7 cell lines.

Although inhibitors of thymidylate synthase are useful in many conditions, there is a need for anti-cancer compounds which operate by a different mechanism. Such compounds are required for treating patients with cancers refractory to standard chemotherapeutic agents. Further, it is highly desirable that anti-cancer compounds are water soluble, as increased water solubility generally enables a higher bioavailability.

4-[N-[7-bromo-2-methyl-4-oxo-3,4-dihydroquinazolin-6-ylmethyl]-N-(prop-2-ynyl)amino]-N-(3-pyridylmethyl)benzamide (CB 30865) is a known anti-cancer compound which acts via a non-folate dependent locus (Skelton et al, Cytometry 33 56–66 (1998)). However, the compound has very low water-solubility and is not suitable for in vivo administration. The compound is also still a good inhibitor of isolated thymidylate synthase and in some cell lines (resistant to the primary effects of the compound) this becomes a growth rate limiting target for CB 30865 at compound concentrations in the micromolecular range.

The present invention therefore seeks to provide new anti-cancer compounds which do not operate via inhibition of thymidylate synthase and which have an acceptable bioavailability.

Accordingly, the present invention provides a compound of formula (I), or a pharmaceutically acceptable salt thereof, (I)

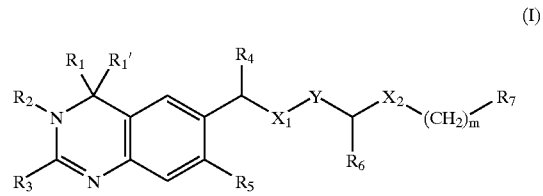

wherein:

either $R_1$ and $R_1'$ together form an oxo group and $R_2$ is hydrogen, $C_1$–$C_4$ alkyl, —($C_1$–$C_4$ alkyl)—B, —($C_1$–$C_4$ alkyl)—COB, —($C_1$–$C_4$ alkyl)—CO—($C_1$–$C_4$ alkyl)—B, —($C_1$–$C_4$ alkyl)—$CO_2$—($C_1$–$C_4$ alkyl)—B, —($C_1$–$C_4$ alkyl)—$CO_2$—($C_2$–$C_4$ alkenyl)—B or —($C_1$–$C_4$ alkyl)—CONH—($C_1$–$C_4$ alkyl)—B wherein B is —$CO_2$H, hydroxy, $C_1$–$C_4$ alkoxy, amino, ($C_1$–$C_4$ alkyl)amino, di($C_1$–$C_4$ alkyl)amino or a 5- or 6-membered heterocyclic group, or $R_1'$ and $R_2$ together form a bond and $R_1$ is —S—($C_1$–$C_4$ alkyl), —NHR' or —NHCOR' wherein R' is aryl or $C_1$–$C_4$ alkyl;

$R_3$ is —$(CH_2)_p$—A wherein p is from 1 to 4 and A is a 5- or 6-membered N-containing heterocyclic ring attached via the N atom or A is —NA'A" wherein A' and A" are the same or different and are each a $C_1$–$C_4$ alkyl group;

either $R_4$ is hydrogen, oxo or $C_1$–$C_4$ alkyl and $R_5$ is hydrogen, $C_1$–$C_4$ alkyl or halogen, or $R_4$ and $R_5$, together with the carbon atoms to which they are attached, form a 5- or 6-membered carbocyclic ring;

$X_1$ is —O—, —S— or —NR"— wherein R" is hydrogen, $C_1$–$C_4$ alkyl, $C_2$–$C_4$ alkenyl or $C_2$–$C_4$ alkynyl;

Y is a divalent aryl or heteroaryl group;

$R_6$ is hydrogen, oxo or $C_1$–$C_4$ alkyl;

$X_2$ is —O—, —S— or —NR"— wherein R" is as defined above;

m is from 1 to 4; and $R_7$ is pyridyl, pyrimidyl, imidazolyl, triazolyl, —($C_1$–$C_4$ alkyl)-imidazolyl, or —($C_1$–$C_4$ alkyl)-triazolyl.

As used herein, a $C_1$–$C_4$ alkyl group or moiety can be linear or branched but is preferably linear. Suitable such alkyl groups and moieties include methyl, ethyl, n-propyl, i-propyl, n-butyl and t-butyl. Methyl and ethyl are preferred and methyl is particularly preferred. A $C_1$–$C_4$ alkyl group or moiety can be substituted or unsubstituted at any position. Typically, it carries up to 3 substituents, e.g. one or two substituents. Suitable substituents include hydroxy, halogen, amino, ($C_1$–$C_4$ alkyl)amino and di-($C_1$–$C_4$ alkyl)amino. Preferred substituents are dimethylamino, diethylamino and halogen.

In groups which contain more than one $C_1$–$C_4$ alkyl moiety, the alkyl moieties may be the same or different. Thus, the $C_1$–$C_4$ alkyl moieties present in a di-($C_1$–$C_4$ alkyl)amino group may be the same or different.

A $C_2$–$C_4$ alkenyl group is typically an allyl group.

An aryl group or moiety is typically a $C_6$–$C_{10}$ aryl group or moiety. Suitable such aryl groups and moieties include phenyl and naphthyl. Phenyl is preferred. An aryl group or moiety may be substituted or unsubstituted at any position.

Preferably, it is unsubstituted. However, it can carry, for example, 1, 2, 3 or 4 substituents. Suitable substituents include halogen, hydroxyl, said $C_1$–$C_4$ alkyl such as methyl or ethyl, $C_1$–$C_4$ alkoxy such as methoxy or ethoxy, amino, ($C_1$–$C_4$ alkyl)amino and di-($C_1$–$C_4$ alkyl)amino. A divalent aryl moiety is preferably a 1,4-phenylene group.

p is typically 1 or 2.

A halogen is typically chlorine, fluorine, bromine or iodine. Chlorine and bromine are preferred.

A said 5- or 6-membered carbocyclic ring may be a substituted or unsubstituted, aromatic or non-aromatic 5- or 6-membered ring made up of carbon atoms. Preferably, it is a 5-membered ring. Preferably, it is saturated except for the double bond it shares with the dihydroquinazoline moiety. Preferably, it is unsubstituted. However, it may carry, for example, 1 or 2 substituents. Suitable substituents include halogen, hydroxyl, said $C_1$–$C_4$ alkyl such as methyl or ethyl, $C_1$–$C_4$ alkoxy such as methoxy or ethoxy, amino, ($C_1$–$C_4$ alkyl)amino, di-($C_1$–$C_4$ alkyl)amino and —($C_1$–$C_4$ alkyl)—OH.

A $C_2$–$C_4$ alkenyl group or moiety can be linear or branched but is preferably linear. Suitable such alkenyl groups and moieties include ethenyl, n-propenyl, i-propenyl and n-butenyl. Ethenyl and prop-2-enyl are preferred and prop-2-enyl is particularly preferred. A $C_2$–$C_4$ alkenyl group or moiety can be substituted or unsubstituted at any position. Typically, it carries up to three substituents, e.g. one or two substituents. Suitable substituents include hydroxy, halogen, amino, ($C_1$–$C_4$ alkyl)amino and di-($C_1$–$C_4$ alkyl)amino.

A $C_2$–$C_4$ alkynyl group or moiety is an ethynyl, propynyl or butynyl group or moiety. Prop-2-ynyl is preferred. A $C_2$–$C_4$ alkynyl group or moiety can be substituted or unsubstituted at any position. Typically, it carries up to two substituients, e.g. one substituent. Suitable substituents include hydroxy, halogen, amino, ($C_1$–$C_4$ alkyl)amino and di-($C_1$–$C_4$ alkyl)amino.

A divalent heteroaryl group is typically a 5- to 10-membered aryl ring containing at least one heteroatom selected from O, S and N. It may optionally be fused to a said aryl group or to a $C_3$–$C_6$ cycloalkyl group. It may be unsubsituted or substituted at any position. Typically, it carries up to three substituents, e.g. one or two substituents. Suitable substituents include halogen, hydroxyl, $CF_3$, $CCl_3$, said $C_1$–$C_4$ alkyl such as methyl or ethyl, $C_1$–$C_4$ alkoxy such as methoxy or ethoxy, amino, ($C_1$–$C_4$ alkyl)amino and di-($C_1$–$C_4$ alkyl)amino.

Preferably, the divalent heteroaryl group is a 5- or 6-membered ring. More preferably, it is a divalent pyridyl, pyrimidinyl or thiazole group. Typically, it is attached to the rest of the molecule at each position via a carbon atom.

The 5- or 6-membered heterocyclic group may be an aromatic or non-aromatic, saturated or non-saturated, substituted or non-substituted such group. It may contain one or more, for example, one, two or three heteroatoms selected from N, O and S. Typically, it carries one, two or three substituents. Suitable substituents include halogen, hydroxy, $CF_3$, $CCl_3$, —$CO_2H$, amino, ($C_1$–$C_4$ alkyl)amino and di($C_1$–$C_4$alkyl)amino.

Suitable such heterocyclic groups include morpholinyl, imidazolidinyl, pyrazolidinyl, piperidyl and piperazinyl groups. Morpholinyl, for example morpholin-4-yl groups, and piperidyl groups are preferred.

The 5- or 6-membered N-containing heterocyclic ring may be an aromatic or non-aromatic, saturated or non-saturated, substituted or non-substituted ring. It may contain one or more, for example 1 or 2, further heteroatoms selected from N, O and S.

Typically, the N-containing heterocyclic ring carries up to three substituents, e.g. one or two substituents. Suitable substituents include halogen, hydroxyl, $CF_3$, $CCl_3$, said $C_1$–$C_4$ alkyl such as methyl, ethyl and hydroxyethyl, $C_1$–$C_4$ alkoxy such as methoxy or ethoxy, phenyl, -phenyl-$CO_2H$, -phenyl-$CO_2$—($C_1$–$C_4$ alkyl), amino, ($C_1$–$C_4$ alkyl)amino, di-($C_1$–$C_4$ alkyl)amino, —$CO_2H$, —$CO_2$—($C_1$–$C_4$ alkyl) such as —$CO_2$Me and a said 5- or 6-membered heterocyclic group such as a piperidyl, pyridyl, pyrazinyl, piperazinyl or morpholinyl group. Preferably, it is unsubstituted or substituted by phenyl, hydroxy, $C_1$–$C_4$ alkyl, for example methyl, ethyl or hydroxyethyl, or —$CO_2$—($C_1$–$C_4$ alkyl).

Suitable N-containing heterocyclic rings include piperazinyl, piperidinyl, morpholinyl and pyrrolidinyl rings.

When the compound of the invention contains two groups R", the two R" groups may be the same or different.

m is typically 1 or 2.

The moieties —$(CH_2)_p$— and —$(CH_2)_m$— are alkylene groups having p and m carbon atoms respectively. The alkylene groups may be substituted or unsubstituted. Typically, they carry 1 or 2 substituents. Suitable substituents include halogen, hydroxyl, $CF_3$, $CCl_3$, said $C_1$–$C_4$ alkyl such as methyl or ethyl, $C_1$–$C_4$ alkoxy such as methoxy or ethoxy, amino, ($C_1$–$C_4$ alkyl)amino and di-($C_1$–$C_4$ alkyl) amino.

Preferably, $R_1$ and $R_1'$ together form an oxo group and $R_2$ is as defined above or $R_1'$ and $R_2$ together form a bond and $R_1$ is —$SCH_3$, —NHCOPh or —NHR' wherein R' is a $C_1$–$C_4$ alkyl group substituted by a di-($C_1$–$C_4$ alkyl) amino group, for example —NH—$CH_2$—$CH_2$—$N(CH_3)_2$. More preferably, $R_1$ and $R_1'$ together form an oxo group and $R_2$ is as defined above.

When $R_1$ and $R_1'$ together form an oxo group, $R_2$ is preferably hydrogen, $C_1$–$C_4$ alkyl, for example methyl, ethyl or dimethylaminoethyl, —($C_1$–$C_4$ alkyl)—$CO_2H$, —($C_1$–$C_4$alkyl)—$CO_2$—($C_1C_4$ alkyl), —($C_1$–$C_4$ alkyl)—CONR'R" wherein R' and R" are the same or different and are selected from hydrogen and $C_1$–$C_4$ alkyl, —($C_1$–$C_2$ alkyl)—B, —($C_1$–$C_2$ alkyl)—CO—($C_1$–$C_4$ alkyl)—B, —($C_1$–$C_2$ alkyl)—$CO_2$—($C_1$–$C_4$ alkyl)—B or —($C_1$–$C_2$ alkyl)—CONH—($C_1$–$C_4$ alkyl)—B, wherein B is as defined above, or —($C_1$–$C_2$ alkyl)—CO—B' wherein B' is a 5- or 6-membered heterocyclic group. More preferably, $R_2$ is hydrogen, $C_1$–$C_4$ alkyl such as methyl, ethyl or dimethylaminoethyl, —($C_1$–$C_4$ alkyl)—$CO_2H$, —($C_1$–$C_4$ alkyl)—$CO_2$—($C_1$–$C_4$ alkyl), —($C_1$–$C_4$ alkyl)—CONR'R" wherein R' and R" are as defined above, or —($C_1$–$C_2$ alkyl)—COB' wherein B' is as defined above. Methyl, ethyl, —$(CH_2)_2NMe_2$, —$CH_2$—$CO_2H$, —$CH_2$—$CO_2$Me, —$CH_2$—CO—$NEt_2$ and —$CH_2$—CO—N— piperidyl are particularly preferred.

Preferably, $R_3$ is —$(CH_2)_p$A wherein p is 1 or 2 and A is an optionally substituted piperidyl, piperazinyl, morpholinyl or pyrrolidinyl group or A is —$NEt_2$. Suitable substituents include those given above as appropriate substituents for the N-containing heterocyclic ring. Preferred substituents are phenyl, hydroxy, $C_1$–$C_4$ alkyl, for example methyl, ethyl or hydroxyethyl, and —$CO_2$—($C_1$–$C_4$ alkyl).

More preferably, p is 1 and A is pyrrolidin-1-yl, methyl-L-prolin-1-yl, morpholin-4-yl, piperidin-1-yl, 4-hydroxy-piperidin-1-yl, 4-phenyl-piperazin-1-yl, 4-(2-hydroxyethyl)-piperazin-1-yl, piperazin-1-yl, 4-methylpiperazin-1-yl, 4-ethylpiperazin-1-yl or $NEt_2$.

Typically, the 5- or 6-membered carbocyclic ring formed by $R_4$ and $R_5$ is a cyclopentene ring.

Preferably, $R_4$ is hydrogen.

Preferably, $R_5$ is halogen such as chlorine or bromine or is —$CX_3$ wherein X is a halogen such as fluorine.

Preferably, R" is a $C_2$–$C_4$ alkenyl group or a $C_2$–$C_4$ alkynyl group.

Preferably, $X_1$ is —NR"— wherein R" is a $C_1$–$C_4$ alkyl, $C_2$–$C_4$ alkenyl or $C_2$–$C_4$ alkynyl group. More preferably, $X_1$ is —N($CH_3$)— or —N($CH_2CCH$)—.

When $R_4$ and $R_5$ do not together form a said carbocyclic ring, the moiety —$CR_4X_1$— is typically —CON($C_1$–$C_4$ alkyl)— such as —CONMe—, —CONH—, —CH($C_1$–$C_4$ alkyl)NH— such as —CHMeNH—, —CH($C_1$–$C_4$ alkyl)N ($C_1$–$C_4$ alkyl)— such as —CHMeNMe—, —$CH_2$O—, —$CH_2$S— or, preferably, —$CH_2$N($CH_2CCH$)—. When $R_4$ and $R_5$, together with the carbon atoms to which they are attached, form a said carbocyclic ring, $X_1$ is preferably —N($C_1$–$C_4$ alkyl)—.

Preferably, Y is a phenylene or naphthylene group. More preferably, Y is a 1,4-phenylene group.

Preferably, $R_6$ is oxo.

Preferably, $X_2$ is —NH— or —N($C_1$–$C_4$ alkyl)—.

The moiety —$CR_6X_2$— is typically —$CH_2$N ($CH_2CCH$)—, —CON($C_1$–$C_4$ alkyl)— such as —CONMe—, —CH($C_1$–$C_4$ alkyl)NH— such as —CHMeNH—, —CH($C_1$–$C_4$ alkyl)N($C_1$–$C_4$ alkyl)— such as —CHMeNMe—, —$CH_2$O—, —$CH_2$S— or, preferably, —CO—NH—.

Preferably, $R_7$ is pyridyl, imidazolyl, triazolyl, —($C_1$–$C_4$ alkyl)-imidazolyl or —($C_1$–$C_4$ alkyl)-triazolyl. More preferably, $R_7$ is pyridyl, for example pyridin-3-yl, imidazolyl or triazolyl. As used herein, a triazolyl group is typically a 1,2,4-triazolyl or a 1,2,3-triazolyl group.

Preferred compounds of the invention are those in which:

either $R_1$ and $R_1$' together form an oxo group and $R_2$ is hydrogen, $C_1$–$C_4$ alkyl such as methyl, ethyl or dimethylaminoethyl, —($C_1$–$C_4$ alkyl)—$CO_2$H, —($C_1$–$C_4$ alkyl)—$CO_2$—($C_1$–$C_4$alkyl), —($C_1$–$C_4$ alkyl)—CONR'R" wherein R' and R" are as defined above, or —($C_1$–$C_2$ alkyl)—COB' wherein B' is as defined above, or $R_1$' and $R_2$ together form a bond and $R_1$ is —$SCH_3$, —NHCOPh or —NHR' wherein R' is a $C_1$–$C_4$ alkyl group substituted by a di-($C_1$–$C_4$ alkyl) amino group, for example —NH—$CH_2$—$CH_2$—N ($CH_3$)$_2$;

$R_3$ is —($CH_2$)$_p$A wherein p is 1 or 2 and A is an optionally substituted piperidyl, piperazinyl, morpholinyl or pyrrolidinyl group or A is —$NEt_2$;

$R_4$ is hydrogen;

$R_5$ is halogen such as chlorine or bromine or is —$CX_3$ wherein X is a halogen such as fluorine;

the moiety —$CR_4X_1$— is —CON($C_1$–$C_4$ alkyl)— such as —CONMe—, —CONH—, —CH($C_1$–$C_4$ alkyl)NH— such as —CHMeNH—, —CH($C_1$–$C_4$ alkyl)N($C_1$–$C_4$ alkyl)— such as —CHMeNMe—, —$CH_2$O—, —$CH_2$S— or, preferably, —$CH_2$N($CH_2CCH$)—;

Y is a phenylene or naphthylene group;

the moiety —$CR_6X_2$— is —$CH_2$N($CH_2CCH$)—, —CON ($C_1$–$C_4$ alkyl)— such as —CONMe—, —CH($C_1$–$C_4$ alkyl)NH— such as —CHMeNH—, —CH($C_1$–$C_4$ alkyl)N($C_1$–$C_4$ alkyl)— such as —CHMeNMe—, —$CH_2$O—, —$CH_2$S— or, preferably, —CO—NH—;

m is 1; and $R_7$ is pyridinyl, for example pyridin-3-yl, imidazolyl or triazolyl and pharmaceutically acceptable salts thereof Typically, in the above preferred compounds, when $R_1$ and $R_1$' together form an oxo group, $R_2$ is $C_1$–$C_4$ alkyl such as methyl. Typically, in the above preferred compounds, $R_7$ is 3-pyridyl.

Further preferred compounds of the invention are compounds of the formula (Ia) and pharmaceutically acceptable salts thereof,

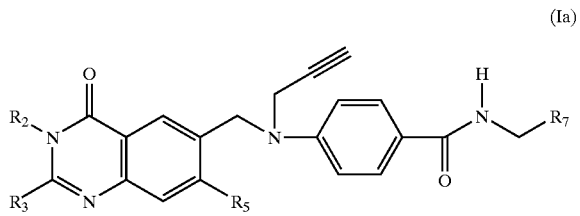

(Ia)

wherein:

$R_2$ is hydrogen, $C_1$–$C_4$ alkyl such as methyl, ethyl or dimethylarminoethyl, —($C_1$–$C_4$ alkyl)—$CO_2$H, —($C_{C4}$ alkyl)—$CO_2$—($C_1$–$C_4$ alkyl), —($C_1$–$C_4$ alkyl)—CONR'R" wherein R' and R" are as defined above, or —($C_1$–$C_2$ alkyl)—COB' wherein B' is as defined above;.

$R_3$ is —($CH_2$)$_p$—A wherein p is from 1 to 4 and A is a 5- or 6-membered N-containing heterocyclic ring or A is —NA'A" wherein A' and A" are the same or different and are both $C_1$–$C_4$ alkyl groups;

$R_5$ is chlorine or bromine; and $R_7$ is pyridyl, for example pyridin-3-yl, imidazolyl or triazolyl.

$R_2$ in the formula (Ia) can be hydrogen or $C_1$–$C_4$ alkyl. It is preferably methyl, ethyl, —($CH_2$)$_2$$NMe_2$, —$CH_2$—$CO_2$H, —$CH_2$—$CO_2$Me, —$CH_2$—CO—$NEt_2$ or —$CH_2$—CO—N-piperidinyl. $R_3$ in the formula (Ia) is preferably —($CH_2$)$_p$A wherein p is 1 or 2 and A is an optionally substituted piperidyl, piperazinyl, morpholinyl or pyrrolidinyl group or A is —$NEt_2$. More preferably, p is 1 and A is pyrrolidin-1-yl, methyl-L-prolin-1-yl, morpholin-4-yl, piperidin-1-yl, 4-hydroxy-piperidin-1-yl, 4-phenyl-piperazin-1-yl, 4-(2-hydroxyethyl)-piperazin-1-yl, piperazin-1-yl, 4-methylpiperazin-1-yl, 4-ethylpiperazin-1-yl or —$NEt_2$. $R_7$ in the formula (Ia) is preferablypyridin-3-yl.

Further preferred compounds of the invention are compounds of formula (Ib)

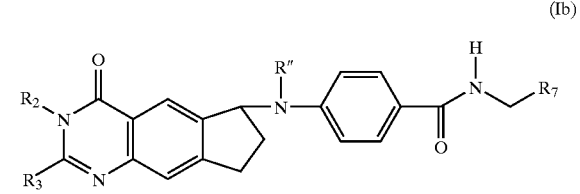

(Ib)

wherein $R_2$, $R_3$ and $R_7$ are as defined in the formula (Ia) and R" is hydrogen, $C_1$–$C_4$ alkyl, $C_2$–$C_4$ alkenyl or $C_2$–$C_4$ alkynyl. Preferably, R" in the formula (Ib) is $C_1$–$C_4$ alkyl, for example methyl.

The present invention includes pharmaceutically acceptable salts of the compounds of formula (I) and of formula (Ia). Suitable salts include salts with pharmaceutically acceptable acids, both inorganic acids such as hydrochloric, sulphuric, phosphoric, diphosphoric, hydrobromic or nitric acid and organic acids such as citric, fumaric, maleic, malic, ascorbic, succininc, tartaric, benzoic, acetic, methanesulphonic, ethanesulphonic, benzenesulphonic or p-toluenesulphonic acid. Salts may also be formed with pharmaceutically acceptable bases such as alkali metal (eg sodium or potassium) and alkali earth metal (eg calcium or magnesium) hydroxides and organic bases such as alkyl amines, aralkyl amines or heterocyclic amines. A preferred salt is the hydrochloride salt.

Some of the compounds of the invention include one or more chiral centre. The present invention includes enantiomers and diastereoisomers of such compounds. For example, the group $X_2$—$(CH_2)_m$—$R_7$ may include a chiral centre when the alkylene moiety —$(CH_2)_m$— is substituted.

Particularly preferred compounds of the invention are:

4-[N-[7-chloro-3-methyl-2-(4-methyl-piperazin-1-yl)methyl-4-oxo-3,4-dihydroquinazolin-6-ylmethyl]-N-(prop-2-ynyl)amino]-N-(3-pyridylmethyl)benzamide, 4-[N-[2-diethylaminomethyl-7-chloro-3-methyl-4-oxo-3,4-dihydroquinazolin-6-ylmethyl]-N-(prop-2-ynyl)amino]-N-(3-pyridylmethyl)benzamide, 4-[N-[7-chloro-3-methyl-4-oxo-2-(piperldin-1-yl)methyl-3,4-dihydroquinazolin-6-ylmethyl]-N-(prop-2-ynyl)amino]-N-(3-pyridylmethyl)benzamide, 4-[N-[7-chloro-3-methyl-2-(morpholin-4-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(pyrrolidin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(4-ethyl-piperazin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(methyl-L-prolin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(4-(2-hydroxyethyl)-piperazin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-4-oxo-2-(4-phenylpiperazin-1-yl)methyl-3,4-dihydroquinazolin-6-ylmethyl]-N-(prop-2-ynyl)amino]-N-(3-pyridylmethyl)benzamide, 4-[N-[7-chloro-3-methyl-2-(4-hydroxypiperidin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(4-methyl-piperazin-1-yl)methyl-4-oxo-3,4-dihydroquinazolin-6-ylmethyl]-N-(prop-2-ynyl)amino]-N-[3-(1H-imidazol-1-yl)propyl]benzamide, 4-[N-[7-chloro-3-methyl-4-oxo-2-(piperidin-1-yl)methyl-3,4-dihydroquinazolin-6-ylmethyl]-N-(prop-2-ynyl)amino]-N-[(3-(1H-1,2,4-triazol-1-yl)propyl]benzamide, 4-[N-[7-chloro-3-diethylcarbamoylmethyl-4-oxo-2-(piperidin-1-yl)methyl-3,4-dihydroquinazolin-6-ylmethyl]-N-(prop-2-ynyl)amino]-N-(3-pyridylmethyl)benzamide, 4-[N-[7-chloro-4-oxo-2-(piperidin-1-yl)methyl-3-piperidinocarbonylmethyl-3,4-dihydroquinazolin-6-ylmethyl]-N-(prop-2-ynyl)amino]-N-(3-pyridylmethyl)benzamide, 4-[N-[7-chloro-3-methoxycarbonylmethyl-4-oxo-2-piperidin-1-ylmethyl-3,4-dihydroquinazolin-6-ylmethyl]-N-(prop-2-ynyl)amino]-N-(3-pyridylmethyl)benzamide, 4-[N-[7-chloro-3-(2-dimethylaminoethyl)-4-oxo-2-piperidin-1-ylmethyl-3,4-dihydroquinazolin-6-ylmethyl]-N-(prop-2-ynyl)amino]-N-(3-pyridylmethyl)benzamide, 4-[N-[3-methyl-4-oxo-2-(piperidin-1-yl)methyl-3,4,7,8-tetrahydro-6H-cyclopenta[g]quinazolin-6-yl]-N-methylamino]-N-(3-pyridylmethyl)benzamide and pharmaceutically acceptable salts thereof.

Compounds of the invention may be prepared by reacting a compound of formula (III)

$$X_2'—(CH_2)_m—R_7 \quad\quad (III)$$

wherein m and $R_7$ are as defined above and $X_2'$ is OH, SH or $NH_2R''$ wherein R" is as defined above, with a compound of formula (IIa) or (IIb)

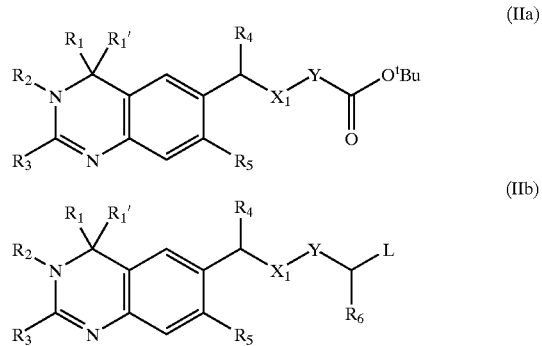

wherein $R_1$, $R_1'$, $R_2$, $R_3$, $R_4$, $R_5$, $X_1$ and Y are as defined above, $R_6$ is hydrogen or $C_1$–$C_4$ alkyl and L is a leaving group such as bromine.

The reaction between the compounds of formula (IIa) and (III) typically involves two stages. In the first stage, the tertiary butyl ester is hydrolysed. The hydrolysis is typically carried out in a solvent such as dichloromethane, in the presence of an acid such as trifluoroacetic acid at a temperature from 0° C. to the reflux temperature of the solvent. Typically, it is conducted at room temperature.

In the second stage, the compound of formula (III) is typically reacted with the hydrolysed pro duct in a dipolar aprotic solvent such as anhydrous DMF, using a coupling agent such as PyBOP®. Typically, the reaction takes place in the presence of a base such as diisopropylethylamine. Alternatively, the hydrolysed product may be converted to an acyl chloride, for example by reaction with thionyl chloride, and the compound of formula (III) may be reacted with the acyl chloride.

The leaving group L is preferably a halogen such as bromine. Typically, the reaction between the compounds of formula (IIb) and (III) takes place in a polar aprotic. solvent such as anhydrous DMF at a temperature from 0° C. to the reflux temperature of the solvent. Preferably, it is conducted in the presence of a base such as 2,6-lutidine. The reaction typically takes place under an inert atmosphere such as an argon atmosphere.

A compound of formula (IIb) may be prepared from a corresponding compound of formula (IIb) in which L is a hydrogen atom. For example, a compound of formula (IIb) in which L is a hydrogen atom can be reacted with N-bromosuccinimide in a solvent such as anhydrous carbon tetrachloride. Typically, such a reaction is conducted in the presence of an initiator such as dibenzoyl peroxide under strong illumination, The compounds of formula (III) are commercially available known compounds or may be made by analogy with known methods.

Compounds of formula (IIa) or (IIb) in which $R_1$ is —S—($C_1$–$C_4$ alkyl) can be prepared from corresponding compounds in which $R_1$ and $R_1'$ together form an oxo group and in which $R_2$ is hydrogen.

To effect the conversion, the latter compounds may be reacted with Lawesson's Reagent (2,4-bis-(4-methoxyphenyl)-1,3-dithio-2,4-diphosphetane-2,4-disulfide) in a solvent such as toluene at, for example, the reflux temperature of the solvent. The 4-oxo group can be thereby converted to a 4-thioxo group. The 4-thioxo compounds may be reacted with ($C_1$–$C_4$ alkyl)—I in the presence of a base such as $Cs_2CO_3$ in a solvent such as DMF to give compounds in which $R_1$ is —S—($C_1$–$C_4$ alkyl).

Compounds of formula (IIa) or (IIb) in which $R_1$ is —NHR' or —NHCOR' in which R' is as defined above may be prepared from corresponding compounds in which $R_1$ is —S—($C_1$–$C_4$ alkyl) by reacting the latter compounds with $H_2NR'$ or $H_2NCOR'$ wherein R' is as defined above in a solvent such as DMF at a temperature above room temperature, for example at the reflux temperature of the solvent.

The compounds of formula (IIa) and compounds of formula (IIb) in which L is a hydrogen atom can be prepared by reacting a compound of formula (IV)

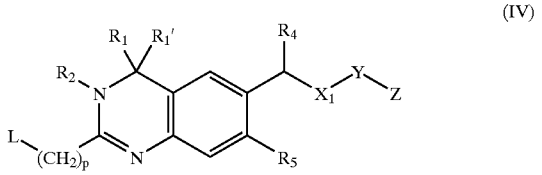

(IV)

wherein $R_1$, $R_1'$, $R_2$, p, $R_4$, $R_5$, $X_1$ and Y are as defined above, Z is —$CO_2$'Bu or —$CH_2R_6$ wherein $R_6$ is hydrogen or $C_1$–$C_4$ alkyl and L is a leaving group such as a methanesulphonyloxy group (mesylate group), a tosylate group, a triflate group or a halogen such as bromine, with a group AH wherein A is as defined above. Typically, the reaction is conducted in a solvent such as anhydrous dichloromethane under an inert atmosphere such as an argon atmosphere.

The compounds of formula (IV) can be prepared by reacting a compound of formula (V)

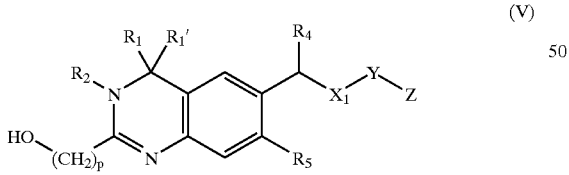

(V)

wherein $R_1$, $R_1'$, $R_2$, p, $R_4$, $R_5$, $X_1$, Y and Z are as defined above, with a reagent such as methanesulphonic anhydride, triflic anhydride, tosyl anhydride or $PX_3$ wherein X is a halogen such as bromine. Typically, the reaction takes place in a solvent such as anhydrous dichloromethane in the presence of a base such as triethylamine. Typically, the reaction takes place at below room temperature, for example at around 0° C.

The compounds of formula (V) can be made by hydrolysing an ester of formula (VI).

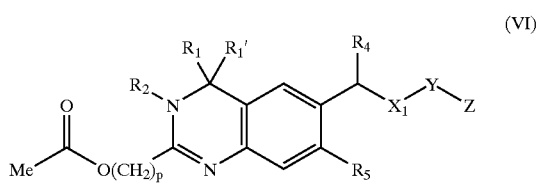

(VI)

wherein $R_1$, $R_1'$, $R_2$, p, $R_4$, $R_5$, $X_1$, Y and Z are as defined above.

Typically, the hydrolysis is effected by reaction with aqueous NaOH and water in the presence of a solvent such as tetrahydrofuran.

The esters of formula (VI) can be prepared by reacting a compound of formula (VII)

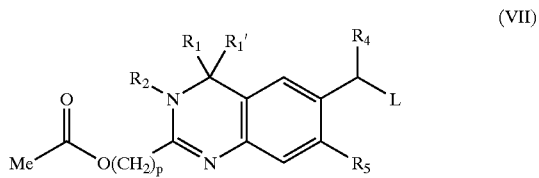

(VII)

wherein p, $R_1$, $R_1'$, $R_2$, $R_4$ and $R_5$ are as defined above and L is a leaving group such as bromine, with a compound of formula (VIII)

$X_1'$—Y—Z     (VIII)

wherein $X_1'$ is OH, SH or —NHR" wherein R" is as defined above and Y and Z are as defined above.

Typically, the reaction is carried out in a polar aprotic solvent such as anhydrous DMF at a temperature from 0° C. to the reflux temperature of the solvent. Preferably, the reaction takes place at around 120° C. Preferably, it is conducted in the presence of a base such as 2,6-lutidine. The reaction typically takes place under an inert atmosphere such as an argon atmosphere. The compound of formula (VIII) may be reacted with NaH to increase its nucleophilicity before it is reacted with the compound of formula (VII).

Compounds of formula (VI) in which $R_4$ and $R_5$ together form a carbocyclic ring and in which $X_1$ is —NR"— wherein R" is as defined above, can be prepared by reductive amination of a compound of formula (VII')

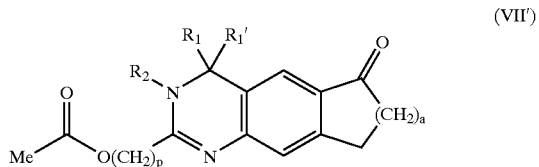

(VII')

wherein $R_1$, $R_1'$, $R_2$, and p are as defined above and a is 1 or 2. Such reductive amination can be effected by reacting a compound of formula (VII') with a said compound of formula (VIII) in which $X_1'$ is —NHR" wherein R" is as defined above. Typically, the reaction takes place in three stages.

In the first stage, a compound of formula (VII') and a compound of formula $NH_2$—Y—Z, wherein Y and Z are as defined above, are typically reacted under acidic conditions, for example in the presence of p-toluenesulphonic acid, in a solvent such as 1,2-dimethoxyethane at the reflux temperature of the solvent.

In the second stage, the thus obtained imine is typically reduced with a reducing agent such as NaCNBH$_3$ in the presence of an acid such as AcOH in a solvent such as methanol.

In the third stage, the thus obtained amine is typically reacted with an aldehyde of formula R"—COH wherein R" is as defined above, in the presence of an acid such as AcOH in a solvent such as THF, and then reduced with a reducing agent such as NaCNBH$_3$.

The compounds of formula (VII') can be prepared by oxidising a compound of formula

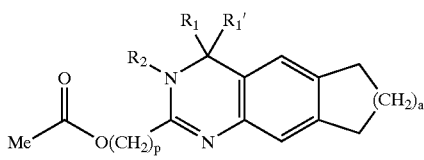

in which R$_1$, R$_1$', R$_2$, p and a are as defined above. The oxidation can be effected, for example, with a 70% t-butylhydroperoxide solution in the presence of chromium (VI) oxide in a solvent such as CH$_2$Cl$_2$.

The compounds of formula (VIII) are commercially available known compounds or may be made by analogy with known methods.

The compounds of formula (VII) in which R$_4$ is other than oxo can be prepared by reacting a corresponding compound of formula (VII) in which L is a hydrogen atom with a reagent such as N-bromosuccinimide. Typically, the reaction takes place in a solvent such as anhydrous carbon tetrachloride under an inert atmosphere such as an argon atmosphere in the presence of an initiator such as dibenzoyl peroxide and under strong illumination. The compounds of formula (VII) in which R$_4$ is oko can be prepared by reacting a corresponding compound of formula (VII) in which L is a hydroxy group with a reagent such as oxalyl chloride or thionyl chloride.

Compounds of formula (IX)

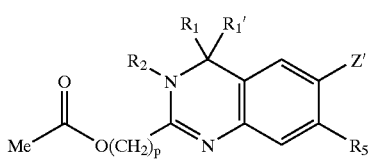

(IX)

wherein R$_1$, R$_1$', R$_2$, p and R$_5$ are as defined above and Z' is —CO$_2$H or —CH$_2$R$_4$ in which R$_4$ is other than oxo, can be prepared by reacting a compound of formula (X)

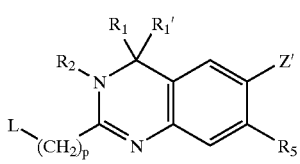

(X)

wherein R$_1$, R$_1$', R$_2$, p, R$_5$ and Z' are as defined above and L is a leaving group such as chlorine, with caesium acetate. Typically, the reaction takes place in a solvent such as anhydrous DMF under an inert atmosphere such as an argon atmosphere at a temperature of from 0° C. to the reflux temperature of the solvent, preferably around 85° C.

Compounds of formula (IX) or (X) in which R$_2$ is C$_1$-C$_4$ alkyl, —(C$_1$-C$_4$ alkyl)—COB, —(C$_1$-C$_4$ alkyl)—CO—(C$_1$-C$_4$ alkyl)—B, —(C$_1$-C$_4$ alkyl)—CO$_2$—(C$_1$-C$_4$ alkyl)—B, —(C$_1$-C$_4$ alkyl)—CO$_2$—(C$_2$-C$_4$ alkenyl)—B or —(C$_1$-C$_4$ alkyl)—CONH—(C$_1$-C$_4$ alkyl)—B wherein B is as defined above, can be prepared from a corresponding compound in which R$_2$ is hydrogen by reaction with R$_2$—I wherein R$_2$ is C$_1$-C$_4$ alkyl, —(C$_1$-C$_4$ alkyl)—COB, —(C$_1$-C$_4$ alkyl)—CO—(C$_1$-C$_4$ alkyl)—B, —(C$_1$-C$_4$ alkyl)—CO$_2$—(C$_1$-C$_4$ alkyl)—B, —(C$_1$-C$_4$ alkyl)—CO$_2$—(C$_2$-C$_4$ alkenyl)—B or —(C$_1$-C$_4$ alkyl)—CONH—((C$_1$-C$_4$ alkyl)—B wherein B is as defined above. Typically, the reaction takes place in the presence of a base such as sodium hydride under an inert atmosphere such as an argon atmosphere.

The compounds of formula (X) can be made by analogy with known methods. For example, compounds of formula (X) in which R$_1$ and R$_1$' together form an oxo group can be prepared by reacting a compound of formula (XI)

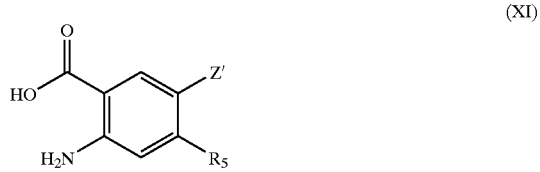

(XI)

wherein Z' and R$_5$ are as defined above, with CH$_2$ClCN (chloroacetonitrile). Typically, the reaction takes place in a solvent such as anhydrous methanol in the presence of a base such as sodium methoxide at room temperature under an inert atmosphere such as an argon atmosphere.

The substituted benzene compounds of formula (XI) can be prepared, for example, by reacting a 2-cyanoaniline compound substituted at the 4-position with Z' and at the 5-position with R$_5$, with hydrogen peroxide. The said 2-cyanoaniline compound can be prepared from a corresponding 2-bromoaniline compound by reaction with Cu(I) cyanide. The said 2-bromoaniline compound can be prepared by reacting a corresponding aniline compound unsubstituted at the 2-position with bromine in a diethyl ether/acetic acid solvent at below 5° C. under an inert atmosphere.

The compounds of the invention have anti-cancer activity. They are active against leukaemias, lymphoid malignancies and solid tumours such as carcinomas and sarcomas. They can therefore be used to treat leukaemia, breast cancer, lung cancer, livercancer, cancer of the colon, rectal cancer, stomach -cancer, prostate cancer, cancer of the bladder, pancreatic cancer and ovarian cancer.

The compounds of the present invention have a different pattern of activity to known chemotherapeutic agents. It is therefore thought that the compounds of the invention act via a new, non-folate dependent, locus. The locus at which the compounds of the invention act is thought to be different from the locii targeted by known chetnotlierapcutic agents.

The present invention includes a pharmaceutical composition comprising a compound according to the invention and a pharmaceutically acceptable carrier or diluent.

The compounds of the invention may be administered in a variety of dosage forms. Thus, they can be administered orally, for example as tablets, troches, lozenges, aqueous or oily suspensions, dispersiblepowders or granules. The compounds of the invention may also be administered parenterally, either subcutaneously, intravenously, intramuscularly, intrasternally, transdermally or by infusion techniques. The compounds may also be administered as suppositories.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginte, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of a compound of the invention is administered to a patient. A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg.

The following Examples illustrate the invention.

PREPARATION EXAMPLE 1

2-Bromo-5-chloro-4-methylaniline

To a solution of 3-chloro-4-methylaniline (10.0 g, 70.6 mmol) in diethyl ether/acetic acid (v/v 1/1, 350 ml) cooled in an ice-bath was dropwise added bromine (4 ml) over a 35 min period under an argon atmosphere while the temperature of the reaction mixture was kept below 5° C. Stirring was continued for 10 min after the addition of bromine; then the yellow reaction mixture was partitioned between dichloromethane (250 ml) and dilute brine (200 ml). The organic layer was washed with more dilute brine (200 ml), dried ($Na_2SO_4$), and concentrated in vacuo to an oily residue. This was redissolved in dichloromethane (200 ml) and the solution was washed with saturated aqueous sodium bicarbonate (3×200 ml; caution: gas is evolved), dried ($Na_2SO_4$) and concentrated in vacuo to leave a brown wet solid. Purification by column chromatography on gradient elution with dichloromethane in hexanes (25 to 30%) gave in order of elution:

a. 5-chloro-2,6-dibromo-4-methylaniline as a white solid (4.63 g) mp 77–78° C.
b. the desired product, 2-bromo-5-chloro-4-methylaniline (5.32 g, 34%), mp 90° C., $^1$H-NMR (CDCl$_3$) 2.23 (s, 3H, 4-CH$_3$), 3.99 (br s, 2H, NH$_2$), 6.78 (s, 1H, 6-H), 7.26 (s, 1H, 3-H). MS (FAB, m/z) 219, 221, 223 [(M+H)$^+$, BrCl isotopic pattern]. Elemental Analysis: Found: C, 38.04; H, 3.20; N, 6.35; Cl, 16.04; Br, 36.28. C$_7$H$_7$BrClN requires: C, 38.13; H, 3.20; N, 6.35; Cl, 16.08; Br, 36.24
c. 2-bromo-3-chloro-4-methylaniline as a white solid (1.22 g) mp 48–56° C.

PREPARATION EXAMPLE 2

4-Acetamido-2-chlorotoluene

Acetic anhydride (78 ml, 0.825 mol) was added in portions (using a dropping funnel) during a 45 min period to a stirred, cooled in an ice-bath solution of 3-chloro-4-methylaniline (106.2 g, 0.75 mol) in ethyl acetate (550 ml, dried over MgSO$_4$ prior to use) and anhydrous pyridine (66.6 ml, 0.825 mol) under argon. During the reaction the temperature of the reaction mixture varied between 10–20° C. Stirring was continued for 20 min; then the ice-water bath was removed and the reaction mixture was stirred for 18 h at room temperature. The solvents were removed in vacuo and the light brown solid residue was triturated with ether (350 ml) and left to stand in a fridge overnight. The solid was collected by filtration, washed with cold ether (100 ml) and hexanes (100 mL), dried over P$_2$O$_5$ to afford a white solid (90 g). The filtrate was concentrated in vacuo, triturated with ether to afford an additional 28.1 g of the product. Total yield 118.1 g (86%); mp 105–106° C.; $^1$H-NMR (CDCl$_3$) 2.17, 2.32 (2×s, 6H, 4-CH$_3$, CH$_3$CO), 7.14 (d, J=8.22 Hz, 1H, 6-H), 7.25 (2×dd, J=1.9, 6.5 Hz, 1H, 5-H), 7.58 (d, J=1.8 Hz, 1H, 3-H); MS (FAB, m/z) 184, 186 [(M+H)$^+$ 100%, 30% respectively; Cl isotopic pattern].

Elemental analysis: Found C, 58.76; H, 5.46; N, 7.59; Cl, 19.20. C$_9$H$_{10}$ClNO requires: C, 58.87; H, 5.49; N, 7.63; Cl, 19.30%.

PREPARATION EXAMPLE 3

4-Acetamido-5-bromo-2-chlorotoluene

To a solution of 4-acetamido-2-chlorotoluene (89.2 g, 0.486 mol) in glacial acetic acid (480 ml) that was stirred with an overhead mechanical stirrer and under argon was dropwise added bromine (28.5 ml) during a period of 2 h while the temperature of the reaction mixture was kept below 15° C. by using an ice-bath. Stirring was continued for a further 1.5 h after the addition of bromine, under an argon atmosphere. Then the brownish reaction mixture was poured into ice-water (1.8 lt), with the aid of water (1 lt), washed with water (6 lt), and dried in vacuo over P$_2$O$_5$. Purification by recrystallisation from acetonitrile afforded the desired product as a white crystals (61.5 g, 48%), mp 154–155° C.; $^1$H-NMR (CDCl$_3$) 2.24, 2.32 (2×s, 6H, 2×CH$_3$), 7.40, 7.73 (2×s, 2H, 3-H, 6-H), 7.49 (br s, 1H, CONH); MS (FAB, m/z): 262, 264, 266 [(M+H)$^+$, 80%, 100%, 25% respectively; BrCl isotopic pattern];

Elemental analysis, Found C, 41.17; H, 3.44; N, 5.36; Cl, 13.44, Br 30.60. C$_9$H$_9$BrClNO requires C, 41.17; H, 3.46; N, 5.34; Cl, 13.50; Br, 30.44.

PREPARATION EXAMPLE 4

2-Bromo-5-chloro-4-methylaniline

A solution of 4-acetamido-5-bromo-2-chlorotoluene (64 g, 0.245 mol) in glacial acetic acid (48 ml) and concentrated hydrochloric acid (96 ml) was heated at 118° C. for 24 h.

The reaction mixture was allowed to cool to room temperature, diluted with water (200 ml), cooled in an ice-bath and the pH was adjusted to 5 with a aqueous solution of NaOH (50% w/v). The precipitate was collected by filtration washed with water, and dried in vacuo over $P_2O_5$ to afford a white solid (50.7 g, 94%), mp 90° C.

PREPARATION EXAMPLE 5

2-Cyano-5-chloro-4-methylaniline

To a solution of 2-bromo-5-chloro-4-methylaniline (13.0 g 58.96 mmol) in N-methylpyrrolidinone (100 ml) was added copper(I) cyanide (10.56 g, 118 mmol). The reaction mixture was placed in an oil bath preheated to 163° C. and stirred at this temperature for 2 h. The reaction mixture was allowed to cool to room temperature and then poured in ice-water (300 ml) and aqueous ammonia (90 ml). The brown precipitate was collected by filtration, washed with water (150 ml), dissolved in dichloromethane and the insoluble material was removed by filtration. The filtrate was washed with brine (100 ml), dried ($MgSO_4$) and concentrated in vacuo. Purification, on gradient elution with dichloromethane in petroleum ether 60–80° C. (65 to 95%), afforded a white solid (6.52 g), mp 180° C.; $^1$H-NMR (DMSO-$d_6$) 2.14 (s, 3H, 4-$CH_3$), 6.11 (s, 2H, $NH_2$), 6.86 (s, 1H, 6-H), 7.39 (s, 1H, 3-H); MS (FAB, m/z) 166,168 [(M+H)$^+$; 90%, 40% respectively; Cl isotopic pattern]; FAB-HRMS: measured 166.0307; calculated for $C_8H_8ClN_2$ (M+H)$^+$ 166.0298.

PREPARATION EXAMPLE 6

2-Amino-4-chloro-5-methylbenzoic Acid

A mixture of 5-chloro-2-cyano-4-methylaniline (4.0 g, 0.024 mol), 30% aqueous KOH solution (56 ml), and 30% hydrogen peroxide (4 ml) was placed in an oil bath preheated to 130° C., then stirred at this temperature for 2 hours (a clear solution had obtained after 1.5 h). The clear solution was then allowed to cool to room temperature, diluted with water (200 ml), and acidified to pH ~5.50 with 3N HCl, then allowed to stand at room temperature for few hours. The off white solid was collected by filtration, washed with water and dried in vacuo over $P_2O_5$ (4.13 g, 93%), mp 212–215° C. $^1$H-NMR (DMSO-$d_6$) 2.16 (s, 3H, $CH_3$), 6.83, 7.62 (2×s, 2H, 3-H, 6-H), 8.50 (br s, 2H, $NH_2$); MS (FAB, m/z): 188, 186 (M+H)$^+$; FAB-HRMS: measured: 185.0256; calculated for $C_8H_8ClNO_2$ (M$^+$) 185.0244.

PREPARATION EXAMPLE 7

7-Chloro-2-chloromethyl-6-methyl-3,4-dihydroquinazolin-4-one

To a flask containing sodium (36 mg) was added anhydrous MeOH (5 ml). Chloroacetonitrile (0.520 g, 6.9 mmol) was then added and the clear solution was stirred at room temperature for 30 min under argon. A solution of 2-amino-4-chloro-5-methylbenzoic acid (1.13 g, 6.0 mmol) in anhydrous methanol (25 ml) was then added with a syringe via a rubber septum. The reaction mixture was stirred at room temperature for 2 hours under argon, then it was fitted with a condenser and placed in an oil bath preheated to 80° C. Stirring was continued at this temperature for 2 hours under argon, then the reaction mixture was allowed to cool to room temperature. The precipitate was collected by filtration, washed with methanol (10 ml), and water (10 ml), and dried in vacuo over $P_2O_5$ to afford a grey solid (1.0 g, 69%), mp 287–290° C.; $^1$H-NMR (DMSO-$d_6$) 2.47 (s, 3H, 6-$CH_3$), 4.53 (s, 2H, $CH_2Cl$), 7.75, 8.08 (2×s, 2H, 5-H and 8-H); 12.60 (s, 1H, $N^3$—H); MS (FAB, m/z) 243, 244, 245 (M+H)$^+$.

Elemental Analysis: Found: C, 49.22; H, 3.40; N, 11.39; Cl, 28.94. $C_{10}H_8Cl_2N_2O$ requires C, 49.41; H, 3.32; N, 11.52; Cl, 29.17%.

PREPARATION EXAMPLE 8

2-Acetoxymethyl-7-chloro-6-methyl-3,4-dihydroquinazolin-4-one

A mixture of 7-chloro-2-chloromethyl-6-methyl-3,4-dihydroquinazolin-4-one (0.500 g, 2.06 mmol), anhydrous DMF (14 ml) and cesium acetate (1.58 g, 8.24 mmol) was placed in an oil bath preheated to 85° C., then stirred at this temperature for 2 hours and 15 min under argon. The reaction mixture was then allowed to cool to room temperature and the solvent was removed in vacuo. The residue was treated with hexanes (20 ml), collected by filtration, washed with hexanes (20 ml), water, and dried in vacuo over $P_2O_5$ (0.476 g, 87%), mp 220–225° C., $^1$H-NMR (DMSO-$d_6$) 2.14 (s, 3H, $CH_3CO$), 2.45 (s, 3H, 6-$CH_3$), 4.95 (s, 2H, 2-$CH_2O$), 7.70, 8.06 (2×s, 2H, 5-H and 8-H), 12.44 (s, 1H, $N^3$—H).

MS (FAB, m/z) 267 (M+H)$^+$. FAB-HRMS measured 267.0520, calculated for $C_{12}H_{12}ClN_2O_3$ (M+H)$^+$ 267.0536.

PREPARATION EXAMPLE 9

2-Acetoxymethyl-7-chloro-3,6-dimethyl-3,4-dihydroquinazolin-4-one

To a suspension of 2-acetoxymethyl-7-chloro-6-methyl-3,4-dihydroquinazolin-4-one 0.428 g, 1.6 mmol) in anhydrous DMF (13 ml) was added sodium hydride (60% dispersion, 0.070 g, 1.76 mmol) under argon. Stirring was continued at room temperature for 1 min and then iodomethane (0.20 ml, 3.2 mmol) was added into the reaction mixture with a syringe via a septum. Stirring was continued at room temperature for 1 hour and the reaction mixture was then partitioned between ethyl acetate (130 ml) and brine (80 ml). The organic layer was washed with dilute brine (80 ml), dried ($Na_2SO_4$) and concentrated in vacuo to leave an orange residue. This orange residue was dissolved in dichloromethane and to this solution silica gel (Art 7734, 1.7 g) was added. The solvent was removed in vacuo and the orange free running powder was placed on a silica gel column made up in 5% ethyl acetate in dichloromethane. The column was eluted with 5% ethyl acetate in dichloromethane to afford a pale yellow solid (0.300 g, 67%), mp 110–112° C.; $^1$H-NMR (DMSO-$d_6$) 2.17 (s, 3H, $CH_3CO$), 2.47 (s, 3H, 6-$CH_3$), 3.54 (s, 3H, $N^3$—$CH_3$), 5.23 (s, 2H, 2-$CH_2O$), 7.71, 8.09 (2×s, 2H, 5-H, 8-H).

MS (FAB, m/z) 281,283 (M+H)$^+$, 100%, 25%; Cl isotopic pattern) Elemental Analysis: Found: C, 55.57; H, 4.70; N, 10.01; Cl, 12.67. $C_{13}H_{13}ClN_2O_3$ requires:C, 55.62; H, 4.67; N, 9.98; Cl, 12.63%.

PREPARATION EXAMPLE 10

2-Acetoxymethyl-6-bromomethyl-7-chloro-3-methyl-3,4-dihydroquinazoin-4-one

To a nearly clear solution of 2-acetoxymethyl-7-chloro-3,6-dimethyl-3,4-dihydroquinazolin-4-one (2.85 g, 10.16 mmol) in anhydrous carbon tetrachloride (60 ml) under argon was added N-bromosuccinimide (1.99 g, 11.17 mmol) followed by dibenzoyl peroxide (25 mg). The reaction flask was then fitted with a condenser and placed in an oil bath preheated to 85° C., and illuminated with two 60 W bulbs. Stirring was continued at this temperature for 3 hours and 50 min, then the reaction mixture was allowed to cool to room temperature. The white precipitate was filtered off, washed with dichloromethane and the filtrate was concentrated in vacuo to leave a white solid. This was partitioned between ethyl acetate (200 ml)/dichloromethanre (25 ml) and dilute brine (100 ml). The organic layer was washed with more dilute brine (100 ml), dried ($Na_2SO_4$) and concentrated in vacuo. The white solid was dissolved in dichloromethane and to this solution silica gel (Art 7734, 3.5 g) was added. The solvent was removed in vacuo and the white free running powder was placed on a silica gel column made up in 5% ethyl acetate in dichloromethane. The column was eluted with a gradient of ethyl acetate in dichloromethane (5 to 10%). Pure by TLC fractions were combined, concentrated in vacuo to leave a white solid which was triturated with ethyl acetate/hexanes (v/v 4:6, 20 ml). The white solid was collected by filtration, and dried in vacuo (1.83 g, 51%), mp 183–186° C. $^1$H-NMR (DMSO-$d_6$) 2.18 (s, 3H, $COCH_3$), 3.52 (s, 3H, $N^3$-Me), 4.92 (s, 2H, $CH_2Br$), 5.25 (s, 2H, 2-$CH_2O$), 7.78, 8.39 (2×s, 2H, 5-H, 8-H).

MS (FAB, m/z): 363,361,359 [(M+H)$^+$, 30%, 100%, 80% respectively; BrCl isotopic pattern]. Elemental analysis: Found: C, 43.62; H, 3.36; N, 7.77; Br, 9.73; Cl, 21.91. $C_{13}H_{12}BrClN_2O_3$ requires: C, 43.42; H, 3.36; N, 7.79; Br, 9.86; Cl, 22.22.

PREPARATION EXAMPLE 11 tert-Butyl 4-[N-[2-Acetoxymethyl-7-chloro-3-methyl-4-oxo-3,4-dihydroquinazolin-6-ylmethyl]-N-(prop-2-ynyl)amino]benzoate A flask containing 2-acetoxymethyl-6-bromomethyl-7-chloro-3-methyl-3,4-dihydroquinazolin-4-one (1.75 g, 4.88 mmol), anhydrous DMF (30 ml), tert-butyl 4-N-(prop-2-ynyl)aminobenzoate (1.35 g, 5.86 mmol), and 2,6-lutidine (1.38 g, 12.89 mmol) was fitted with a condenser, and placed in an oil bath preheated to 120° C., then stirred at this temperature for 5.5 hours under argon. The solvent was next removed in vacuo and the brown residue was partitioned between ethyl acetate (350 ml) and brine (120 ml). The organic layer was washed with more dilute brine (120 ml), dried ($Na_2SO_4$) and concentrated in vacuo. The brown residue was purified by column chromatography using dichloromethane:ethyl acetate: petroleumn ether 60–80° C. (v/v/v 4:3:3) as eluant. Fractions pure by TLC and not positive to Epstein's spray were combined, concentrated in vacuo to give 1.48 g of the desired product as a white solid. Fractions positive to the Epstein's spray (contaminated with a small amount of bromide) were combined, concentrated in vacuo, and the residue was triturated with hexanes/ethyl acetate (v/v, 7:3, ~10 ml), and dried in vacuo over $P_2O_5$ to afford an additional 0.340 g of the product (total yield: 1.82 g, 73%), mp 165–167° C.; $^1$H-NMR (DMSO-$d_6$) 1.50 (s,9H, Bu$^t$), 2.17 (s, 3H, $CH_3CO$), 3.46 (s, 3H, $N^3$-Me), 4.39 (s, 2H, $CH_2C\equiv C$), 4.80 (s, 2H, 6-$CH_2$), 5.22 (s, 2H, 2-$CH_2$), 6.79 (d, J=8.7 Hz, 2H, 3',5'-ArH), 7.73 (d, J=8.5 Hz, 2H, 2',6'-ArH), 7.79, 7.91 (2×s, 5-H, 8-H); MS (FAB, m/z) 509, 511 [M$^+$, 70%, 30% respectively, Cl isotopic pattern].

Elemental Analysis: Found C, 63.06; H, 5.58; N, 8.13; Cl, 7.08. $C_{27}H_{28}ClN_3O_5$ 0.25 $H_2O$ requires: C, 63.03; H, 5.58; N, 8.17; Cl, 6.81%.

PREPARATION EXAMPLE 12 tert-Butyl 4-[N-[7-Chloro-2-hydroxymethyl-3-methyl-4-oxo-3,4-dihydroquinazolin-6-ylmethyl]-N-(prop-2-ynyl)amino]benzoate To a solution of tert-butyl 4-[N-[2-acetoxymethyl-7-chloro-3-methyl-4-oxo-3,4-dihydroquinazolin-6-ylmethyl]-N-(prop-2-ynyl)amino]benzoate (0.47 g, 0.92 mmol) in tetrahydrofuran (18 ml), was slowly added 1N aqueous NaOH (1.84 ml, 1.84 mmol) followed by water (1.5 ml). The slightly cloudy solution was stirred at room temperature for 1 hour, the solvent was removed in vacuo and the residue was treated with water (35 ml). The pH was adjusted to 4.5 with 1N HCl and the mixture was extracted with ethyl acetate (3×60 ml). The organics were combined, dried ($Na_2SO_4$), and concentrated in vacuo. Purification by column chromatography, on elution with 50% ethyl acetate in dichloromethane, afforded a white solid which was reprecipitated from dichioromethane (minimum amount)/ hexanes. The solid was collected by filtration and dried in vacuo over $P_2O_5$ (0.345 g, 80%), mp 109–111° C.; $^1$H-NMR (DMSO-$d_6$); 1.49 (s, 9H, $CO_2Bu^t$), 3.50 (s, 3H, $N^3$-Me), 3.25 (s (poorly resolved triplet), 1H, C≡CH), 4.40 (s, 2H, $CH_2C\equiv C$), 4.57 (d, J=5.70 Hz, 2H, 2-$CH_2OH$), 4.80 (s, 2H, 6-$CH_2$), 5.67 (t, J=6.4 Hz, 1H, $CH_2OH$), 6.78 (d, J=8.80 Hz, 2H, 3',5'-ArH), 7.72 (d, J=8.44 Hz, 2H, 2',6'-Ar), 7.82, 7.87 (2×s, 2H, 5-H, 8-H); MS (FAB, m/z) 467, 469 (M$^+$, 95%, 45% respectively; Cl isotopic pattern).

Elemental Analysis: Found: C, 64.44; H, 5.97; N, 8.69; Cl, 7.38. $C_{25}H_{26}ClN_3O_4$ requires: C, 64.17; H, 5.60; N, 8.98; Cl, 7.58%.

PREPARATION EXAMPLE 13 tert-Butyl 4-[N-[7-Chloro-2-methanesulphonyloxymethyl-3-methyl-4-oxo-3,4-dihydroquinazolin-6-ylmethyl]-N-(prop-2-ynyl) amino]benzoate To a stirred under argon solution of tert-butyl 4-[N-[7-chloro-2-hydroxymethyl-3-methyl-4-oxo-3,4-dihydroquinazolin-6-ylmethyl]-N-(prop-2-ynyl)amino] benzoate (0.200 g, 0.43 mmol) in anhydrous dichloromethane (5 ml) cooled in an ice-bath was added triethylamine (0.152 g, 1.5 mmol) followed by methanesulphonic anhydride (0.120 g, 0.69 mmol) (added in one portion). After 10 min the ice-bath was removed and stirring was continued for 45 min-TLC (40% ethyl acetate in dichloromethane) indicated a complete reaction. The reaction mixture was then diluted with ethyl acetate (200 ml) and the solution was washed with saturated aqueous sodium bicarbonate (2×50 ml), and brine (50 ml), dried ($Na_2SO_4$) and concentrated in vacuo. Purification by column chromatography, on elution with 40% ethyl acetate in dichloromethane afforded a white solid which dried in vacuo over $P_2O_5$ (0.221 g, 94%), mp 204–205° C. $^1$H-NMR (DMSO-$d_6$): 1.50 (s, 9H, $CO_2Bu^t$), 3.17 (s (poorly resolved triplet), 1H, C≡CH), 3.20 (s, 3H, $SO_2Me$), 3.49 (s, 3H, $N^3$-Me), 4.39 (d, J=2.2 Hz, 2H, $CH_2C\equiv C$), 4.82 (s, 2H, 6-$CH_2$), 5.41 (s, 2H, 2-$CH_2$), 6.79 (d, J=8.9 Hz, 2H, 3',5'-ArH), 7.73 (d, J=8.9 Hz, 2H, 2',6'-ArH), 7.88, 7.94 (2×s, 2H, 5-H, 8-H); MS (FAB, m/z) 546, 548 [(M+H)$^+$, 95%, 44% respectively; Cl isotopic pattern].

Elemental Analysis: Found: C, 56.93; H, 5.12; N, 7.50. $C_{26}H_{28}ClN_3O_6S$_requires: C, 57.19; H, 5.17; N, 7.70%.

PREPARATION EXAMPLE 14 tert-Butyl 4-[N-[7-Chloro-3-methyl-2-(4-methyl-piperazin-1-yl)methyl-4-oxo-3,4-dihydroquinazolin-6-ylmethyl]-N-(prop-2-ynyl)amino]enzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino]

benzoate (0.205 g, 0.38 mmol) in anhydrous dichloromethane (8 ml) under argon was slowly added 1-methylpiperazine (0.376 g, 3.76 mmol). Stirring was continued for 2.5 h at room temperature under argon, then the reaction mixture was diluted with ethyl acetate (200 ml) and washed with 6% $Na_2CO_3$ (w/v solution, 2×100 ml), and dilute brine (100 ml), dried ($Na_2SO_4$) and concentrated in vacuo. Purification by column chromatography, on elution with 5% methanol in dichloromethane, afforded a white solid (0.159 g, 77%), mp 136–138° C. $^1$H-NMR (DMSO-$d_6$) 1.50 (s, 9H, Bu$^t$), 2.14 (s, 3H, N-Me piperazine), 2.29 (br s) and 2.50 (brs obscured) (8H, N(CH$_2$CH$_2$)$_2$), 3.60 (s, 3H, N$^3$-Me),3.62 (s, 2H, 2-CH$_2$), 4.38 (d, J=1.1 Hz, 2H, CH$_2$C≡C), 4.80 (s, 2H, 6-CH$_2$), 6.79 (d, J=8.9 Hz, 2H, 3',5'-ArH), 7.73 (d, J=8.9 Hz, 2',6'-ArH), 7.91, 7.79 (2×s, 2H, 5-H, 8-H).

MS (FAB, m/z) 550, 552 [(M+H)$^+$, 100%, 35% respectively, Cl isotopic pattern]. Elemental Analysis: Found: C, 65.18; H, 6.58; N, 12.60; Cl, 6.43. $C_{30}H_{36}ClN_5O_3$ requires: C, 65.50; H, 6.60; N, 12.73; Cl, 6.44%.

PREPARATION EXAMPLE 15 tert-Butyl 4-[N-[2-Diethylaminomethyl-7-chloro-3-methyl-4-oxo-3,4-dihydroquinazolin-6-ylmethyl]-N-(prop-2-ynyl)amino]benzoate To a stirred under argon solution of tert-butyl 4-[N-[7-chloro-2-methanesulphonyloxymethyl-3-methyl-4-oxo-3,4-dihydroquinazolin-6-ylmethyl]-N-(prop-2-ynyl)amino] benzoate (0.230 g, 0.42 mmol) in anhydrous dichloromethane (10 ml) was added diethyl amine (0.306 g, 4.2 mmol). The yellow solution was then stirred at room temperature for 18 hours. The solution was then diluted with ethyl acetate (250 ml) and washed with 5% aqueous sodium carbonate solution (2×100 ml), brine (100 ml), and concentrated in vacuo. Purification by column chromatography, on gradient elution with methanol in dichloromethane (0 to 2%) afforded a white crispy solid which was triturated diethyl ether/hexanes (v/v, 1:2). The white solid was collected by filtration, washed with hexanes and dried in vacuo over $P_2O_5$ (0.202 g, 92%), mp 112–113° C.; $^1$H-NMR (DMSO-$d_6$) 0.95 (t, J=6.9 Hz, 6H, 2×CH$_2$CH$_3$), 1.49 (s, 9H, Bu$^t$), 2.56 (q obscured, J=6.85 Hz, 4H, 2×CH$_2$CH$_3$), 3.62 (s, 3H, N$^3$-Me), 3.70 (s, 2H, 2-CH$_2$), 4.40 (s, 2H, CH$_2$C≡C), 4.79 (s, 2H, 6-CH$_2$), 6.78 (d, J=8.9 Hz, 2H, 3',5'-ArH), 7.72 (d, J=8.9 Hz, 2',6'-ArH), 7.81, 7.86 (2×s, 2H, 5-H, 8-H); MS (FAB, m/z) 523, 525 [(M+H)$^+$, 100%, 40% respectively; Cl isotopic pattern].

Elemental Analysis; Found: C, 65.75; H, 6.67; N, 10.45; Cl, 6.75. $C_{29}H_{35}ClN_4O_3$ 0.25 $H_2O$ requires: C, 66.02; H, 6.78; N, 10.61; Cl, 6.72%.

PREPARATION EXAMPLE 16 tert-Butyl 4-[N-[7-Chloro-3-methyl-4-oxo-2-(piperidin-1-yl)methyl-3,4-dihydroquinazolin-6-ylmethyl]-N-(prop-2-ynyl)amino]benzoate To a solution of tert-butyl 4-[N-[7-chloro-2-methanesulphonyloxymethyl-3-methyl-4-oxo-3,4-dlhydrbquinazolin-6-ylmethyl]-N-(prop-2-ynyl)amino] benzoate (0.177 g, 0.32 mmol) in anhydrous dichloromethane (7 ml) under argon was added piperidine (0.272 g, 3.2 mmol). The orange solution was stirred at room temperature for 18 hours, then partitioned between ethyl acetate (200 ml) and 5% aqueous sodium carbonate solution (80 ml). The organic layer was washed with 5% aqueous sodium carbonate (80 ml), and dilute brine (80 ml), dried ($Na_2SO_4$) and concentrated in vacuo. Purification by column chromatography on gradient elution with ethyl acetate in dichloromethane (5 to 13%) afforded a white solid which was triturated with 5% dichloromethane in hexanes, collected by filtration, washed with hexanes, and dried in vacuo over $P_2O_5$ (0.129 g, 75%), mp 162–163° C.; $^1$H-NMR (DMSO-$d_6$) 1.50 (s, 9H, Bu$^t$), 1.42, (br s obscured) and 2.42 (br s) (10H, piperidine 5×CH$_2$), 3.57 (s, 2H, 2-CH$_2$), 3.61 (s, 3H, N$^3$-Me), 3.20 (s(poorly resolved triplet), 1H, C≡CH), 4.38 (d, J=2.0 Hz, 2H, CH$_2$C≡C), 4.79 (s, 2H, 6-CH$_2$), 6.79 (d, J=9.0 Hz, 2H, 3',5'-ArH), 7.73 (d, J=8.9 Hz, 2',6'-ArH), 7.80, 7.89 (2×S, 2H, 5-H, 8-H); MS (ESI, m/z) 535, 537 [(M+H)$^+$, 100%, 38% respectively; Cl isotopic pattern].

Elemental Analysis: Found: C, 66.92; H, 6.57; N, 10.40; Cl, 6.78. $C_{30}H_{35}ClN_4O_3$ requires: C, 67.34; H, 6.59; N, 10.47; Cl, 6.63%.

PREPARATION EXAMPLE 17 tert-Butyl 4-[N-[7-Chloro-3-methyl-2-morpholinomethyl-4-oxo-3,4-dihydroquinazolin-6-ylmethyl]-N-(prop-2-ynyl)amino]benzoate A mixture of tert-butyl 4-[N-[7-chloro-2-methanesulphonyloxymethyl-3-methyl-4-oxo-3,4-dihydroquinazolin-6-ylmethyl]-N-(prop-2-ynyl )amino] benzoate (0.193 g, 0.35 mmol), dichloromethane (7 ml), and morpholine (0.304 g, 3.5 mmol) was stirred at room temperature for 6 h under argon. The cloudy reaction mixture was then partitioned between ethyl acetate (200 ml) and 5% aqueous sodium carbonate (80 ml). The organic layer was washed more 5% sodium carbonate (2×80 ml), and brine (80 ml), dried ($Na_2SO_4$) and concentrated in vacuo. Purification by column chromatography, on elution with 10% ethyl acetate in dichloromethane, afforded a solid which was triturated with 5% dichloromethane in hexanes. The white solid was collected by filtration, dried in vacuo over $P_2O_5$ (0.174 g, 82%), mp 140–143° C.; $^1$H-NMR (DMSO-$d_6$) 1.50 (s, 9H, Bu$^t$), 2.48, (br s obscured) and 3.55 (br s) (8H, N(CH$_2$CH$_2$)$_2$O), 3.62 (s, 5H, 2-CH$_2$, N$^3$-Me), 3.20 (s(poorly resolved triplet), 1H, C≡CH), 4.39 (s, 2H, CH$_2$C≡C), 4.79 (s, 2H, 6-CH$_2$), 6.78 (d, J=8.7 Hz, 2H, 3',5'-ArH), 7.72 (d, J=8.7 Hz, 2H, 2',6'-ArH), 7.80, 7.89 (2×s, 2H, 5-H, 8-H). MS (ESI, m/z) 537, 539 [(M+H)$^+$, 100%, 38% respectively; Cl isotopic pattern].

Elemental analysis: Found: C, 64.81; H, 6.30; N, 10.27; Cl, 6.79. $C_{29}H_{33}N_4ClO_4$ requires: C, 64.86; H, 6.19; N, 10.43; Cl, 6.60%.

PREPARATION EXAMPLE 18 tert-Butyl 4-[N-[7-Chloro-3-methyl-2-pyrrolidinomethyl-4-oxo-3,4-dihydroquinazolin-6-ylmethyl]-N-(prop-2-ynyl)amino]benzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino] benzoate (0.213 g, 0.39 mmol) in anhydrous dichloromethane (8 ml) was added pyrrolidine (0.277 g, 3.9 mmol). The clear solution was stirred at room temperature for 4 hours under argon. The clear solution was then partitioned between ethyl acetate (200 ml) and 5% aqueous sodium carbonate. The organic layer was washed with 5% aqueous sodium carbonate (80 ml), and brine (80 ml), dried ($Na_2SO_4$), and concentrated in vacuo. The residue was purified by column chromatography on elution with a gradient of ethyl acetate in dichloromethane (20 to 40%). The crispy solid was dissolved in dichloromethane and hexanes and the solvents were removed in vacuo to leave a white solid (0.149 g, 74%), mp 180–183° C. $^1$H-NMR (DMSO-$d_6$) 1.50 (s, 9H, Bu$^t$), 1.70, (br s, 4H, pyrrolidine CH$_2$CH$_2$), 2.54 (br s, 4H, pyrrolidine 2×N—CH$_2$), 3.60 (s, 3H, N$^3$-Me), 3.74 (s, 2H, 2-CH$_2$), 4.38 (s, 2H, CH$_2$C≡C), 4.79 (s, 2H, 6-CH$_2$), 6.79 (d, J=8.7 Hz, 2H, 3',5'-ArH), 7.73 (d, J=8.1 Hz, 2H, 2',6'-ArH), 7.79, 7.89 (2×s, 2H, 5-H, 8-H).

MS (FAB, m/z) 521, 523 [(M+H)$^+$, 55%, 20% respectively; Cl isotopic pattern]. Elemental Analysis: Found C, 66.60; H, 6.40; N, 10.68; Cl, 7.00. $C_{29}H_{33}ClN_4O_3$ requires: C, 66.85; H, 6.38; N, 10.75; Cl, 6.80.

PREPARATION EXAMPLE 19 tert-Butyl 4-[N-[7-Chloro-3-methyl-2-(4-ethyl-piperazin-1-yl)methyl-4-oxo-3,4-dihydroquinazolin-6-ylmethyl]-N-(prop-2-ynyl)amino]benzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino] benzoate (0.120 g, 0.22 mmol) in anhydrous dichloromethane (5 ml) under argon was slowly added 1-ethylpiperazine (0.246 g, 2.2 mmol). Stirring was continued for 3 h at room temperature under argon, then the reaction mixture was diluted with ethyl acetate (200 ml) and washed with 5% Na$_2$CO$_3$ (w/v solution, 2×100 ml), and dilute brine (100 ml), dried (Na$_2$SO$_4$) and concentrated in vacuo. Purification by column chromatography, on elution with 5% methanol in dichloromethane, afforded a white solid (0.086 g, 70%), mp 145–146° C. $^1$H-NMR (DMSO-$d_6$) 0.96 (t, J=6.8 Hz, 3H, CH$_2$CH$_3$), 1.49 (s, 9H, Bu$^t$), 2.29 (q obscured, J=7.2 Hz, 2H, CH$_2$CH$_3$), 2.32 (br s) and 2.48 (brs obscured) (8H, N(CH$_2$CH$_2$)$_2$), 3.29 (s, 1H, C≡CH), 3.60 (s, 5H, N$^3$-Me, 2-CH$_2$), 4.39 (s, 2H, CH$_2$C≡C), 4.80 (s, 2H, 6-CH$_2$), 6.78 (d, J=8.3 Hz, 2H, 3',5'-ArH), 7.72 (d, J=8.1 Hz, 2',6'-ArH), 7.81, 7.87 (2×s, 2H, 5-H, 8-H).

MS (ESI, m/z) 564, 566 [(M+H)$^+$, 100%, 40% respectively, Cl isotopic pattern]. Elemental Analysis: Found: C, 65.05; H, 6.73; N, 12.12; Cl, 6.12. $C_{31}H_{38}ClN_5O_3$ 0.5H$_2$O requires: C, 64.97; H, 6.86; N, 12.22; Cl, 6.19%.

PREPARATION EXAMPLE 20 tert-Butyl 4-[N-[7-Chloro-3-methyl-2-(methyl-L-prolin-1-yl)methyl-4-oxo-3,4-dihydroquinazolin-6-ylmethyl]-N-(prop-2-ynyl)amino]benzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino] benzoate (0.150 g, 0.27 mmol) in anhydrous dichloromethaiic (10 ml) under argon was added L-proline methyl ester hydrochloride(0.447 g, 2.70 mmol) followed by triethylamine (0.420 ml, 2.70 mmol). Stirring was continued for 16 h at room temperature under argon, then the reaction mixture was diluted with ethyl acetate (300 ml) and washed with saturated aqueous NaHCO$_3$ solution (2×100 ml). The aqueous phase was back extracted with ethylacetate (2×30 ml) and the combined organic phase was washed with brine (50 ml), dried (MgSO$_4$) and concentrated in vacuo. Purification by gradient column chromatography, on elution with 0% to 3% methanol in chloroform, afforded a light yellow solid, which was washed with hexanes (2×20 ml), the solid removed by filtration and dried in vacuo to afford a white solid (0.132 g, 84%), mp 69–70° C. $^1$H-NMR (DMSO-$d_6$) 1.49 (s, 9H, Bu$^t$), 1.76 (m, 3H, proline N—CH$_2$—CH$_2$CH), 2.12 (m, 1H, proline N—CH$_2$CH$_2$—CH), 2.49 (m, 1H, (obscured by DMSO), proline-CH, 2.98 (m, 1H, proline-CH), 3.25 (s, 1H, HC≡C), 3.31 (m, 1H, (obscured by H$_2$O), proline N—CHCOOCH$_3$), 3.37 (s, 3H, COOCH$_3$), 3.61 (s, 3H, N$^3$-Me), 3.85 (AB system, J=13.2 Hz, 2H, 2-CH$_2$), 4.40 (s, 2H, CH$_2$C≡C), 4.79 (s, 2H, 6-CH$_2$), 6.77 (d, J=8.9 Hz, 2H, 3',5'-ArH), 7.71 (d, J=8.9 Hz, 2H, 2',6'-ArH), 7.78, 7.87 (2×s, 2H, 5-H, 8-H).

MS (FAB, m/z) 579, 561, [(M+H)$^+$, 50%, 20% respectively, Cl isotopic pattern]. FAB-HRMS; measured 579.2360; calculated for $C_{31}H_{36}ClN_4O_5$ (M+H)$^+$: 579.2374.

PREPARATION EXAMPLE 21 tert-Butyl 4-[N-[7-Chloro-3-methyl-2-(4-(2-hydroxyethyl)piperazin-1-yl)methyl-4-oxo-3,4-dihydroquinazolin-6-ylmethyl]-N-(prop-2-ynyl) amino]benzoate To a solution of tert-butyl 4-[N-[7-chloro-2-methanesulphonyloxymethyl-3-methyl-4-oxo-3,4-dihydrquinazolin-6-ylmethyl]-N-(prop-2-ynyl)amino] benzoate (0.220 g, 0.4 mmol) in anhydrous dichloromethane (4 ml) under argon was added a solution of 1-(2-hydroxyethyl)piperazine (0.520 g, 4.0 mmol) in anhydrous dichloromethane (4 ml). Stirring was continued for 5.5 h at room temperature under argon, then the reaction mixture was diluted with ethyl acetate (200 ml) and washed with 5% aqueous sodium carbonate (w/v solution, 2×100 ml), and dilute brine (100 ml), dried (Na$_2$SO$_4$) and concentrated in vacuo. Purification by column chromatography, on elution with a gradient of methanol in dichloromethane (5 to 10%), afforded a white solid (0.210 g, 90%), mp>90° C. (softens). $^1$H-NMR (DMSO-$d_6$) 1.49 (s, 9H, Bu$^t$), 2.35 (t(obscured), J=6.4 Hz, 2H, N—CH$_2$CH$_2$OH), 2.37, 2.45 (obscured by DMSO peak), (2×br s, (8H, N(CH$_2$CH$_2$)$_2$), 3.21 (s, 1H, C≡CH), 3.46 (q, J=6.11 Hz, 2H, N—CH$_2$CH$_2$OH), 3.60 (s, 5H, N$^3$-Me, 2-CH$_2$), 4.29 (t, J=5.34 Hz, 1H, N—CH$_2$CH$_2$OH), 4.39 (s, 2H, CH$_2$C≡C), 4.80 (s, 2H, 6-CH$_2$), 6.78 (d, J=8.3 Hz, 2H, 3',5'-ArH), 7.73 (d, J=8.9 Hz, 2',6'-ArH), 7.81, 7.89 (2×s, 2H, 5-H, 8-H).

MS (ESI, m/z) 580, 582 [(M+H)$^+$, 100%, 35% respectively, Cl isotopic pattern].

PREPARATION EXAMPLE 22 tert-Butyl 4-[N-[7-Chloro-3-methyl-4-oxo-2-(4-phenylpiperazin-1-yl)methyl-3,4-dihydroquinazolin-6-ylmethyl]-N-(prop-2-ynyl)amino]benzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino] benzoate (0.197 g, 0.36 mmol) in anhydrous dichloromethane (8 ml) under argon was added 1-phenylpiperazine (0.583 g, 3.6 mmol). Stirring was continued for 2.5 h at room temperature under argon, then the reaction mixture was diluted with ethyl acetate (200 ml) and washed with 5% aqueous sodium carbonate (w/v solution, 2×100 ml), and dilute brine (100 ml), dried (Na$_2$SO$_4$) and concentrated in vacuo. Purification by column chromatography, on elution with 10% ethyl acetate in dichloromethane, afforded a white solid (0.181 g, 82%), mp>95° C. $^1$H-NMR (DMSO-$d_6$) 1.50 (s, 9H, Bu$^t$), 2.63 (br s) and 3.12 (br s) (8H, N(CH$_2$CH$_2$)$_2$), 3.21 (s, 1H, C≡CH), 3.64 (s, 3H, N$^3$-Me), 3.70 (s, 2H, 2-CH$_2$), 4.40 (s, 2H, CH$_2$C≡C), 4.81 (s, 2H, 6-CH$_2$), 6.79 (d, J=8.9 Hz, 2H, 3',5'-ArH), 6.90 (d, J=8.5 Hz, 2H), 7.20 (t, J=7.8 Hz, 2H), 6.77 (t (obscured), $C_6H_5$—N($CH_2CH_2$)$_2$N—), 7.73 (d, J=8.8 Hz, 2H, 2',6'-ArH), 7.82, 7.90 (2×s, 2H, 5-H, 8-H).

MS (ESI, m/z) 612, 614 [(M+H)$^+$, 100%, 40% respectively, Cl isotopic pattern]. Elemental Analysis: Found: C, 68.25; H, 6.28; N, 11.26; Cl, 5.89. $C_{35}H_{38}ClN_5O_3$ requires: C, 68.67; H, 6.26; N, 11.44; Cl, 5.79%.

PREPARATION EXAMPLE 23 tert-Butyl 4-[N-[7-Chloro-3-methyl-2-(4-hydroxypiperidin-1-yl)methyl-4-oxo-3,4-dihydroquinazolin-6-ylmethyl]-N-(prop-2-ynyl) amino]benzoate To a solution of tert-butyl 4-[N-[7-chloro-2-methanesulphonyloxymethyl-3-methyl-4-oxo-3,4-dihydroquinazolin-6-ylmethyl]-N-(prop-2-ynyl)amino]benzoate (0.230 g, 0.42 mmol) in anhydrous dichloromethane (4 ml) under argon was added a solution of 4-hydroxypiperidine (0.424 g, 4.2 mmol) in anhydrous $CH_2Cl_2$ (4 ml). The clear solution was stirred at room temperature for 1.5 hours under argon, then partitioned between ethyl acetate (200 ml) and 5% aqueous sodium carbonate solution (100 ml). The organic layer was washed with 5% aqueous sodium carbonate (100 ml), and dilute brine (100 ml), dried ($Na_2SO_4$) and concentrated in vacuo. The residue was triturated with ether to give a white precipitate, which was collected by filtration, washed with ether and dried in vacuo over $P_2O_5$ (0.206 g, 89%), mp 208–210° C.; $^1$H-NMR (DMSO-d$_6$) 1.50 (s, 9H, Bu$^t$), 1.33 (m, 2H), 1.65 (m, 2H), 2.17 (m, 2H), 2.72 (m, 2H), and 3.50 (m, 1H), (piperidine ring protons), 3.24 (s, 1H, C≡CH), 3.57, 3.60 (2×s, 5H, N$^3$-Me , 2-CH$_2$), 4.39 (s, 2H, CH$_2$C≡C), 4.55 (d, J=4.1 Hz, 1H, OH), 4.79 (s, 2H, 6-CH$_2$), 6.78 (d, J=8.9 Hz, 2H, 3',5'-ArH), 7.72 (d, J=8.9 Hz, 2',6'-ArH), 7.81, 7.87 (2×s, 2H, 5-H, 8-H); MS (ESI, m/z) 551, 553 [(M+H)$^+$, 100%, 37% respectively; Cl isotopic pattern].

Elemental Analysis: Found: C, 62.39; H, 6.27; N, 9.41. $C_{30}H_{35}ClN_4O_4$ 1.5$H_2O$ requires: C, 62.33; H, 6.62; N, 9.69%.

PREPARATION EXAMPLE 24

2-Acetoxymethyl-6-bromomethyl-7-chloro-3,4-dihydroquinazolin-4-one

To a suspension of 2-acetoxymethyl-7-chloro-6-methyl-3,4-dihydroquinazolin-4-one (2.00 g, 7.5 mmol) in anhydrous carbon tetrachloride (120 ml) was added N-bromosuccinimide (1.47 g, 8.3 mmol) followed by dibenzoyl peroxide (7.0 mg) under argon. The reaction mixture was placed in a preheated oil bath at 120° C. and stirred at this temperature for 3.5 hours while illuminating. The solvent was removed in vacuo and the residue was twice purified by column chromatography using 40% ethyl acetate in chloroform as eluant (1.02 g, 40%), mp 190–195° C., $^1$H-NMR (DMSO-d$_6$) 2.14 (s, 3H, CH$_3$CO), 4.91, 4.97 (2×s, 4H, 2-CH$_2$ and 6-CH$_2$), 7.78 (s, 1H, 8-H), 8.36 (s, 1H, 5-H), 12.61 (s, 1H, N$^3$—H). This product was used in the next experiment without any further purification.

PREPARATION EXAMPLE 25 tert-Butyl 4-[N-[2-Acetoxymethyl-7-chloro-4-oxo-3,4-dihydroquinazolin-6-ylmethyl]-N-(prop-2-ynyl) amino]benzoate To a stirred solution of 2-acetoxymethyl-6-bromomethyl-7-chloro-3,4-dihydroquinazolin-4-one (1.02 g, 3.0 mmol) in anhydrous DMF (100 ml) was added tert-butyl 4-N-(prop-2-ynyl)aminobenzoate (0.78 g, 3.4 mmol) followed by 2,6-lutidine (1.23 ml, 10.6 mmol). The reaction mixture was placed in a preheated oil bath at 120° C. and stirred at this temperature for 16 hours under argon, then it was allowed to cool to room temperature. The solvent was removed in vacuo and the residue was partitioned between ethyl acetate (300 ml) and half saturated brine (300 ml). The aqueous layer was extracted with more ethyl acetate (2×100 ml); the combined organic extracts were washed with brine (100 ml), dried (MgSO$_4$) and concentrated in vacuo. Purification by column chromatography on elution with 30% ethyl acetate in chloroform afforded a white solid (0.713 g, 48%), mp 219–220° C.; $^1$H-NMR (DMSO-d$_6$) 1.49 (s, 9H, Bu$^t$), 2.12 (s, 3H, CH$_3$CO), 3.25 (s, 1H, C≡CH), 4.40 (s, 2H, CH$_2$C≡C), 4.78 (s, 2H, 6-CH$_2$), 4.94 (s, 2H, 2-CH$_2$), 6.78 (d, J=8.8 Hz, 2H, 3',5'-ArH), 7.72 (d, J=8.8 Hz, 2H, 2',6'-ArH), 7.81, 7.83 (2×s, 5-H, 8-H), 12.52 (s, 1H, N$^3$—H); FAB-HRMS: measured: 495.1551; calculated for $C_{26}H_{26}N_3ClO_5$ 495.1561.

Elemental Analysis: Found: C, 62.98; H, 5.27; N, 8.43. $C_{26}H_{26}ClN_3O_5$ requires: C, 62.97; H, 5.28; N, 8.47%.

PREPARATION EXAMPLE 26 tert-Butyl 4-[N-[7-Chloro-2-hydroxymethyl-4-oxo-3,4-dihydroquinazolin-6-ylmethyl]-N-(prop-2-ynyl) amino]benzoate To a solution of tert-butyl 4-[N-[2-acetoxymethyl-7-chloro-4-oxo-3,4-dihydroquinazolin-6-ylmethyl]-N-(prop-2-ynyl)amino]benzoate (0.070 g, 0.14 mmol) in THF (2.7 ml) was dropwise added aqueous NaOH (1N, 0.27 ml, 0.27 mmol) followed by water (0.2 ml). The reaction mixture was stirred at room temperature for 2 hours, then the THF was removed in vacuo. The residue was suspended in water (10 ml) and the pH was adjusted to ~5 with 1N HCl. The white precipitate was collected by filtration, dried in vacuo and then it was reprecipitated from dichloromethane/hexanes to afford the title compound as a white solid (0.044 g, 70%), mp 185–187° C.; $^1$H-NMR (DMSO-d$_6$) 1.49 (s, 9H, Bu$^t$), 3.25 (s, 1H, C≡CH), 4.35, 4.38 (2×s, 4H, CH$_2$C≡C and 2-CH$_2$), 4.78 (s, 2H, 6-CH$_2$), 5.62 (br s, 1H, OH), 6.78 (d, J=8.7 Hz, 2H, 3',5'-ArH), 7.73 (d, J=8.6 Hz, 2H, 2',6'-ArH), 7.78, 7.84 (2×s, 2H, 5-H, 8-H), 12.07 (s, 1H, N$^3$—H); FAB-HRMS: measured: 453.1463, calculated for $C_{24}H_{24}ClN_3O_4$: 453.1455.

Elemental Analysis: Found: C, 62.50; H, 5.33; N, 9.26. $C_{24}H_{24}ClN_3O_4$ 0.25$H_2O$ requires: C, 62.88; H, 5.38; N, 9.16%.

PREPARATION EXAMPLE 27 tert-Butyl 4-[N-[7-Chloro-2-methanesulphonyloxymethyl-4-oxo-3,4-dihydroquinazolin-6-ylmethyl]-N-(prop-2-ynyl) amino]benzoate To a solution of tert-butyl 4-[N-[7-chloro-2-hydroxymethyl-4-oxo-3,4-dihydroquinazolin-6-ylmethyl]-N-(prop-2-ynyl)amino]benzoate (0.250 g, 0.55 mmol) in anhydrous DMF (6 ml) under argon was added methanesulphonic anhydride (0.191 g, 1.10 mmol) followed immediately by triethylamine (0.27 ml, 1.93 mmol). The clear solution was stirred at room temperature for 45 min then it was partitioned between ethyl acetate (200 ml) and saturated aqueous sodium bicarbonate (60 ml). The organic layer was washed with more saturated aqueous sodium bicarbonate (60 ml), brine (60 ml), dried (Na$_2$SO$_4$) and concentrated in vacuo. Purification by column chromatography on elution with 40% ethyl acetate in dichloromethane afforded a white solid (0.212 g, 73%), mp 178–181° C. $^1$H-NMR (DMSO-d$_6$): 1.49 (s, 9H, CO$_2$Bu$^t$), 3.23 (s, 1H, C≡CH), 3.20 (s, 3H, SO$_2$Me), 4.39 (s, 2H, CH$_2$C≡C), 4.78 (s, 2H, 6-CH$_2$), 5.11 (s, 2H, 2-CH$_2$), 6.78 (d, J=9.0 Hz, 2H, 3',5'-ArH), 7.72 (d, J=8.8 Hz, 2H, 2',6'-ArH), 7.85, 7.88 (2×s, 2H, 5-H, 8-H); MS (ESI, m/z) 554, 556 [(M+Na)$^+$, 100%, 38% respectively; Cl isotopic pattern].

Elemental Analysis: Found: C, 56.66; H, 4.91; N, 7.90. C$_{25}$H$_{26}$ClN$_3$O$_6$S requires: C, 56.44; H, 4.93; N, 7.90%.

PREPARATION EXAMPLE 28 tert-Butyl 4-[N-[7-Chloro-2-(piperidin-1-yl)methyl-4-oxo-3,4-dihydroquinazolin-6-ylmethyl]-N-(prop-2-ynyl)amino]benzoate To a solution of tert-butyl 4-[N-[7-chloro-2-methanesulphonyloxymethyl-4-oxo-3,4-dihydroquinazolin-6-ylmethyl]-N-(prop-2-ynyl)amino]benzoate (0.201 g, 0.38 mmol) in anhydrous DMF (5 ml) was added piperidine (0.323 g, 3.8 mmol) and the clear solution was stirred at room temperature for 2.5 hours. The reaction mixture was then partitioned between ethyl acetate (200 ml) and 5% aqueous sodium carbonate (70 ml). The organic layer was washed with 5% aqueous sodium carbonate (70 ml), brine (100 ml), dried (Na$_2$SO$_4$), and concentrated in vacuo. Purification by column chromatography on elution with ethyl acetate/dichloromethane (v/v, 1:1) afforded a white solid (0.179 g, 91%), mp 208–210° C.; $^1$H-NMR (DMSO-d$_6$) 1.36 (m), 1.48 (m(obscured)), 1.49 (s) (15H, $^t$Bu and piperidine CH$_2$H$_2$CH$_2$) 2.42, (br s, 4H, piperidine CH$_2$NCH$_2$), 3.61 (s, 2H, 2-CH$_2$), 3.22 (s, 1H, C≡CH), 4.38 (s, 2H, CH$_2$C≡C), 4.77 (s, 2H, 6-CH$_2$), 6.77 (d, J=9.0 Hz, 2H, 3',5'-ArH), 7.72 (d, J=8.9 Hz, 2',6'-ArH), 7.79, 7.83 (2×s, 2H, 5-H, 8-H), 11.96 (s, 1H, N$^3$—H).; MS (ESI, m/z) 521, 523 [(M+H)$^+$, 100%, 35% respectively; Cl isotopic pattern].

Elemental Analysis: Found: C, 66.71; H, 6.41; N, 10.50; Cl, 6.85. C$_{29}$H$_{33}$ClN$_4$O$_3$ requires: C, 66.85; H, 6.38; N, 10.75; Cl, 6.80%.

PREPARATION EXAMPLE 29 tert-Butyl 4-[N-[7-Chloro-3-diethylcarbamoylmethyl-4-oxo-2-(piperidin-1-yl)methyl-3,4-dihydroquinazolin-6-ylmethyl]-N-(prop-2-ynyl)amino]benzoate To a solution of tert-butyl 4-[N-[7-chloro-4-oxo-2-(piperidin-1-yl)methyl-3,4-dihydroquinazolin-6-ylmethyl]-N-(prop-2-ynyl)amino]benzoate (0.088 g, 0.17 mmol) (Preparation Example 28) in anhydrous DMF (2 ml) was added a sodium hydride (60% dispersion in mineral oil, 8.2 mg, 0.2 mmol).in one portion. The reaction mixture was stirred at room temperature for 3 min under argon; then a solution of N,N-diethylbromoacetamide (N. L. Drake et al, *J. Amer. Chem. Soc.* 1948, 70, 677–680; 0.066 g, 0.36 mmol) in anhydrous DMF (0.4 ml) was added. The clear solution was stirred at room temperature for 2.5 hours then partitioned between ethyl acetate (40 ml) and brine (40 ml). The aqueous layer was extracted with more ethyl acetate (2×30 ml) and the combined ethyl acetate extracts were washed with brine (30 ml), dried (Na$_2$SO$_4$) and concentrated in vacuo. Purification by column chromatography on elution with a gradient of ethyl acetate in hexane (20 to 50%) afforded a white solid (0.081 g, 76%), mp 95–97° C.; $^1$H-NMR (CDCl$_3$) 1.13, 1.33 (2×t, J=7.1 Hz, 6H, 2×CH$_2$CH$_3$), 1.42 (m obscured, 6H, piperidine CH$_2$CH$_2$CH$_2$), 1.55 (s, 9H, $^t$Bu), 2.27 (s, 1H, C≡CH), 2.42 (m, 4H, piperidine CH$_2$NCH$_2$), 3.41 (m, 4H, 2×CH$_2$CH$_3$), 3.52 (s, 2H, 2-CH$_2$), 4.17 (s, 2H, CH$_2$C≡C), 4.75 (s, 2H, 6-CH$_2$), 5.30 (s, 2H, N$^3$—CH$_2$), 6.73 (d, J=9.0 Hz, 2H, 3',5'-ArH), 7.78, 8.08 (2×s, 2H, 5-H, 8-H), 7.86 (d, J=9.02 Hz, 2H, 2',6'-ArH);); MS (ESI, m/z) 634, 636 [(M+H)$^+$, 100%, 37% respectively; Cl isotopic pattern].

Elemental Analysis: Found: C, 65.88; H, 7.16; N, 10.53. C$_{35}$H$_{44}$ClN$_5$O$_4$ requires: C, 66.28; H, 6.99; N. 11.04%.

PREPARATION EXAMPLE 30 tert-Butyl 4-[N-[7-Chloro-4-oxo-2-(piperidin-1-yl) methyl-3-piperidinocarbonylmethyl-3,4-dihydroquinazolin-6ylmethyl]-N-(prop-2-ynyl) amino]benzoate To a solution of tert-butyl 4-[N-[7-chloro-4-oxo-2-(piperidin-1-yl)methyl-3,4-dihydroquinazolin-6-ylmethyl]-N-(prop-2-ynyl)amino]benzoate (0.052 g, 0.10 mmol) in anhydrous DMF (1 ml) was added sodium hydride (60% dispersion in mineral oil, 5.00 mg, 0.12 mmol) in one portion. The reaction mixture was stirred at room temperature for 3 min under argon; then a solution of 1-(bromoacetyl)piperidine (M. Arimoto et al. *The Journal of Antibiotics* 1986, 1243–1256; 0.041 g, 0.2 mmol) in anhydrous DMF (0.2 ml) was added. The clear solution was stirred at room temperature for 3 hours then partitioned between ethyl acetate (40 ml) and brine (40 ml). The aqueous layer was extracted with ethyl acetate (2×20 ml) and the combined ethyl acetate extracts were washed with brine (30 ml) dried (Na$_2$SO$_4$) and concentrated in vacuo. Purification by column chromatography on elution with a gradient of ethyl acetate in hexanes (40 to 50%) afforded a white solid (0.040 g, 62%), mp>104° C.; $^1$H-NMR (DMSO-d$_6$) 1.30–1.65 (m, 12H), 2.36 (br s, 4H) and 3.40 (m, 4H), (piperidine protons), 1.49 (s, 9H, $^t$Bu), 3.21 (s, 1H, C≡CH), 3.47 (s, 2H, 2-CH$_2$), 4.39 (s, 2H, CH$_2$C≡C), 4.80 (s, 2H, 6-CH$_2$), 5.10 (s, 2H, N$^3$—CH$_2$), 6.78 (d, J=8.9 Hz, 2H, 3',5'-ArH), 7.83, 7.84 (2×s, 2H, 5-H, 8-H), 7.73 (d, J=8.8 Hz, 2H, 2',6'-ArH); MS (ESI, m/z) 646, 648 [(M+H)$^+$, 100%, 36% respectively; Cl isotopic pattern].

Elemental Analysis: Found: C, 65.84; H, 6.69; N, 10.42. C$_{36}$H$_{44}$ClN$_5$O$_4$ 0.5H$_2$O requires: C, 65.99; H, 6.92; N, 10.68%.

PREPARATION EXAMPLE 31 tert-Butyl 4-[N-[7-Chloro-3-methoxycarbonylmethyl-4-oxo-2-piperidin-1-ylmethyl-3,4-dihydroquinazolin-6-ylmethyl]-N-(prop-2-ynyl)amino]benzoate To a solution of of tert-butyl 4-[N-[7-chloro-4-oxo-2-piperidin-1-ylmethyl-3,4-dihydroquinazolin-6-ylmethyl]-N-(prop-2-ynyl)amino]benzoate (0.096 g, 0.18 mmol) in anhydrous DMF (5 ml) under argon was added sodium hydride (60% dispersion in mineral oil, 8 mg, 0.2 mmol) in one portion. The reaction mixture was stirred at room temperature for 3 min, then methyl bromoacetate (0.141 g, 0.9 mmol) was added dropwise. The reaction mixture was stirred at room temperature for 24 hours then partitioned between ethyl acetate (150 ml) and half saturated brine (100 ml). The organic layer was washed with more brine (100 ml). The combined aqueous washings were extracted with ethyl acetate (2×50 ml). The combined ethyl acetate extracts were washed with brine (100 ml), dried (Na$_2$SO$_4$) and concentrated in vacuo. Purification by column chromatography on elution with chloroform afforded a white solid (0.071 g, 67%), mp 148–150° C.; $^1$H-NMR (DMSO-d$_6$) 1.36 (m, 6H, piperidine CH$_2$CH$_2$CH$_2$), 1.50 (s, 9H, Bu$^t$), 2.32, (m, 4H, piperidine CH$_2$NCH$_2$), 3.23 (s, 1H, C≡CH), 3.58 (s, 2H, 2-CH$_2$), 3.67 (s, 3H, CO$_2$Me), 4.40 (d, J=2.0 Hz, 2H, CH$_2$C≡C), 4.80 (s, 2H, 6-CH$_2$), 4.87 (s, 2H, N$^3$—CH$_2$), 6.77 (d, J=9.0 Hz, 2H, 3',5'-ArH), 7.72 (d, J=8.9 Hz, 2',6'-ArH), 7.86, 7.87 (2×s, 2H, 5-H, 8-H); MS (FAB, m/z) 593, 595 [(M+H)$^+$, 100%, 36% respectively; Cl isotopicpattern].

FAB-HRMS: measured: 593.2506; calculated for C$_{32}$H$_{38}$ClN$_4$O$_5$ 593.2531.

PREPARATION EXAMPLE 32 tert-Butyl 4-[N-[7-Chloro-3-(2-dimethylaminoethyl)-4-oxo-2-piperidin-1-ylmethyl-3,4-dihydroquinazolin-6-ylmethyl]-N-(prop-2-ynyl) amino]benzoate To a solution of of tert-butyl 4-[N-[7-chloro-4-oxo-2-piperidin-1-ylmethyl-3,4-dihydroquinazolin-6-ylmethyl]-N-(prop-2-ynyl)amino]benzoate (0.250 g, 1.69 mmol) in anhydrous DMF (10 ml) under argon was added lithium chloride (0.071 g, 6.24 mmol). When the lithiumn chloride had dissolved the reaction mixture was cooled to 4° C. in an ice-bath and then sodium hydride (60% dispersion in mineral oil, 21 mg, 0.52 mmol) in one portion followed by 2-dimethylaminoethyl chloride (free base, 0.690 g, 6.40 mmol). Stirring was continued at 4° C. for 15 min and then for an additional 16 h at room temperature. The reaction mixture was then heated to 70° C. and then more sodium hydride (60% dispersion in mineral oil, 10 mg, 0.25 mmol) was added followed by 2-dimethylaminoethyl chloride (free base, 0.690 g, 6.40 mmol). Stirring was continued at this temperature for 2 hours under argon; the the solvent was removed in vacuo and the residue was partitioned between ethyl acetate (150 ml) and water (200 ml). The organic layer was washed with more water (150 ml). The aqueous washings were extracted with more ethyl acetate (2×50 ml). The combined ethyl acetate extracts were washed with brine ((50 ml), dried (Na$_2$SO$_4$) and concentrated in vacuo. Purification by column chromatography on elution with ether/hexanes/ MeOH (v/v/v: 5:4: 1) afforded a white solid (0.074 g, 26%), mp 75–77° C.; $^1$H-NMR (DMSO-d$_6$) 1.35–1.49 (m, 15H, $^t$Bu, piperidine CH$_2$CH$_2$CH$_2$), 2.19 (s, 6H, NMe$_2$), 2.40 (m, 4H, piperidine CH$_2$NCH$_2$), 2.53 (t (obscured), 2H, Me$_2$NCH$_2$), 3.27 (s, 1H, C≡CH), 3.61 (s, 2H, 2-CH$_2$), 4.23 (t, J=7.0 Hz, 2H, N$^3$—CH$_2$), 4.40 (s, 2H, CH$_2$C≡C), 4.79 (s, 2H, 6-CH$_2$), 6.77 (d, J=9.0 Hz, 2H, 3',5'-ArH), 7.72 (d, J=8.9 Hz, 2',6'-ArH), 7.82, 7.87 (2×s, 2H, 5-H, 8-H); MS (ESI, m/z) 592, 594 [(M+H)$^+$, 100%, 38% respectively; Cl isotopic pattern].

Elemental Analysis: Found: C, 66.45; H, 7.12; N, 11.41; C$_{33}$H$_{42}$ClN$_5$O$_3$ 0.25H$_2$O requires: C, 66.42; H, 7.13; N, 11.73%.

PREPARATION EXAMPLE 33

2-Chloromethyl-3,4,7,8-tetrahydro-6H-cyclopenta[g] quinazolin-4-one

Anhydrous methanol (36 ml) was added into a 250 ml round-bottomed flask that contained sodium (0.081 g) under argon. To this stirred solution chloroacetonitrile (1.56 g, 20.7 mmol) was added and stirring was continued for 30 min at room temperature under argon. 5-Amino-6-carboxyindane (European Patent Application 0602851A1; 3.19 g, 18.0 mmol) was then added and the reaction mixture was diluted with more methanol (42 ml). After the reaction mixture being stirred for 1 hour at room temperature, more anhydrous methanol (25 ml) was added and stirring was continued for 1 hour at room temperature and then for a further 1 hour at 80° C. under argon. The reaction mixture was then allowed to cool to room temperature; the white precipitate was collected by filtration, washed with methanol, water and dried in vacuo over P$_2$O$_5$ (3.15 g, 75%), mp 270–272° C.; $^1$H-NMR (DMSO-d$_6$) 2.07 (m, 2H, 7-CH$_2$), 2.98 (m, 4H, 6-CH$_2$ and 8-CH$_2$), 4.52 (s, 2H, 2-CH$_2$), 7.50 (s, 1H, 9-H), 7.93 (s, 1H, 5-H), 12.37, (s, 1H, N$^3$—H). MS (FAB, m/z) 235 (M+H)$^+$;

Elemental Analysis: Found: C, 61.46; H, 4.84; N, 12.03; Cl, 14.91%. C$_{12}$H$_{11}$N$_2$ClO requires: C, 61.42; H, 4.72; N, 11.94; Cl, 15.11%.

PREPARATION EXAMPLE 34

2-Acetoxymethyl-3,4,7,8-tetrahydro-6H-cyclopenta [g]quinazolin-4-one

A solution of powdered and dried cesium acetate (41.00 g, 213.5 mmol) in DMF (150 ml) was heated at 60° C. and stirred at this temperature for 30 min under argon. The reaction mixture was cooled to 40° C. and then a solution of 2-chloromethyl-3,4,7,8-tetrahydro-6H-cyclopenta[g] quinazolin-4-one (10.00 g, 42.7 mmol) in DMF (350 ml) was added via a cannula under argon. The reaction mixture was heated to 80° C. and stirred for 3 hours at this temperature. The solvent was then removed in vacuo and the residue was stirred with chloroform (500 ml), then it was filtered through a celite. The celite was washed with chloroform (2×100 ml); the combined organics were washed with water (2×150 ml), brine (100 ml), dried (MgSO$_4$) and concentrated in vacuo to leave a beige solid. Recrystallisation from toluene (twice) afforded a white solid (4.4 g, 40%) mp>200° C. (dec); $^1$H-NMR (DMSO-d$_6$) 2.04 (m, 2H, 7-CH$_2$), 2.12 (s, 3H, CH$_3$CO), 2.98 (m, 4H, 6-CH$_2$ and 8-CH$_2$), 4.94 (s, 2H, 2-CH$_2$), 7.47 (s, 1H, 9-H), 7.92 (s, 1H, 5-H), 12.26, (s, 1H, N$^3$—H). MS (ESI, m/z) 217 (M-CH$_3$CO)$^+$.

PREPARATION EXAMPLE 35

2-Acetoxymethyl-3-pivaloyloxymethyl-3,4,7,8-tetrahydro-6H-cyclopenta[g]quinazolin-4-one To a solution of 2-acetoxymethyl-3,4,7,8-tetrahydro-6H-cyclopenta[g]quinazolin-4-one (1.00 g, 3.9 mmol) in DMA (45 ml) was added powdered potassium carbonate (1.35 g, 9.8 mmol). The reaction mixture was stirred for 1 hour at room temperature under argon, then it was placed in an ice-bath and chloromethyl pivalate (0.880 g, 5.8 mmol) was added dropwise. The ice-bath was removed and stirring was continued for a further 16 hours under argon. The solvent was removed in vacuo and the residue was partitioned between ethyl acetate (50 ml) and water (50 ml). The aqueous layer was extracted with more ethyl acetate (3×30 ml). The ethyl acetate extracts were combined, washed with brine (40 ml), dried (MgSO$_4$) and concentrated in vacuo. Purification by column chromatography using 40% ether in hexane as eluant afforded in order of elution: 2-acetoxymethyl-4-pivaloyloxymethyloxy-7,8-tetrahydro-6H-cyclopenta[g]quinazoline as a colourless oil (0.875 g, 60%); $^1$H-NMR (DMSO-d$_6$) 1.10 (s, 9H, POM C(CH$_3$)$_3$)$_3$), 2.08 (m, 2H, 7-CH$_2$), 2.16 (s, 3H, CH$_3$CO), 2.98 (m, 4H, 6-CH$_2$ and 8-CH$_2$), 5.20 (s, 2H, 2-CH$_2$), 6.23 (s, 2H, POM CH$_2$), 7.72, 7.88 (2×s, 2H, 9-H, 5-H); MS (ESI, m/z) 373 (M+H)$^+$;

Elemental Analysis: Found: C, 64.45; H, 6.54; N, 7.41. C$_{20}$N$_{24}$N$_2$O$_5$ requires: C, 64.50; H, 6.50; N, 7.52%.

2-acetoxymethyl-3-pivaloyloxymethyl-3,4,7,8-tetrahydro-6H-cyclopenta[g]quinazolin-4-one as a solid (0.380 g, 26%), mp 132–135° C.; $^1$H-NMR (DMSO-d$_6$) 1.12 (s, 9H, POM C(CHd$_3$)$_3$), 2.07 (m, 2H, 7-CH$_2$), 2.16 (s, 3H, CH$_3$CO), 2.98 (m, 4H, 6-CH$_2$ and 8-C$_2$), 5.25 (s, 2H, 2-CH$_2$), 6.03 (s, 2H, POM CH$_2$), 7.50 (s, 1H, 9-H) 7.96 (s, 1H, 5-H); MS (ESI, m/z) 373 (M+H)$^+$;

Elemental Analysis: Found: C, 64.43; H, 6.53; N, 7.54. C$_{20}$N$_{24}$N$_2$O$_5$ requires: C, 64.50; H, 6.50; N, 7.52%.

PREPARATION EXAMPLE 36

2-Acetoxymethyl-3-pivaloyloxymethyl-3,4,7,8-tetrahydro-6H-cyclopenta[g]quinazolin-4,6-dione To a vigorously stirred suspension of chromium(VI) oxide (0.040 g) in dichloromethane (15 ml) cooled in an ice-bath was added tert-butyl hydroperoxide (70% aqueous solution, 7.21 g, 56.0 mmol) dropwise. The ice-bath was then removed, the reaction mixture was allowed to stir for 10 min at room temperature and then a solution of 2-acetoxymethyl-3-pivaloyloxymethyl-3,4,7,8-tetrahydro-6H-yclopenta[g]quinazolin-4-one (1.50 g, 4.0 mmol) in dichloromethane (10 ml) was added dropwise. The red reaction mixture was stirred for 24 hours at room temperature then it was cooled in an ice-bath and then 10% aqueous sodium metabisulfite solution (20 ml) was added dropwise. The reaction mixture was allowed to stir for 2 hours at room temperature; then it was partitioned between ethyl acetate (50 ml) and half-saturated brine (50 ml). The aqueous layer was extracted with more ethyl acetate (3×30 ml). The ethyl acetate extracts were combined, washed with saturated aqueous sodium bicarbonate (50 ml), brine (50 ml), dried (MgSO$_4$) and concentrated in vacuo. Purification by column chromatography on elution with a gradient of ethyl acetate in hexanes (20 to 50%) afforded in order of elution: 2-acetoxymethyl-3-pivaloyloxymethyl-3,4,7,8-tetralhydro-6H-cyclopenta[g]quinazolin-4,8-dione as a white solid (0.381 g, 25%), mp 144° C.; $^1$H-NMR (CDCl$_3$) 1.13 (s, 9H, POM C(CH$_3$)$_3$), 2.16 (s, 3H, CH$_3$CO), 2.74 (m, 2H, 7-CH$_2$), 3.20 (m, 2H, 6-CH$_2$), 5.16 (s, 2H, 2-CH$_2$), 6.05 (s, 2H, POM CH$_2$), 7.93 (s, 1H, 9-H), 8.30 (s, 1H, 5-H); MS (ESI, m/z) 387 (M+H)$^+$; 2-acetoxymethyl-3-pivaloyloxymethyl-3,4,7,8-tetrahydro-6H-cyclopenta[g]quinazolin-4,6-dione as a white solid (0.697 g, 45%), mp 147° C.; $^1$H-NMR (CDCl$_3$) 1.17 (s, 9H, POM C(CHd$_3$)$_3$), 2.19 (s, 3H, CH$_3$CO), 2.80 (m, 2H, 7-CH$_2$), 3.27 (m, 2H, 8-CH$_2$), 5.19 (s, 2H, 2-CH$_2$), 6.09 (s, 2H, POM CH$_2$), 7.70 (s, 1H, 9-H) 8.66 (s, 1H, 5-H); MS (ESI, m/z) 387 (M+H)$^+$.

PREPARATION EXAMPLE 37 tert-Butyl 4-[N-[2-Acetoxymethyl-4-oxo-3-pivaloyloxymethyl-3,4,7,8-tetrahydro-6H-cyclopenta[g]quinazolin-6-yl]amino]benzoate 2-Acetoxymethyl-3-pivaloyloxymethyl-3,4,7,8-tetrahydro-6H-cyclopenta[g]quinazolin-4,6-dione (0.140 g, 0.36 mmol) was suspended in anhydrous methanol (8 ml) and then anhydrous dichoromethane (4 ml) was added until a clear solution was obtained. Tert-butyl 4-aminobenzoate (0.084 g, 0.44 mmol) was then added followed by decaborane (0.014 g, 0.12 mmol). The reaction mixture was stirred overnight at room temperature under argon. The solvent was removed in vaciio, and the residue was purified by column chromatography on elution with 40% ethyl acetate in hexane. The product was obtained as a glass (0.127 g, 63%) $^1$H-NMR (CDCl$_3$) 1.20 (s, 9H, POM C(CH$_3$)$_3$), 1.58 (s, 9H, CO$_2$C(CH$_3$)$_3$), 2.20 (s, 3H, CH$_3$CO), 2.02, 2.72 (2×m, 2H, 7-CH$_2$), 3.13 (m, 2H, 8-CH$_2$), 4.36 (d, J=7.7 Hz, 1H, NH), 5.15 (q, J=6.8 Hz, 1H, 6-H), 5.21 (s, 2H, 2-CH$_2$), 6.12 (AB system, J=10.7 Hz, 2H, POM CH$_2$), 6.67 (d, J=8.8 Hz, 2H, 3,5'-ArH), 7.57 (s, 1H, 9-H), 7.85 (d, J=8.9 Hz, 2H, 2',6'-ArH), 8.25 (s, 1H, 5-H); MS (ESI, m/z) 564 (M+H)$^+$.

PREPARATION EXAMPLE 38 tert-Butyl 4-[N-[-2-Acetoxymethyl-4-oxo-3-pivaloyloxymethyl-3,4,7,8-tetrahydro-6H-cyclopenta[g]quinazolin-6-yl]-N-methylamino]benzoate To a stirred solution of tert-butyl 4-[N-[-2-acetoxymethyl-4-oxo-3-pivaloyloxymethyl-3,4,7,8-tetrahydro-6H-cyclopenta[g]quinazolin-6-yl]amino]benzoate (0.060 g, 0.106 mmol) in THF (6 ml) was added glacial acetic acid (2 ml) followed by 37% aqueous formaldehyde (0.090 ml). The solution was stirred for 2.5 hours at room temperature and then sodium cyanoborohydride (0.017 g, 0.27 mmol) was added. The reaction mixture was stirred overnight at room temperature. The solvent was removed in vacuo and the residue was partitioned between ethyl acetate (25 ml) and water (25 ml). The aqueous layer was extracted with more ethyl acetate (2×25 ml). The combined organics were washed with saturated aqueous sodium bicarbonate (30 ml), brine (30 ml), dried (Na$_2$SO$_4$) and concentrated in vacuo to leave an oil (0.060 g, 98%); $^1$H-NMR (CDCl$_3$) 1.20 (s, 9H, POM C(CH$_3$)$_3$), 1.58 (s, 9H, CO$_2$C(CH$_3$)$_3$), 2.15 (s, 3H, CH$_3$CO), 2.02, 2.52 (2×m, 2H, 7-CH$_2$), 2.74 (s, 3H, N$^{10}$-Me), 3.13 (m, 2H, 8-CH$_2$) 5.21 (s, 2H, 2-CH$_2$), 5.66 (t, 1H, J=8.1 Hz, 6-H), 6.12 (AB system, J=10.8 Hz, 2H, POM CH$_2$), 6.85 (d, J=8.8 Hz, 2H, 3,5'-ArH), 7.58 (s, 1H, 9-H), 7.90 (d, J=8.9 Hz, 2H, 2,6'-ArH), 8.08 (s, 1H, 5-H); MS (ESI, m/z) 578 (M+H)$^+$.

PREPARATION EXAMPLE 39 tert-Butyl 4-[N-[2-Hydroxymethyl-4-oxo-3,4,7,8-tetrahydro-6H-cyclopenta[g]quinazolin-6yl]-N-methylamino]benzoate To a stirred solution of tert-butyl 4-[N-[-2-acetoxymethyl-4-oxo-3-pivaloyloxymethyl-3,4,7,8-tetrahydro-6H-cyclopenta[g]quinazolin-6-yl]-N-methylamino]benzoate (0.060 g, 0.106 mmol) in methanol (2.5 ml) was added aqueous NaOH solution (1M, 0.4 ml, 0.4 mmol) followed by water (0.5 ml). The solution was stirred overnight at room temperature, then the methanol was removed in vacuo, and the pH of the aqueous residue was adjusted to ~4 with 1N HCl to give a milky suspension. This was extracted with ethyl acetate (3×25 ml); the combined extracts were washed with water (20 ml), brine (20 ml), dried (Na$_2$SO$_4$) and concentrated in vacuo to give an off-white solid (0.045 g, 100%) $^1$H-NMR (CDCl$_3$) 1.58 (s, 9H, CO$_2$C(CH$_3$)$_3$), 2.04, 2.52 (2×m, 2H, 7-CH$_2$), 2.75 (s, 3H, N$^{10}$-Me), 3.13 (m, 2H, 8-CH$_2$), 4.71 (s, 2H, 2-CH$_2$), 5.66 (t, 1H, J=8.1 Hz, 6-H), 6.86 (d, J=9.0 Hz, 2H, 3,5'-ArH), 7.56 (s, 1H, 9-H), 7.89 (d, J=8.9 Hz, 2H, 2,6'-ArH), 8.05 (s, 1H, 5-H); MS (ESI, m/z) 444 [(M+Na)$^+$ , 100%], 422 [(M+H)$^+$, 20%]. This compound was also made from 2-acetoxymethyl-4-pivaloyloxymethyloxy-7,8-tetrahydro-6H-cyclopenta[g]quinazoline by first brominating this compound, followed by the displacement of the bromide with tert-butyl 4-aminobenzote, then methylation and finally removal of the POM and acetyl groups under alkaline conditions.

PREPARATION EXAMPLE 40 tert-Butyl 4-[N-[2-(Methanesulphonyl)methyl-4-oxo-3,4,7,8-tetrahydro-6H-cyclopenta[g]quinazolin-6-yl]-N-methylamino]benzoate To a solution of tert-butyl 4-[N-[2-hydroxymethyl-4-oxo-3,4,7,8-tetrahydro-6H-cyclopenta[g]quinazolin-6-yl]-N-methylamino]benzoate (0.130 g, 0.31 mmol) in anhydrous DMF (4 ml) under argon was added methanesulphonic anhydride (0.1 12 g, 0.64 mmol) followed immediately by triethylamine (0.16 ml, 1.12 mmol). The solution was stirred for 45 min after which time the reaction mixture was partitioned between a saturated aqueous solution of sodium bicarbonate (40 ml) and ethyl acetate (75 ml). The organic phase was then successively washed with a saturated aqueous solution of sodium bicarbonate (30 ml) and brine (30 ml), then dried ($Na_2SO_4$) and concentrated under reduced pressure. Flash column chromatography with dichloromethane-ethyl acetate (3:2 v/v) afforded the title compound (0.70 g, 45%) $^1$H NMR (DMSO-$d_6$) 1.51 (s, 9H, C($CH_3$)$_3$), 2.03, 2.45 (2×m, 2H, 7-$CH_2$), 2.66 (s, 3H, $N^{10}$-Me), 3.02 (m, 2H, 8-$CH_2$), 3.34 (s, 3H, —$SO_2CH_3$), 5.12 (s, 2H, $CH_2$OMs), 5.78 (t, 1H, J=8.0 Hz, 6-H), 6.96 (d, 2H, J=9.0 Hz, 3',5'-ArH), 7.58 (s, 1H, 9-H), 7.71 (s, 1H, 5-H), 7.75 (d, 2H, J=9.0 Hz, 2',6'-ArH); MS (ESI, m/z) 522 [(M+Na)$^+$ 100%, 500 (M+H)$^+$ 7%].

PREPARATION EXAMPLE 41 tert-Butyl 4-[N-[4-oxo-2-(Piperidin-1-yl)methyl-3,4,7,8-tetrahydro-6H-cyclopeuta[g]quiazolin-6-yl]-N-methylamino]benzoate To a solution of tert-butyl 4-[N-[2-(methanesulphonyl) methyl-4oxo-3,4,7,8-tetrahydro-6H-cyclopenta[g]quinazolin-6-yl]-N-methylamino]benzoate (0.070 g, 0.14 mmol) in anhydrous DMF (2.5 mL) was added piperidine (0.14 ml, 1.42 mmol) and the solution was stirred for 2.5 hours. The reaction mixture was partitioned between a saturated aqueous solution of sodium bicarbonate (35 ml) and ethyl acetate (75 ml). The organic phase was successively washed with a 10% (w/v) aqueous solution of sodium carbonate (25 ml), brine (25 ml), then dried ($Na_2SO_4$) and concentrated under reduced pressure to afford the title compound (0.067 g, 98%). $^1$H NMR (CDCl$_3$) 1.54 (m), 1.59 (s), 1.63 (m (obscured)) (15H, $^t$Bu and piperidine $CH_2CH_2CH_2$), 2.12 (m, 1H, 7-CH), 2.54 (m, 5H, 7-CH and piperidine $CH_2NCH_2$), 2.75 (s, 3H, $N^{10}$-Me), 3.09 (m, 2H, 8-$CH_2$), 3.51 (s, 2H, 2-$CH_2$), 5.66 (t, 1H, J 8.2 Hz), 6.85 (d, 2H, J=8.9 Hz, 3',5'-ArH), 7.53 (s, 1H, 9-H), 7.89 (d, 2H, J=8.9 Hz, 2',6'-ArH), 8.06 (s, 1H, 5-H); MS (ESI, m/z) 489 [(M+H)$^+$ 100%].

PREPARATION EXAMPLE 42 tert-Butyl 4-[N-[3-Methyl-4-oxo-2-(piperidin-1-yl) methyl-3,4,7,8-tetrahydro-6H-cyclopenta[g]quinazolin-6-yl]-N-methylamino]benzoate To a solution of tert-butyl 4-[N-[4-oxo-2-(piperidin-1-yl) methyl-3,4,7,8-tetrahydro-6H-cyclopenta[g]quinazolin-6-yl]-N-methylamino]benzoate (0.060 g, 0.123 mmol) in anhydrous DMF (3 ml) under argon was added a dispersion of NaH in mineral oil (60% w/w) (0.0060 g, 0.147 mmol) and the reaction mixture was stirred for 1 min. MeI (15 µL, 0.246 mmol) was then added via syringe and the reaction mixture was stirred for a further 2 hours. The reaction mixture was then partitioned between a saturated aqueous solution of sodium bicarbonate (40 ml) and ethyl acetate (75 ml) and the organic phase was then successively washed with a saturated aqueous solution of sodium bicarbonate (30 ml), brine (30 ml), then dried ($Na_2SO_4$) and concentrated under reduced pressure to afford the title compound (0.056 g, 91%).

$^1$H NMR (CDCl$_3$) $^1$H 1.46 (m), 1.59 (s) (15H, $^t$Bu and piperidine $CH_2CH_2CH_2$), 2.07 (m, 1H, 7-CH), 2.57 (m, 5H, 7-CH and piperidine $CH_2NCH_2$), 2.73 (s, 3H, $N^{10}$-Me), 3.08 (m, 2H, 8-$CH_2$), 3.58 (s, 2H, 2-$CH_2$), 3.77 (s, 3H, 3-Me) 5.66 (t, 1H, J=8.1 Hz), 6.85 (d, 2H, J=8.9 Hz, 3,'5'-ArH), 7.54 (s, 1H, 9-H), 7.90 (d, 2H, J=8.9 Hz, 2',6'-ArH), 8.05 (s, 1H, 5-H); MS (ESI, m/z) 503 [(M+H)$^+$ 100%].

EXAMPLE 1

4-[N-[7-Chloro-3-methyl-2-(4-methyl-piperazin-1-yl)methyl-4-oxo-3,4-dihydroquinazolin-6-ylmethyl]-N-(prop-2-ynyl)amino]-N-(3-pyridylmethyl) benzamide (CB 300919) and the Corresponding Hydrochloride Salt (CB 300921)

A solution of tert-butyl 4-[N-[7-chloro-3-methyl-2-(4-methyl-piperazin-1-yl)methyl-4-oxo-3,4-dihydroquinazolin-6-ylmethyl]-N-(prop-2-ynyl)amino] benzoate (Preparation Example 14) (0.094 g, 0.17 mmol) in dichloromethane (1.2 ml) and trifluoroacetic acid (1.6 ml) was stirred at room temperature for 55 min. The trifluoroacetic acid was then removed in vacuo, and the residue was treated with dichloromethane/toluene, concentrated in vacuo to leave a white solid which dried in vacuo over $P_2O_5$ (0.142 g). This solid was dissolved in anhydrous DMF (1.3 ml) under argon. The solution was placed in an ice-bath and then a solution of 3-(aminomethyl)pyridine (0.028 g, 0.255 mmol) in anhydrous DMF (0.2 ml) was added followed by PyBOP® (0.093 g, 0.178 mmol), and finally dilsopropyl-ethylamine (0.154 g, 1.19 mmol). The solution was stirred at 0° C. for 3 min, then the ice-bath was removed and stirring was continued under argon for 3 h. The clear solution was then partitioned between ethyl acetate (120 ml) and saturated aqueous sodium bicarbonate (60 ml). The organic layer was washed with more saturated aqueous sodium bicarbonate (50 ml), brine (40 ml), dried ($Na_2SO_4$) and concentrated invacuo. Purification by column chromatography, on gradient elution with methanol in dichloromethane (5 to 13%), afforded a glass. Reprecipitation from dichloromethane/hexanes afforded a white solid which was collected by filtration, washed with hexanes and dried in vacuo over $P_2O_5$ (0.070 g, 70%), mp 120° C. (softens); $^1$H-NMR (DMSO-$d_6$) 2.15 (s, 3H, N-Me piperazine), 2.23 (br s) and 2.49 br s obscured) (8H, N($CH_2CH_2$)$_2$N-Me), 3.17 (s(poorly resolved triplet), 1H, C≡CH), 3.60 (s, 3H, $N^3$-Me), 3.61 (s, 2H, 2-$CH_2$), 4.36 (d, J=1.72 Hz, 2H, $CH_2$C≡C), 4.45 (d, J=5.8 Hz, 2H, CONH$CH_2$), 4.77 (s, 2H, 6-$CH_2$), 6.78 (d, J=8.9 Hz, 2H, 3,5'-ArH), 7.31 (dd, J=4.8, 7.8 Hz, 1H, pyr 5-H), 7.68 (d, J=7.8 Hz, pyr 4-H), 7.75 (d, J=8.8 Hz, 2H, 2',6'-ArH), 7.80, 7.92 (2×s, 2H, 5-H, 8-H), 8.42 (d, J=4.9 Hz, pyr 6-H), 8.52 (d, J=1.6 Hz, 1H, 2-H pyr), 8.72 (t, J=5.82 Hz, 1H, CONH).

MS (FAB, m/z) 584, 587 [(M+H)$^+$, 100%, 36% respectively; Cl isotopic pattern]; Elemental Analysis: Found: C, 63.19; H, 5.79; N, 15.90; Cl, 6.20. $C_{32}H_{34}ClN_7O_2$ 1.2 $H_2O$ requires: C, 63.46; H. 6.05; N, 16.19; Cl, 5.85%.

The hydrochloride salt of the thus obtained compound was obtained by treatment with hydrochloric acid (1M in diethyl ether) in dichloromethane/methanol.

EXAMPLE 2

4-[N-[2-Diethylaminomethyl-7-chloro-3-methyl-4-oxo-3,4-dihydroquinazolin-6-ylmethyl]-N-(prop-2-ynyl)amino]-N-(3-pyridylmethyl)benzamide (CB 300922)

A solution of tert-butyl 4-[N-[2-diethylaminomethyl-7-chloro-3-methyl-4-oxo-3,4-dihydroquinazolin-6-ylmethyl]-N-(prop-2-ynyl)amino]benzoate (Preparation Example 15) (0.090 g, 0.17 mmol) in dichloromethane (1.2 ml) and trifluoroacetic acid (1.6 ml) was stirred at. room temperature for 55 min with protection from the light. The solvents were then removed in vacuo and the oily residue was treated with dicloromethane/toluene, then concentrated in vacuo and the solid was dried in vacuo over $P_2O_5$. This solid was dissolved in anhydrous DMF (1.3 ml) and the solution was placed in an ice-bath under argon. A solution of 3-(aminomethyl)pyridine (0.028 g, 0.255 mmol) in anhydrous DMF (0.2 ml) was added followed by PyBOP® (0.093 g, 0.178 mmol) and finally diisopropylethylamine (0.131 g, 1.02 mmol). Stirring was continued at 0° C. for 3 min; then the ice-bath was removed and stirring was continued for an additional 3 h. The reaction mixture was partitioned between ethyl acetate (200 ml) and saturated aqueous sodium bicarbonate (100 ml). The organic layer was washed with more saturated aqueous sodium bicarbonate (100 ml) and brine (100 ml), dried ($Na_2SO_4$) and concentrated in vacuo. Purification by column chromatography, on elution with a gradient of methanolin dichloromethane (2 to 3%), afforded a glass which was reprecipitated from dichloromethane/hexanes. The white solid was collected by filtration, washed with hexanes and dried in vacuo over $P_2O_5$ (0.049 g, 52%), mp 180–182° C.; $^1$H-NMR (DMSO-$d_6$) 0.95 (t, J=7.11 Hz, 6H, 2×$CH_2CH_3$), 2.58 (obscured, J=7.0 Hz, 4H, 2×$CH_2CH_3$), 3.19 (s, 1H, C≡CH), 3.62 (s, 3H, $N^3$-Me), 3.70 (s, 2H, 2-$CH_2$), 4.37 (s, 2H, $CH_2$C≡C), 4.44 (d, J=5.7 Hz, 2H, $CONHCH_2$), 4.77 (s, 2H, 6-$CH_2$), 6.78 (d, J=8.9 Hz, 2H, 3,5'-ArH), 7.32 (dd, J=4.8, 7.8 Hz, 1H, pyr 5-H), 7.67 (d, J=7.7 Hz, 1H, pyr 4-H), 7.75 (d, J=8.7 Hz, 2H, 2',6'-ArH), 7.80, 7.91 (2×s, 2H, 5-H, 8-H), 8.42 (d, J=5.3 Hz, pyr 6-H), 8.51 (s, 1H, pyr 2-H), 8.74 (t, J=6.03 Hz, 1H, CONH).; MS (ESI, m/z) 557,559 [(M+H)$^+$, 100%, 38% respectively; Cl isotopic pattern]. FAB-HRMS; measured 557.2414; calculated for $C_{31}H_{34}ClN_6O_2$ (M+H)$^+$: 557.2432.

EXAMPLE 3

4-[N-[7-Chloro-3-methyl-4-oxo-2-piperidinomethyl-3,4-dihydroquinazolin-6-ylmethyl]-N-(prop-2-ynyl)amino]-N-(3-pyridylmethyl)benzamide (CB 300923)

A solution of tert-butyl 4-[N-[7-chloro-3-methyl-4-oxo-2-piperidinomethyl-3,4-dihydroquinazolin-6-ylmethyl]-N-(prop-2-ynyl)amino]benzoate (Preparation Example 16) (0.086 g, 0.16 mmol) in dichloromethane (1.2 ml) and trifluoroacetic acid (1.6 ml) was stirred at room temperature for 55 min with protection from the light. The solvents were then removed in vacuo and the residue was treated with toluene/dichloromethane; concentrated in vacuo and the residue was dried in vacuo over $P_2O_5$. This solid was dissolved in anhydrous DMF (1.2 ml) under argon and the solution was placed in an ice-bath. A solution of 3-(aminomethyl)pyridine (0.026 g, 0.24 mmol) in DMF (0.2 ml) was then added followed by PyBOP® (0.087 g, 0.168 mmol) and diisopropylethylamine (0.123 g, 0.96 mmol). Stirring was continued at 0° C. for 3 min; then the ice-bath was removed and the reaction mixture was stirred for an additional 3 h at room temperature before being partitioned between ethyl acetate (200 ml) and saturated aqueous bicarbonate (100 ml). The organic layer was washed with more saturated aqueous bicarbonate (100 ml) and brine (100 ml), dried ($Na_2SO_4$) and concentrated in vacuo. The residue was purified by column chromatography using 3% methanol in dichloromethane as eluant, then triturated with 20% dichloromethane in hexanes to give a white solid which was collected by filtration, washed with hexanes and dried in vacuo over $P_2O_5$ (0.072 g, 79%), mp 148–150° C.; $^1$H-NMR (DMSO-$d_6$) 1.48 (br s, 6H, piperidine $CH_2CH_2CH_2$), 2.43 (br s, 4H, piperidine $CH_2NCH_2$), 3.18 (s, 1H, C≡CH), 3.61 (s, 3H, $N^3$-Me), 3.57 (s, 2H, 2-$CH_2$), 4.36 (s, 2H, $CH_2$C≡C), 4.45 (d, J=5.7 Hz, 2H, $CONHCH_2$), 4.77 (s, 2H, 6-$CH_2$), 6.79 (d, J=8.8 Hz, 2H, 3,5'-ArH), 7.32 (dd, J=4.8, 7.8 Hz, 1H, pyr 5-H), 7.68 (d, J=7.7 Hz, 1H, pyr 4-H), 7.76 (d, J=8.7 Hz, 2H, 2',6'-ArH), 7.79, 7.93 (2×s, 2H, 5-H, 8-H), 8.43 (d, J=3.6 Hz, 1H, pyr 6-H), 8.52 (s, 1H, pyr 2-H), 8.73 (t, J=5.9 Hz, 1H, CONH).; MS (FAB, m/z) 569,571 [(M+H)$^+$, 100%, 40% respectively; Cl isotopic pattern]. FAB-HRMS: measured 569.2403; calculated for $C_{32}H_{34}ClN_6O_2$ (M+H)$^+$: 569.2432.

EXAMPLE 4

4-[N-[7-Chloro-3-methyl-2-morpholinomethyl-4-oxo-3,4-dihydroquinazolin-6-ylmethyl]-N-(prop-2-ynyl)amino]-N-(3-pyridylmethyl)benzamide (CB 300925)

A solution of tert-butyl 4-[N-[7-chloro-3-methyl-2-morpholinomethyl-4-oxo-3,4-dihydroquinazolin-6-ylmethyl]-N-(prop-$^2$-ynyl)amino]benzoate (Preparation Example 17) (0.093 g, 0.173 mmol) in dichloromethane (1.2 ml) and trifluoroacetic acid (1.6 ml) was stirred at room temperature for 55 min. The solution was then concentrated in vacuo to an oily residue which was treated with toluene/dichloromethane. The solvents were then removed in vacuo and the residue was dried in vacuo over $P_2O_5$ to afford a pale yellow solid. This was dissolved in DMF (1.2 ml) under argon and the solution was placed in an ice-bath. A solution of 3-(aminomethyl)pyridine (0.028 g, 0.26 mmol) in anhydrous DMF (0.2 ml) was then added followed by PyBOP® (0.094 g, 0.182 mmol) and diisopropylethylamine (0.133 g, 1.03 mmol). After 5 min the ice-bath was removed and the reaction mixture was stirred at room temperature for an additional 3 h under argon. The solution was then partitioned between ethyl acetate (200 ml) and saturated aqueous sodium bicarbonate (100 ml) The organic layer was washed with more saturated aqueous sodium bicarbonate (100 ml), brine (100 ml), dried and concentrated in vacuo to an oily residue which was purified by column chromatography using a gradient of methanol in dichloromethane (2 to 5%) as eluant. The white solid was triturated with dichloromethane/hexanes (v/v, 1/1). The white solid was collected by filtration, washed with hexanes and dried in vacuo over $P_2O_5$ (0.066 g, 67%), mp>145° C. (it softens). $^1$H-NMR (DMSO-$d_6$) 2.55 (br s obscured, 4H, morpholine $CH_2NCH_2$), 3.19 (s, 1H, C≡CH), 3.56 (s(poorly resolved triplet), 4H, morpholine $CH_2OCH_2$), 3.63 (s, 3H, $N^3$-Me), 3.71 (s, 2H, 2-$CH_2$), 4.36 (s, 2H, $CH_2$C≡C), 4.45 (d, J=5.7 Hz, 2H, $CONHCH_2$), 4.77 (s, 2H, 6-$CH_2$), 6.79 (d, J=8.8 Hz, 2H, 3,5'-ArH), 7.32 (dd, J=4.8, 7.8 Hz, 1H, pyr 5-H), 7.68 (d, J=8.0 Hz, 1H, pyr 4-H), 7.75 (d, J=8.7 Hz, 2H, 2',6'-ArH), 7.79, 7.93 (2×s, 2H, 5-H, 8-H), 8.43 (d, J=3.4 Hz, 1H, pyr 6-H), 8.52 (s, 1H, pyr 2-H), 8.72 (t, J=5.9 Hz, 1H, CONH), MS (ESI, m/z) 571, 573 [(M+H)$^+$, 62%, 22% respectively; Cl isotopic pattern]. FAB-HRMS measured: 571.2240; calculated for $C_{31}H_{32}ClN_6O_3$ (M+H)$^+$ 571.2224.

Elemental Analysis: Found: C, 64.44; H, 5.75; N, 13.63; Cl 5.94. $C_{31}H_{31}ClN_6O_3$ 0.4AcOEt requires C, 64.58; H, 5.69; N, 13.86; Cl, 5.86%.

EXAMPLE 5

4-[N-[7-Chloro-3-methyl-2-pyrrolidinomethyl-4-oxo-3,4-dihydroquinazolin-6-ylmethyl]-N-(prop-2-ynyl)amino]-N-(3-pyridylmethyl)benzamide (CB 300926)

A solution of tert-butyl 4-[N-[7-chloro-3-methyl-2-pyrrolidinomethyl-4-oxo-3,4-dihydroquinazolin-6-ylmethyl]-N-(prop-2-ynyl)amino]benzoate (Preparation Example 18) (0.083 g, 0.16 mmol) in dichloromethane (1.1 ml) and trifluoroacetic acid (1.5 ml) was stirred at room temperature for 55 min with protection from the light. The solvent was removed in vacuo and the oily residue was dissolved in $CH_2Cl_2$/toluene, then concentrated in vacuo, and dried in vacuo over $P_2O_5$. The solid was then dissolved in anhydrous DMF (1.2 ml), cooled in an ice-bath and then a solution of 3-(aminometliyl)pyridine (0.026 g, 0.26 mmol) in anhydrous DMF (0.2 ml) was added followed by PyBOP® (0.087 g, 0.168 mmol) and diisopropylethylamine (0.123 g, 0.96 mmol). The reaction mixture was stirred at 0° C. for 5 min, then the ice-bath was removed, and stirring was continued for a longer 3 hours. The clear solution was then partitioned between ethyl acetate (200 ml) and saturated aqueous sodium bicarbonate (100 ml). The organic layer was washed with saturated aqueous sodium bicarbonate (100 ml), brine (100 ml), dried ($Na_2SO_4$) and concentrated in vacuo. The residue was purified by column chromatography using a gradient of methanol in dichloromethane (3 to 8%) as eluant. Pure by TLC fractions were combined, concentrated in vacuo, and the residue was treated with dichloromethane/hexanes. The solvent was removed in vacuo to give a white solid (0.061 g, 69%), mp 195–198° C.; $^1$H-NMR (DMSO-$d_6$) 1.70 (br s, 4H, pyrrolidine $CH_2CH_2$), 2.55 (br s 4H, pyrrolidine $CH_2NCH_2$), 3.19 (s, 1H, C≡CH), 3.60 (s, 3H, $N^3$-Me), 3.74 (s, 2H, 2-$CH_2$), 4.37 (s, 2H, $CH_2C≡C$), 4.45 (d, J=5.8 Hz, 2H, $CONHCH_2$), 4.77 (s, 2H, 6-$CH_2$), 6.80 (d, J=8.9 Hz, 2H, 3',5'-ArH), 7.32 (dd, J=4.9, 7.9 Hz, 1H, pyr 5-H), 7.68 (d, J=8.0 Hz, 1H, pyr 4-H), 7.75 (d, J=8.8 Hz, 2H, 2',6'-ArH), 7.79, 7.92 (2×s, 2H, 5-H, 8-H), 8.43 (d, J 3.2 Hz, 1H, pyr 6-H), 8.51 (s, 1H, pyr 2-H), 8.73 (t, J=5.9 Hz, 1H, CONH).

EXAMPLE 6

4-[N-[7-Chloro-3-methyl-2-(4-ethyl-piperazin-1-yl)methyl-4-oxo-3,4-dihydroquinazolin-6-ylmethyl]-N-(prop-2-ynyl)amino]-N-(3-yridylmethyl)benzamide (CB 300927)

A solution of tert-butyl 4-[N-[7-chloro-3-methyl-2-(4-ethyl-piperazin-1-yl)methyl-4-oxo-3,4-dihydrbquinazolin-6-ylmethyl]-N-(prop-2-ynyl)amino]benzoate (Preparation Example 19) (0.071 g, 0.126 mmol) in dichloromethane (0.8 ml) and trifluoroacetic acid (1.2 ml) was stirred at room temperature for 55 min with protection from the light. The trifluoroacetic acid was then removed in vacuo, and the residue was treated with dichloromethane/toluene, concentrated in vacuo to leave a white solid which dried in vacuo over $P_2O_5$ (0.114 g). This solid was dissolved in anhydrous DMF (1.3 ml) under argon. The solution was placed in an ice-bath and then a solution of 3-(aminomethyl)pyridine (0.020 g, 0.189 mmol) in anhydrous DMF (0.2 ml) was added followed by PyBOP® (0.069 g, 0. 132 mmol), and finally diisopropylethylamine (0.114 g, 0.88 mmol). The solution was stirred at 0° C. for 5 min., then the ice-bath was removed and stirring was continued under argon for 3 h. The clear solution was then partitioned between ethyl acetate (200 ml) and saturated aqueous sodium bicarbonate (100 ml). The organic layer was washed with more saturated aqueous sodium bicarbonate (100 ml), brine (100 ml), dried ($Na_2SO_4$) and concentrated in vacuo. Purification by column chromatography,.on gradient elution with methanol in dichloromethane (5 to 13%), afforded a white solid. Trituration with dichloromethane/hexaanes afforded a white solid which was suspended in water (5 ml). The pH of this suspension was first adjusted to 1 with 1N aqueous HCl to give a clear solution, then to ~12 with 1N NaOH, a white precipitate had obtained. The white solid was collected by filtration, washed with water, and dried in vacuo over $P_2O_5$ (0.040 g, 53%), mp 121–122° C.; $^1$H-NMR (DMSO-$d_6$) 0.96 (t, J=7.1 Hz, 3H, $CH_2CH_3$), 2.26 (q obscured, J=6.6 Hz, 2H, $CH_2CH_3$), 2.30 (br s) and 2.50 (br s obscured) (8H, $N(CH_2CH_2)_2$), 3.20 (s, 1H, C≡CH), 3.60 (s, 5H, $N^3$-Me, 2-$CH_2$), 4.37 (s, 2H, $CH_2C≡C$), 4.45 (d, J=5.7 Hz, 2H, $CONHCH_2$), 4.77 (s, 2H, 6-$CH_2$), 6.79 (d, J=8.8 Hz, 2H, 3',5'-ArH), 7.3 1 (dd, J=4.8, 7.8 Hz, 1H, pyr 5-H), 7.68 (d, J=7.8 Hz, pyr 4-H), 7.76 (d, J=8.7 Hz, 2H, 2',6'-ArH), 7.80, 7.91 (2×s, 2H, 5-H, 8-H), 8.43 (d, J=4.9 Hz, pyr 6-H), 8.72 (s, 1H, 2-H pyr), 8.72 (t, J=5.8 Hz, 1H, CONH).

MS (ESI, m/z) 598, 600 [(M+H)$^+$, 100%, 30% respectively; Cl isotopic pattern]; Elemental Analysis: Found: C, 65.23; H, 6.00; N, 16.04. $C_{33}H_{36}ClN_7O_2$ 0.5 $H_2O$ requires: C, 65.28; H, 6.14; N, 16.15.

EXAMPLE 7

4-[N-[7-Chloro-3-methyl-2-(methyl-L-prolin-1-yl)methyl-4-oxo-3,4-dihydroquinazolin-6-ylmethyl]-N-(prop-2-ynyl)amino]-N-(3-pyridylmethyl)benzamide (CB 300928)

A solution of tert-butyl 4-[N-[7-chloro-3-methyl-2-(methyl-L-prolin-1-yl)methyl-4-oxo-3,4-dihydroquinazolin-6-ylmethyl]-N-(prop-2-ynyl)amino]benzoate (Preparation Example 20) (0.090 g, 0.16 mmol) in dichloromethane (1.2 ml) and trifluoroacetic acid (1.6 ml) was stirred at room temperature for 1 h in the dark. The trifluoroacetic acid was then removed in vacuo, the residue was treated with ether and concentrated in vacuo to leave a white solid which dried in vacuo over $P_2O_5$. This solid was dissolved in anhydrous DMF (2.6 ml) under argon. The solution was placed in an ice-bath and then a solution of 3-(aminomethyl)pyridine (0.021 g, 0.215 mmol) in anhydrous DMF (0.4 ml) was added followed by PyBOP® (0.078 g, 0.150 mmol), and finally diisopropylethylamine (0.166 g, 1.29 mmol). The solution was stirred at 0° C. for 3 min, then the ice-bath was removed and stirring was continued under argon for 3 h. The solution was then partitioned between ethyl acetate (200 ml) and saturated aqueous sodium bicarbonate (100 ml). The organic layer was washed with more saturated aqueous sodium bicarbonate (100 ml), brine (50 ml), dried ($MgSO_4$) and concentrated in vacuo to afford a colourless glass. Purification by column chromatography, on gradient elution with methanol in chloroform (0 to 4%), afforded a colourless glass. Reprecipitation from chloroform/hexanes afforded a white solid which was collected by filtration, washed with hexanes and dried in vacuo over $P_2O_5$. This solid was suspended in water (5 ml), the pH adjusted to 1 with 1N HCl to give a clear solution, the pH then readjusted to 12 with 1N NaOH aqueous solution and the precipitate formed was removed by filtration and dried in vacuo over $P_2O_5$ to afford a white solid (0.025 g, 26%), mp 139° C. $^1$H-NMR (DMSO-d$_6$) 1.76 (m, 3H, proline N—CH$_2$—CH$_2$CH, 2.12 (m, 1H, proline N—CH$_2$CH$_2$—CH), 2.50 (m, 1H, (obscured by DMSO), proline-CH), 2.99 (m, 1H, proline-CH), 3.22 (s, 1H, HC≡C), 3.33 (m, 1H, (obscured by H$_2$O), proline N—CHCOOCH$_3$), 3.37 (s, 3H, COOCH), 3.62 (s, 3H, N$^3$-Me), 3.85 (AB system, J=13.1 Hz, 2H, 2-CH$_2$), 4.37 (s, 2H, CH$_2$C≡C), 4.45 (d, J=5.5 Hz, 2H, CONHCH$_2$), 4.77 (s, 2H, 6-CH$_2$), 6.78 (d, J=8.5 Hz, 2H, 3',5'-ArH), 7.33 (dd, J=4.9, 7.8 Hz, 1H, pyr-5H), 7.67 (d, J=7.6 Hz, 1H, pyr-4H), 7.75 (d, J=9.4 Hz, 2',6'-ArH), 7.77, 7.90 (2×s, 2H, 5-H, 8-H), 8.43 (d, J=4.2 Hz, 1H, pyr-6H), 8.51 (s, 1H, pyr-2H), 8.78 (t, J=6.0 Hz, 1H, CONH).

MS (FAB, m/z) 615, 613 [(M+H)$^+$, 60%, 25% respectively, Cl isotopic pattern]. Elemental Analysis: Found: C, 64.49; H, 5.28; N, 13.35. C$_{33}$H$_{33}$ClN$_6$O$_4$ requires: C, 64.55; H, 5.43; N, 13.71. FAB-HRMS; measured 613.2315; calculated for C$_{33}$H$_{34}$ClN$_6$O$_4$ (M+H)$^+$: 613.2330.

EXAMPLE 8

4-[N-[7-Chloro-3-methyl-2-(4-(2-hydroxyethyl)-piperazin-1-yl)methyl-4-oxo-3,4-dihydroquinazolin-6-ylmethyl]-N-(prop-2-ynyl)amino]-N-(3-pyridylmethyl)benzamide (CB300930)

A solution of tert-butyl 4-[N-[7-chloro-3-methyl-2-(4-(2-hydroxyethyl)ethyl-piperazin-1-yl)methyl-4-oxo-3,4-dihydroquinazolin-6-ylmethyl]-N-(prop-2-ynyl)amino] benzoate (0.157 g, 0.27 mmol) (Preparation Example 21) in dichloromethane (1.6 ml) and trifluoroacetic acid (2.6 ml) was stirred at room temperature for 55 min with protection from the light. The trifluoroacetic acid was then removed in vacuo, and the residue was treated with dichloromethane/toluene, concentrated in vacuo to leave an orange glass which was dried in vacuo over P$_2$O$_5$ (0.114 g). This was dissolved in anhydrous DMF (2.5 ml) under argon. The solution was placed in an ice-bath and then a solution of 3-(aminomethyl)pyridine (0.043 g, 0.40 mmol) in anhydrous DMF (1.5 ml) was added followed by PyBOP® (0.147 g, 0.28 mmol), and.finally diisopropylethylamine (0.209 g, 1.62 mmol). The solution was stirred at 0° C. for 5 min, then the ice-bath was removed and stirring was continued under argon for 3 h. The clear solution was then partitioned between ethyl acetate (200 ml) and saturated aqueous sodium bicarbonate (100 ml). The organic layer was washed with more saturated aqueous sodium bicarbonate (100 ml), brine (100 ml), dried (Na$_2$SO$_4$) and concentrated in vacuo. Purification by column chromatography, on gradient elution with methanol in dichloromethane (5 to 15%), afforded a glass. This was suspended in water (6 ml) and the pH was first adjusted to 1 with 1N aqueous HCl to give a clear solution, then to ~9 with 1N NaOH; a pale yellow precipitate was obtained. The solid was collected by filtration, washed with water, and dried in vacuo over P$_2$O$_5$ (6.065 g, 40%), mp 115–117° C.; $^1$H-NMR (DMSO-d6) 2.35 (t obscured, J=6.3 Hz, 2H, NCH$_2$CH$_2$OH), 2.38, 2.46 (2×br s, 8H, N(CH$_2$CH$_2$)$_2$), 3.18 (s, 1H, C≡CH), 3.46 (q, J=6.1 Hz, 2H, NCH$_2$CH$_2$OH), 3.60 (s, 5H, N$^3$-Me, 2-CH$_2$), 4.26 (t, J=5.3 Hz, 1H, NCH$_2$CH$_2$ OH), 4.36 (d, J=1.8 Hz, 2H, CH$_2$C≡C), 4.45 (d, J=5.8 Hz, 2H, CONHCH$_2$), 4.77 (s, 2H, 6-CH$_2$), 6.79 (d, J=8.9 Hz, 2H, 3',5'-ArH), 7.33 (dd, J=4.8, 7.8 Hz, 1H, pyr 5-H), 7.69 (dt, J=1.8, 7.8 Hz, pyr 4-H), 7.76 (d, J=8.8 Hz, 2H, 2',6'-ArH), 7.80, 7.91 (2×s, 2H, 5-H, 8-H), 8.43 (dd, J=1.6, 4.8 Hz, 1H, pyr 6-H), 8.52 (s, 1H, 2-H pyr), 8.72 (t, J=5.8 Hz, 1H, CONH).

MS (ESI, m/z) 614, 616 [(M+H)$^+$; 100%, 35% respectively, Cl isotopic pattern]; Elemental Analysis: Found: C, 63.10; H, 5.86; N, 15.56; Cl, 5.97%. C$_{33}$H$_{36}$ClN$_7$O$_3$ 0.7 H$_2$O requires: C, 63.24; H, 6.01; N, 15.64; Cl, 5.65%.

EXAMPLE 9

4-[N-[7-Chloro-3-methyl-4-oxo-2-(4-phenylpiperazin-1-yl)methyl-3,4-dihydroquinazolin-6-ylmethyl]-N-(prop-2-ynyl)amino]-N-(3-pyridylmethyl)benzamide (CB300934)

A solution of tert-butyl 4-[N-[7-chloro-3-methyl-4-oxo-2-(4-phenylpiperazin-1-yl)methyl-3,4-dihydroquinazolin-6-ylmethyl]-N-(prop-2-ynyl)amino]benzoate (0.140 g, 0.23 mmol) (Preparation Example 22) in dichloromethane (1.7 ml) and trifluoroacetic acid (2.3 ml) was stirred at room temperature for 55 min with protection from the light. The trifluoroacetic acid was then removed in vacuo, and the residue was treated with dichloromethane/toluene, concentrated in vacuo, and dried in vacuo over P$_2$O$_5$ (0.182 g). This was dissolved in anhydrous DMF (2 ml) under argon. The solution was placed in an ice-bath and then a solution of 3-(aminomethyl)pyridine (0.037 g, 0.34 mmol) in anhydrous DMF (0.2 ml) was added followed by PyBOP® (0.125 g, 0.24 mmol), and finally diisopropylethylamine (0.178 g, 1.38 mmol). The solution was stirred at 0° C. for 5 min, then the ice-bath was removed and stirring was continued under argon for 3 h. The clear solution was then partitioned between ethyl acetate (150 ml) and saturated aqueous sodium bicarbonate (100 ml). The organic layer was washed with more saturated aqueous sodium bicarbonate (100 ml), brine (100 ml), dried (Na$_2$SO$_4$) and concentrated in vacuo. Purification by column chromatography, on gradient elution with methanol in dichloromethane (2 to 5%), afforded a white solid which was reprecipitated from dichloromethane/hexanes (0.104 g, 71%), mp 214–216° C. $^1$H-NMR (DMSO-d$_6$) 2.76 (br s) and 3.11 (br s) (8H, N(CH$_2$CH$_2$)$_2$), 3.20 (s, 1H, C≡CH), 3.63 (s, 3H, N$^3$-Me), 3.70 (s, 2H, 2-CH$_2$), 4.37 (s, 2H, CH$_2$C≡C), 4.45 (d, J 5.7 Hz, 2H, CONHCH$_2$), 4.78 (s, 2H, 6-CH$_2$), 6.74 (t obscured, 1H), 6.90 (d, J=8.6 Hz, 2H), and 7.20 (t, J=8.20 Hz, 2H) (C$_6$H$_5$—N(CH$_2$CH$_2$)$_2$N—), 6.76 (d, J=8.7 Hz, 2H, 3,5'-ArH), 7.32 (dd, J=4.6, 7.8 Hz, 1H, pyr 5-H), 7.68 (d, J=7.7 Hz, pyr 4-H), 7.75 (d, J=8.6 Hz, 2H, 2',6'-ArH), 7.83, 7.93 (2×s, 2H, 5-H, 8-H), 8.43 (d, J=4.7 Hz, pyr 6-H), 8.52 (s, 1H, pyr 2-H), 8.76 (t, J=5.8 Hz, 1H, CONH).

MS (ESI, m/z) 646, 648 [(M+H)$^+$, 100%, 40% respectively; Cl isotopic pattern]; Elemental Analysis: Found: C, 69.11; H, 5.90; N, 14.78; Cl, 5.36%. C$_{37}$H$_{36}$ClN$_7$O$_2$ requires: C, 68.77; H, 5.62; N, 15.17; Cl, 5.49%.

EXAMPLE 10

4-[N-[7-Chloro3-methyl-2-(4-hydroxypiperidin-1-yl)methyl-4-oxo-3,4-dihydroquinazolin-6ylmethyl]-N-(prop-2-ynyl)amino]-N-(3-pyridylmethyl)benzamide (CB300939)

A solution of tert-butyl 4-[N-[7-chloro-3-methyl-2-(4-hydroxypiperidin-1-yl)methyl-4-oxo-3,4-dihydroquinazolin-6-ylmethyl]-N-(prop-2-ynyl)amino] benzoate (0.158 g, 0.28 mmol) (Preparation Example 23) in dichloromethane (2 ml) and trifluoroacetic acid (2.5 ml) was stirred at room temperature for 1 hour with protection from the light. The solvents were then removed in vacuo and the residue was treated with toluene/dichloromethane, concentrated in vacuo and the residue was dried in vacuo over P$_2$O$_5$. This material was dissolved in anhydrous DMF (2.5 ml) under argon and the solution was placed in an ice-bath. A solution of 3-(aminomethyl)pyridine (0.045 g, 0.42 mmol) in DMF (0.4 ml) was then added followed by PyBOP® (0.152 g, 0.29 mmol) and diisopropylethylamine (0.210 g, 1.68 mmol). Stirring was continued at 0° C. for 5 min; then the ice-bath was removed and the reaction mixture was stirred for an additional 4 h before being partitioned between ethyl acetate (150 ml) and saturated aqueous sodium bicarbonate (100 ml). The organic layer was washed with more saturated aqueous sodium bicarbonate (100 ml) and brine (100 ml). The aqueous washings were extracted with ethyl acetate (100 ml), dried ($Na_2SO_4$) and concentrated in vacuo. The residue was purified by column chromatography using a gradient of methanol in chloroform (5 to 10%) to afford a white solid. This was suspended in water (6 ml) and the pH was first adjusted to ~1 with 1N HCl, then to ~10 with 1N NaOH; a white precipitate was obtained. The white solid was collected by filtration, washed with water and dried in vacuo over $P_2O_5$ (0.102 g, 63%), mp 134–136° C.; $^1$H-NMR (DMSO-$d_6$), 1.37 (m, 2H), 1.70 (m, 2H), 2.21 (m, 2H), 2.70 (m, 2H), and 3.46 (m, 1H) (piperidine ring protons), 3.20 (s, 1H, C≡CH), 3.60 (s, 5H, $N^3$-Me, 2-$CH_2$), 4.38 (s, 2H, $CH_2$C≡C), 4.45 (d, J=5.8 Hz, 2H, CONH$CH_2$), 4.77 (s, 2H, 6-$CH_2$), 6.78 (d, J=8.8 Hz, 2H, 3',5'-ArH), 7.33 (dd, J=4.6, 7.6 Hz, 1H, pyr 5-H), 7.68 (d, J=7.8 Hz, 1H, pyr 4-H), 7.76 (d, J=8.8 Hz, 2H, 2',6'-ArH), 7.81, 7.91 (2×s, 2H, 5-H, 8-H), 8.43 (d, J=4.0 Hz, 1H, pyr 6-H), 8.52 (s, 1H, pyr 2-H), 8.73 (t, J=5.3 Hz, 1H, CONH).; MS (ESI, m/z) 585,587 [(M+H)$^+$, 100%, 37% respectively; Cl isotopic pattern].

Elemental Analysis: Found: C, 63.35; H, 5.50; N, 13.68. $C_{32}H_{33}ClN_6O_3$ $H_2O$ requires: C, 63.73; H, 5.84; N, 13.93%.

EXAMPLE 11

4-[N-[7-Chloro-3-methyl-2-(4-methyl-piperazin-1-yl)methyl-4-oxo-3,4-dihydroquinazolin-6-ylmethyl]-N-(prop-2-ynyl)amino]-N-[3-(1H-imidazol-1-yl)propyl)benzamide (CB300929)

A solution of tert-butyl 4-[N-[7-chloro-3-methyl-2-(4-methyl-piperazin-1-yl)methyl-4-oxo-3,4-dihydroquinazolin-6-ylmethyl]-N-(prop-2-ynyl)amino]benzoate (0.082 g, 0.15 mmol) (Preparation Example 14) in dichloromethane (1.2 ml) and trifluoroacetic acid (1.6 ml) was stirred at room temperature for 55 min. The solvents were then removed in vacuo, and the residue was treated with dichloromethane/toluene, concentrated in vacuo to leave a pale yellow solid which was dried in vacuo over $P_2O_5$. This solid was dissolved in anhydrous DMF (1.8 ml) under argon. The solution was placed in an ice-bath and then a solution of 1-(3-(aminopropyl)imidazole (0.029 g, 0.23 mmol) in anhydrous DMF (0.2 ml) was added followed by PyBOP® (0.083 g, 0.16 mmol), and finally diusopropyl-ethylamine (0.135 g, 1.05 mmol). The solution was stirred at 0° C. for 5 min, then the ice-bath was removed and stirring was continued under argon for 2.5 h. The clear solution was then partitioned between ethyl acetate (150 ml) and saturated aqueous sodium bicarbonate (80 ml). The organic layer was washed with more saturated aqueous sodium bicarbonate (80 ml), brine (80 ml), dried ($Na_2SO_4$) and concentrated in vacuo. Purification by column chromatography, on gradient elution with methanol in chloroform (15 to 20%), afforded a white solid. This was suspended in water (6 ml) and the pH was first adjusted to ~1 with 0.5N HCl and then to ~12 with 1N NaOH. The white solid was collected by filtration, washed with water, and dried in vacuo over $P_2O_5$ (0.036 g, 40%), mp>115° C. (softens); $^1$H-NMR (DMSO-$d_6$) 1.91 (m, 2H, CONH$CH_2CH_2CH_2$), 2.14 (s, 3H, N-Me piperazine), 2.30 (br s) and 2.49 br s (obscured)) (8H, N($CH_2CH_2$)$_2$N—), 3.18 (m, 2H, CONH$CH_2CH_2CH_2$), 3.20 (s, 1H, C≡CH), 3.59, 3.61 (2×s, 5H, $N^3$-Me and 2-$CH_2$), 3.98 (t, J=6.84 Hz, 2H, CONH$CH_2CH_2CH_2$) 4.37 (s, 2H, $CH_2$C≡C), 4.76 (s, 2H, 6-$CH_2$), 6.78 (d, J=8.5 Hz, 2H, 3,5'-ArH), 6.88, 7.19 (2×s, 2H, imidazole 4-H and 5-H), 7.64 (s, 1H, imidazole 2-H), 7.71 (d, J=8.2 Hz, 2H, 2',6'-ArH), 7.81, 7.91 (2×s, 2H, 5-H, 8-H), 8.17 (t, J=5.0 Hz, 1H, CONH).

MS (ESI, m/z) 601, 603 [(M+H)$^+$, 70%, 25% respectively; Cl isotopic pattern]; FAB-HRMS: measured: 601.2789; calculated for $C_{32}H_{38}ClN_8O_2$ (M+H)$^+$: 601.2806.

EXAMPLE 12

4-[N-[7-Chloro-3-methyl-4-oxo-2-(piperidin-1-yl) methyl-3,4-dihydroquinazolin-6-ylmethyl]-N-(prop-2-ynyl)amino]-N-[(3-(1H-1,2,4-triazol-1-yl)propyl] benzamide (CB300942)

To a solution of tert-butyl 4-[N-[7-chloro-3-methyl-2-(piperidin-1-yl)methyl-4-oxo-3,4-dihydroquinazolin-6-ylmethyl]-N-(prop-2-ynyl)amino]benzoate (0.075 g, 0.14 mmol) (Preparation Example 16) in dichloromethane (1 ml) was added trifluoroacetic acid (1.5 ml). The clear solution was stirred at room temperature for 55 min then the solvent was removed in vacuo. The remaider was treated with dichloromethane/toluene, the solvents was removed in vacuo and the residue was dried in vacuo over $P_2O_5$. This material was dissolved in anhydrous DMF (1.2 ml) and the solution cooled in an ice-bath. A solution of 1-(3-aminopropyl)-1,2,4-triazole (W. B. Wright et al. *J. Med. Chem* 1986, 29, 523–530; 0.026 g, 0.21 mmol) in anhydrous DMF (0.2 ml) was then added followed by PyBOP® (0.078 g, 0.15 mmol) and diisopropylethylamine (0.14 ml, 0.8 mmol). Stirring was continued at 0° C. of 3 min; then the ice-bath was removed and stirring was continued for a further 3 hours. The reaction mixture was then partitioned between ethyl acetate (150 ml) and saturated aqueous sodium bicarbonate (80 ml). The two layers were separated and the aqueous layer was extracted with ethyl acetate (100 ml). The combined ethyl acetate extracts were washed with saturated aqueous bicarbonate (50 ml), brine (2×50 ml), dried ($Na_2SO_4$) and concentrated in vacuo. Purification by column chromatography on elution with 5% methanol in dichloromethane afforded a solid which was reprecipitated from ethyl acetate/hexane. This solid was suspended in water (4 ml) and the pH was first adjusted to ~1 with 1N HCl and then to ~11 with 1N NaOH. The white precipitate was collected by filtration washed with water and dried in vacuo over $P_2O_5$ (0.044 g, 54%), mp 103–105° C.; $^1$H-NMR (DMSO-$d_6$) 1.45 (m, 6H, piperidine $CH_2CH_2CH_2$), 1.99 (m, 2H, CONH$CH_2CH_2CH_2$), 2.41 (br s, 4H, piperidine $CH_2NCH_2$), 3.18 (m, 3H, CONH$CH_2$ and C≡CH), 3.56 (s, 2H, 2-$CH_2$), 3.60 (s, 3H, $N^3$-Me), 4.20 (t, J=6.8 Hz, 2H, $CH_2$-triazole), 4.36 (s, 2H, $CH_2$C≡C), 4.75 (s, 2H, 6-$CH_2$), 6.76 (d, J=8.8 Hz, 2H, 3',5'-ArH), 7.70 (d, J=8.8 Hz, 2H, 2',6'-ArH), 7.80, 7.94 (2×s, 2H, 5-H, 8-H), 7.90 (s, 1H, triazole 5-H), 8.20 (t, J=5.6 Hz, 1H, CONH), 8.51 (s, 1H, triazole 3-H); MS (ESI, m/z) 587,589 [(M+H)$^+$, 100%, 37% respectively; Cl isotopic pattern].

Elemental Analysis: Found C, 62.74; H, 5.95; N, 18.84; Cl, 5.98 $C_{31}H_{35}ClN_8O_2$×0.25 $H_2O$ requires: C, 62.94; H, 6.05; N, 18.94; Cl, 5.99%

EXAMPLE 13

4-[N-[7-Chloro-3-diethylcarbamoylmethyl-4-oxo-2-(piperidin-1-yl)methyl-3,4-dihydroquinazolin-6-ylmethyl]-N-(prop-2-ynyl)amino]-N-(3-pyridylmethyl)benzamide (CB300941)

A solution of tert-butyl 4-[N-[7-chloro-3-diethylcarbamoylmethyl-4-oxo-2-(piperidin-1-yl)methyl-3, 4-dihydroquinazolin-6-ylmethyl]-N-(prop-2-ynyl)amino] benzoate (0.065 g, 0.10 mmol) (Preparation Example 29) in dichloromethane (1 ml) and trifluoroacetic acid (1.3 ml) was stirred at room temperature for 1 hour with protection from the light. The solvent was then removed in vacuo and the remainder was treated with toluene/dichloromethane, concentrated in vacuo and the residue was dried in vacuo over $P_2O_5$. This material was dissolved in anhydrous DMF (1.3 ml) under argon and the solution was placed in.an ice-bath. A solution of 3-(aminomethyl)pyridine (0.016 g, 0.15 mmol) in DMF (0.3 ml) was then added followed by PyBOP® (0.055 g, 0.10 mmol) and diusopropylethylamine (0.077 g, 0.60 mmol). Stirring was continued at 0° C. for 3 min; then the ice-bath was removed and the reaction mixture was stirred for an additional 3 hours before being partitioned between ethyl acetate (100 ml) and saturated aqueous bicarbonate (80 ml). The aqueous layer was extracted with more ethyl acetate (2×50 ml). The combined organic extracts were washed With brine (80 ml), dried ($Na_2SO_4$) and concentrated in vacuo. The residue was purified by column chromatography using a gradient of methanol in dichloromethane (2 to 5%). The product was reprecipitated from dichloromethane/hexanes to give a white solid. This was suspended in water (5 ml) and the pH was first adjusted to ~1 with 1N HCl, then to ~11 with 1N NaOH; a white precipitate was obtained. This was collected by filtration, washed with water and dried in vacuo over $P_2O_5$ (0.040 g, 60%), mp>105° C.; $^1$H-NMR (DMSO-$d_6$), 1.00, 1.18 (2×t, 6H, 2×$CH_2CH_3$), 1.40 (br s, 6H, piperidine $CH_2CH_2CH_2$), 2.32 (br s, 4H, piperidine $CH_2NCH_2$), 3.24, 3.40 (2×q obscured by water peak, 4H, 2×$CH_2CH_3$), 4.37 (s, 2H, $CH_2C\equiv C$), 4.43 (d, J=5.6 Hz, 2H, $CONHCH_2$), 4.77 (s, 2H, 6-$CH_2$), 5.10 (s, 2H, $N^3$—$CH_2$), 6.77 (d, J=8.8 Hz, 2H, 3,5'-ArH), 7.31 (dd, J=4.8, 7.8 Hz, 1H, pyr 5-H), 7.67 (d, J=7.8 Hz, 1H, pyr 4-H), 7.73 (d, J=8.6 Hz, 2H, 2',6'-ArH), 7.83, 7.86 (2×s, 2H, 5-H, 8-H), 8.42 (d, J=3.2 Hz, 1H pyr 6-H), 8.52 (s, 1H, pyr 2-H), 8.73 (t, J=5.6 Hz, 1H, CONH).; MS (ESI, m/z) 668, 670 [(M+H)$^+$, 100%, 37% respectively; Cl isotopic pattern].

Elemental Analysis: Found: C, 64.96; H, 6.17; N, 14.27. $C_{37}H_{42}ClN_7O_3$ $H_2O$ requires: C, 64.76; H, 6.31; N, 14.28%.

EXAMPLE 14

4-[N-[7-Chloro-4-oxo-2-(piperidin-1-yl)methyl-3-piperidinocarbonylmethyl-3,4-dihydroquinazolin-6-ylmethyl]-N-(prop-2-ynyl)amino]-N-(3-pyridylmethyl)benzamide (CB300938)

A solution of tert-butyl 4-[N-[7-chloro-4-oxo-2-(piperidin-1-yl)methyl-3-piperidinocarbonylmethyl-3,4-dihydroquinazolin-6-ylmethyl]-N-(prop-2-ynyl)amino] benzoate (0.084 g, 0.13 mmol) (Preparation Example 30) in dichloromethane (1 ml) and trifluoroacetic acid (1.3 ml) was stirred at room temperature for 1 hour with protection from the light. The solvent was then removed in vacuo and the remainder was treated with toluene/dichloromethane, concentrated in vacuo and the residue was dried in vacuo over $P_2O_5$. This material was dissolved in anhydrous DMF (1.2 ml) under argon and the solution was placed in an ice-bath.

A solution of 3-(aminomethyl)pyridine (0.021 g, 0.19 mmol) in DMF (0.2 ml) was then added followed by PyBOP® (0.071 g, 0.14 mmol) and diisopropylethylamine (0.101 g, 0.78 mmol). Stirring was continued at 0° C. for 3 min; then the ice-bath was removed and the reaction mixture was stirred for an additional 4 h before being partitioned between ethyl acetate (150 ml) and saturated aqueous sodium bicarbonate (50 ml). The aqueous layer was extracted with more ethyl acetate (2×50 ml). The combined organic extracts were washed with brine (80 ml), dried ($Na_2SO_4$) and concentrated in vacuo. The residue was purified by column chromatography using a gradient of methanol in dichloromethane (3 to 5%). The product was reprecipitated from ethyl acetate/hexanes to give a white solid (0.038 g, 43%), mp 128–130° C.; $^1$H-NMR (DMSO-$d_6$), 1.30–1.70 (m, 12H), 2.36 (br s, 4H) and 3.40 (m, 4H), (piperidine protons), 3.20 (s, 1H, $C\equiv CH$), 3.47 (s, 2H, 2-$CH_2$), 4.37 (s, 2H, $CH_2C\equiv C$), 4.44 (d, J=5.8 Hz, 2H, $CONHCH_2$), 4.78 (s, 2H, 6-$CH_2$), 5.09 (s, 2H, $N^3$—$CH_2$), 6.78 (d, J=8.9 Hz, 2H, 3,5'-ArH), 7.32 (dd, J=4.8, 7.8 Hz, 1H, pyr 5-H), 7.68 (d, J=7.9 Hz, 1H, pyr 4-H), 7.75 (d, J=8.8 Hz, 2H, 2',6'-ArH), 7.82, 7.89 (2×s, 2H, 5-H, 8-H), 8.43 (dd, J=1.4, 4.6 Hz, 1H, pyr 6-H), 8.52 (d, J=1.6 Hz, 1H, pyr 2-H), 8.74 (t, J=5.9 Hz, 1H, CONH).; MS (ESI, m/z) 680, 682 [(M+H)$^+$, 100%, 37% respectively; Cl isotopic pattern].

Elemental Analysis: Found: C, 65.84; H, 6.69; N, 10.42. $C_{36}H_{44}ClN_5O_4$ $0.5H_2O$ requires: C, 65.99; H, 6.92; N, 10.68%.

EXAMPLE 15

4-[N-[7-Chloro-3-methoxycarbonylmethyl-4-oxo-2-piperidin-1-ylmethyl-3,4-dihydroquinazolin-6-ylmethyl]-N-(prop-2-ynyl)amino]-N-(3-pyridylmethyl)benzamide (CB300931)

A solution of tert-butyl 4-[N-[7-chloro-3-methoxycarbonylmethyl-4-oxo-2-piperidin-1-ylmethyl-3,4-dihydroquinazolin-6-ylmethyl]-N-(prop-2-ynyl)amino] benzoate (0.087 g, 0.14 mmol) (Preparation Example 31) in dichloromethane (1.7 ml) and trifluoroacetic acid (2.3 ml) was stirred at room temperature for 55 min with protection from the light. The solvents was then removed in vacuo and the residue was triturated with ether and dried in vacuo over $P_2O_5$. This solid was dissolved in anhydrous DMF (5 ml) under argon and the solution was placed in an ice-bath. A solution of 3-(aminomethyl)pyridine (0.024 g, 0.22 mmol) in DMF (0.2 ml) was then added followed by PyBOP® (0.082 g, 0.16 mmol) and dilsopropylethylamine (0.171 g, 1.3 mmol). Stirring was continued at 0° C. for 3 min; then the ice-bath was removed and the reaction mixture was stirred for an additional 3 h at room temperature before being partitioned between ethyl acetate (200 ml) and saturated aqueous bicarbonate (100 ml). The organic layer was washed with more saturated aqueous bicarbonate (100 ml) and the combined aqueous washings were extracted with ethyl acetate (2×50 ml). The combined ethyl acetate extracts were washed with brine (100 ml), dried ($Na_2SO_4$) and concentrated in vacuo. The residue was purified by column chromatography using a gradient of methanol in chloroform (0 to 3%) as eluant, then reprecipitated from dichloromethane/hexane to give a white solid which was collected by filtration, washed with hexane and dried in vacuo over $P_2O_5$ (0.036 g, 39%), mp 214–216° C.; $^1$H-NMR (DMSO-$d_6$) 1.36 (m, 6H, piperidine $CH_2CH_2CH_2$), 2.32 (m, 4H, piperidine $CH_2NCH_2$), 3.20(s, 1H, C≡CH), 3.58 (s, 2H, 2-$CH_2$), 3.67 (s, 3H, $CO_2Me$), 4.38 (s, 2H, CH,C≡C), 4.45 (d, J=5.7 Hz, 2H, $CONHCH_2$), 4.78 (s, 2H, 6-$CH_2$), 4.87(s, 2H, $N^3$—$CH_2$), 6.79 (d, J=8.8 Hz, 2H, 3,5'-ArH), 7.32 (dd, J=4.6, 7.8 Hz, 1H, pyr 5-H), 7.68 (d, J=7.7 Hz, 1H, pyr 4-H), 7.75 (d, J=8.7 Hz, 2H, 2',6'-ArH), 7.85, 7.91 (2×s, 2H, 5-H, 8-H), 8.43 (d, J=3.6 Hz, 1H, pyr 6-H), 8.52 (s, 1H, pyr 2-H), 8.74 (t, J=5.9 Hz, 1H, CONH).; MS (FAB, m/z) 627, 629 [(M+H)$^+$, 100%, 38% respectively; Cl isotopic pattern]. FAB-HRMS: measured 627.2504; calculated for $C_{34}H_{36}ClN_6O_2$ (M+H)$^+$: 627.2487.

Elemental Analysis: Found: C, 63.48; H, 5.33; N, 12.92; $C_{34}H_{35}ClN_6O_4$ 0.7$H_2O$ requires: C, 63.83; H, 5.73; N, 13.14%.

EXAMPLE 16

4-[N-[7-Chloro-3-(2-dimethylaminoethyl)-4-oxo-2-piperidin-1-ylmethyl-3,4-dihydroquinazolin-6-ylmethyl]-N-(prop-2-ynyl)amino]-N-(3-pyridylmethyl)benzamide (CB300933)

A solution of tert-butyl 4-[N-[7-chloro-3-(2-dimethylaminoethyl)-4-oxo-2-piperidin-1-ylmethyl-3,4-dihydroquinazolin-6-ylmethyl]-N-(prop-2-ynyl)amino] benzoate (0.100 g, 0.17 mmol) (Preparation Example 32) in dichloromethane (2.5 ml) and trifluoroacetic acid (3.5 ml) was stirred at room temperature for 55 min with protection from the light. The solvent was then removed in vacuo and the residue was triturated with ether and dried in vacuo over $P_2O_5$. This solid was dissolved in anhydrous DMF (5 ml) under argon and the solution was placed in an ice-bath. A solution of 3-(aminomethyl)pyridine (0.027 g, 0.25 mmol) in DMF (0.2 nil) was then added followed by PyBOP® (0.092 g, 0.37 mmol) and diisopropylethylamine (0.197 g, 1.53 mmol). Stirring was continued at 0° C. for 15 min; then the ice-bath was removed and the reaction mixture was stirred for an additional 4 h at room temperature. The solvent was then removed in vacuo and the residue was chromatographed on aluminium oxide 90 active (neutral) column eluting first with chloroform and then with 1% methanol in chloroform. The product was obtained as a white solid (0.026 g, 24%), mp 90–93° C.; $^1$H-NMR (DMSO-$d_6$) 1.40–1.49 (m, 6H, piperidine $CH_2CH_2CH_2$), 2.20 (s, 6H, $Me_2N$) 2.41 (m, 4H, piperidine $CH_2NCH_2$), 2.55 (t (obscured), 2H, $Me_2NCH_2$), 3.21(s, 1H, C≡CH), 3.62 (s, 2H, 2-$CH_2$), 4.25 (t, J=7.0 Hz, 2H, $N^3$-$CH_2$), 4.38 (s, 2H, $CH_2$C≡C), 4.45 (d, J=5.7 Hz, 2H, CONHCH 4.78 (s, 2H, 6-$CH_2$), 6.78 (d, J=8.8 Hz, 2H, 3,5'-ArH), 7.32 (dd, J=4.8, 7.8 Hz, 1H, pyr 5-H), 7.68 (d, J=8.0 Hz, 1H, pyr 4-H), 7.75 (d, J=8.7 Hz, 2H, 2',6'-ArH), 7.85, 7.91 (2×s, 2H, 5-H, 8-H), 8.43 (d, J=5.1 Hz, 1H, pyr 6-H), 8.52 (s, 1H, pyr 2-H), 8.74 (t, J=5.9 Hz, 1H, CONH).; MS (FAB, m/z) 626, 628 [(M+H)$^+$, 100%, 35% respectively; Cl isotopic pattern]. FAB-HRMS: measured 626.3025; calculated for $C_{35}H_{41}ClN_7O_2$ (M+H)$^+$: 626.3010.

EXAMPLE 17

4-[N-[3-Methyl-4-oxo-2-(piperidin-1-yl)methyl-3,4,7,8-tetrahydro-6H-cyclopenta[g]quinazolin-6-yl]-N-methylaminol-N-(3-pyridylmethyl)benzamide A solution of tert-butyl 4-[N-[3-methyl-4-oxo-2-(piperidin-1-yl)methyl-3,4,7,8-tetrahydro-6H-cyclopenta[g] quinazolin-6-yl]-N-methylamino]benzoate (Preparation Example 42) (0.050 g, 0.1 mmol) and trifluoroacetic acid (1 ml) in dichloromethane (1 ml) was stirred at room temperature for 1 hour after which time the reaction mixture was concentrated under reduced pressure with the trifluoroacetic acid being azeotoped off with toluene. The residue was dried over $P_2O_5$ under vacuum to afford the title compound (0.045 g, 100%). MS (ESI, m/z) 447 [(M+H)$^+$100%]. To a solution of this material (0.045 g, 0.1 mmol) in anhydrous DMF (1.5 ml) was added a solution of 3-(aminomethyl)pyridine (0.016 g, 0.15 mmol) in anhydrous DMF (0.2 ml) at 0° C. followed by PyBOP® (0.055 g, 0.105 mmol) and diisopropylethylamine (0.1 ml, 0.57 mmol). The solution was kept at 0° C. for 1 hour and then allowed to warm to room temperature and stirred at that temperature for a further 2 hours. The reaction mixture was then partitioned between a saturated aqueous solution of sodium bicarbonate (40 ml) and ethyl acetate (40 ml) and the aqueous phase was re-extracted with more ethyl acetate (2×20 ml). The combined organic extracts were successively washed with a saturated aqueous solution of sodium bicarbonate (20 ml), brine (20 ml), then dried ($Na_2SO_4$) and concentrated under reduced pressure.

Flash column chromatography with methanol-dichloromethane (1:20 then 1:10 v/v) afforded a white solid (0.045 g) which was dissolved in 1M HCl (pH 1). The pH was then adjusted to 11 with 1M NaOH, the suspension was filtered, washed with water (5 ml) and the precipitate dried over $P_2O_5$ under vacuum to afford the title compound (0.026 g, 50%); $^1$H NMR (CDCl$_3$) 1.45 (m), 1.54 (m) (6H, d, piperidine $CH_2CH_2CH_2$), 2.09 (m, 1H, 7-CH), 2.49 (m, 5H, 7-CH and piperidine $CH_2NCH_2$),. 2.72 (s, 3H, $N^{10}$-Me), 3.07 (m, 2H, 8-$CH_2$), 3.56 (AB system J=1.0 Hz, 2H, 2-$CH_2$), 3.76 (s, 3H, 3-Me), 4.63 (d, 2H, J=5.8 Hz, CONH$CH_2$), 5.63 (t, 1H, J=8.1 Hz), 6.85 (d, 2H, J=8.9 Hz, 3,'5'- ArH), 7.24 (dd, 1H, J=4.8, 7.8 Hz, pyr 5-H), 7.54 (s, 1H, 9-H), 7.72 (m, 1H, pyr 4-H), 7.76 (d, 2H, J=8.9 Hz, 2',6'-ArH), 8.03 (s, 1H, 5-H), 8.49 (dd, 1H, J=1.6, 4.8 Hz, pyr 6-H), 8.57 (d, 1H, J=1.8 Hz, pyr 2-H); MS (ESI, m/z) 537 [(M+H)$^+$100%].

EXAMPLE 18

Compounds of the invention were compared with the compounds CB 30865 and CB 300847. The structure of these comparative compounds and the compounds of Examples 1 to 17 are given in the Table A below.

TABLE A

[General structure: quinazolinone core with R2 on N3, R3 at C2, R5 at C7, with CH2-N(propargyl)-C6H4-C(O)NH-(CH2)m-R7 substituent at C6]

| CB No. | | |
|---|---|---|
| 300847 (Comparative) | | [structure: N-methyl isoquinolinone fused to cyclopentane, with N(propargyl)-C6H4-C(O)NH-CH2-(3-pyridyl)] |
| 30865 (Comparative) | | [structure: 2-methyl-7-bromo-quinazolin-4(3H)-one-6-CH2-N(propargyl)-C6H4-C(O)NH-CH2-(3-pyridyl)] |

| | R₂ | R₃ | R₅ | m | R₇ |
|---|---|---|---|---|---|
| 300919 (Example 1) | CH₃— | CH₃—N(piperazine)N—CH₂— | Cl | 1 | 3-pyridyl |
| 300921 (Example 1) | CH₃— | CH₃—N(piperazine)N—CH₂— · HCl | Cl | 1 | 3-pyridyl |
| 300922 (Example 2) | CH₃— | (C₂H₅)₂—NCH₂— | Cl | 1 | 3-pyridyl |
| 300923 (Example 3) | CH₃— | piperidin-1-yl—CH₂— | Cl | 1 | 3-pyridyl |
| 300925 (Example 4) | CH₃— | morpholin-4-yl—CH₂— | Cl | 1 | 3-pyridyl |
| 300926 (Example 5) | CH₃— | pyrrolidin-1-yl—CH₂— | Cl | 1 | 3-pyridyl |
| 300927 (Example 6) | CH₃— | C₂H₅—N(piperazine)N—CH₂— | Cl | 1 | 3-pyridyl |

TABLE A-continued
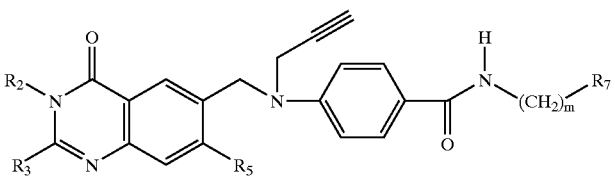
| CB No. | $R_2$/$R_3$ | (middle group) | $R_5$ | m | $R_7$ |
|---|---|---|---|---|---|
| 300928 (Example 7) | CH$_3$— | 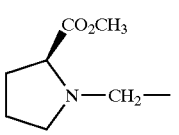 | Cl | 1 | 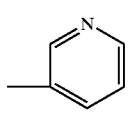 |
| 300930 (Example 8) | CH$_3$— | 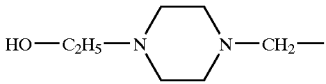 | Cl | 1 | 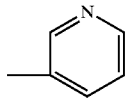 |
| 300934 (Example 9) | CH$_3$— | 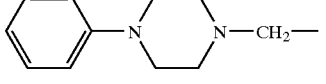 | Cl | 1 | 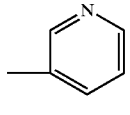 |
| 300939 (Example 10) | CH$_3$— | 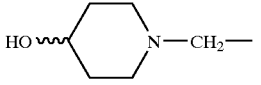 | Cl | 1 | 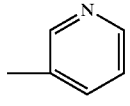 |
| 300929 (Example 11) | CH$_3$— | 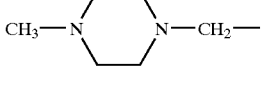 | Cl | 3 | 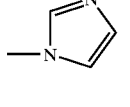 |
| 300942 (Example 12) | CH$_3$— | 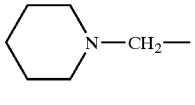 | Cl | 3 | 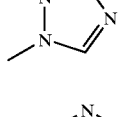 |
| 300941 (Example 13) | (C$_2$H$_5$)$_2$N—CO—CH$_2$— | 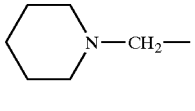 | Cl | 1 | 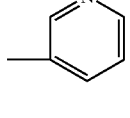 |
| 300938 (Example 14) | 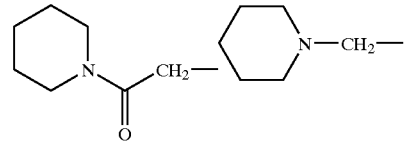 | 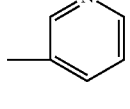 | Cl | 1 | 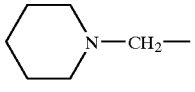 |
| 300931 (Example 15) | CH$_3$O—CH$_2$—C(O)— | 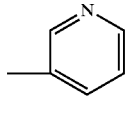 | Cl | 1 | 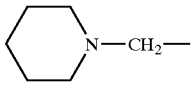 |
| 300933 (Example 16) | (CH$_3$)$_2$—N—C$_2$H$_5$— | 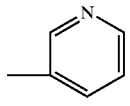 | Cl | 1 | |

TABLE A-continued

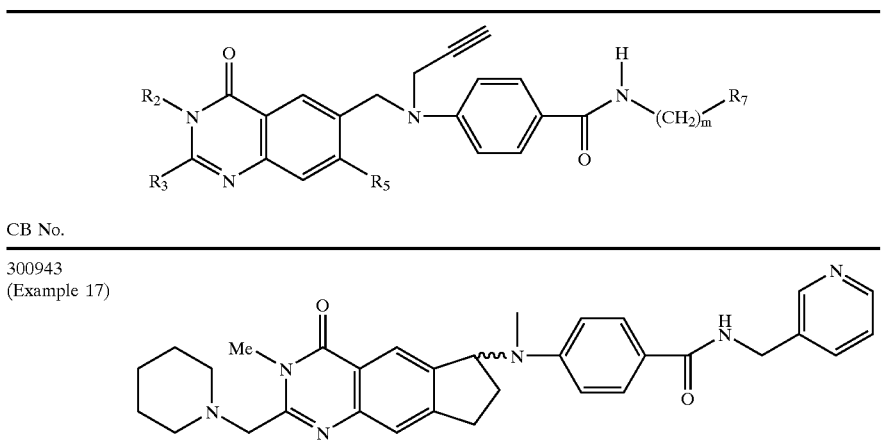

| CB No. | |
|---|---|
| 300943 (Example 17) | |

A Inibition of Thymidylate Synthase

The inhibition of mouse thymidylate synthase (TS) using enzyme partially purified from the L1210:C15 TS-overproducing cell line (Jackman et al, *Cancer Res*, 46, 2810–2815 (1986)) was determined using methods described in Calvert et al. *Advances in Tumour Prevention*, Vol. 5, Harrap & Stathopoulos (eds), pp. 272–283 (1980) and Jackman et al, *Purine Metabolismn in Man IV*, Part B, de Bruyn, Simmonds & Miller (eds), pp 375–378, Plenum Press, (1984).

The $IC_{50}$ against TS, defined as the concentration of drug required to inhibit the reaction rate by 50% at a (R,S)-5,10-$CH_2FH_4$ cofactor concentration of 200 μm, was determined. The results are shown in Table 1.

The results are given in terms of inverse relative potency compared to CB 3717 (N-(4-(N-((2-amino-4-hydroxy-6-quinazolinyl)-methyl)prop-2-ynylanino)benzoyl-L-glutamic acid).

B Growth Inhibition of W1L2 and W1L2:C1 Cell Lines

W1L2 human lymphoblastoid, W1L2:C1 (elevated TS; O'Connor et al, *Cancer Res*, 52, 1137–1143 (1992)) and L1210 mouse leukaemia cells were cultured in suspension and A2780, PXN94, 41M, HX62, SKOV3 (human ovarian carcinoma), MCF-7 (human breast carcinoma), HT29 and SW480 (human colon carcinoma) cell lines were grown as monolayers as described in Jackman et al, *Cancer Res*, 50, 5212–5218 (1990) and Jackman et al, *Br. J. Cancer*, 71, 914–924 (1995).

All cell lines were screened routinely for Mycoplasmyza using the Stratagene PCR method (Stratagene Ltd, Cambridge, UK).

Growth inhibition studies with suspension cells were performed as described in Jackman et al, *Cancer Res*, 50, 5212–5218 (1990). Activity against the adherent cell lines was assessed by MTT assay (Twentyman et al, *Br. J. Cancer*, 56, 279–285 (1987)) where cells were seeded in 96-well plates at 1000–3000 cells per well, incubated overnight and then exposed to the appropriate drug concentrations for 96–120 h.

The results are shown in Table 1. $IC_{50}$ values represent the concentration of drug required to inhibit cell growth/reduce absorbance at 540 mn to 50% control.

C Growth Inhibition of W1L2 in Presence of Folate Metabolites

Growth inhibition assays as described above were performed in W1L2 cells where compounds were incubated in the presence of 10 μM thymidine (dThd) and 50 μM hypoxantine (HX) (purchased from Sigma Chemical Co.).

D Growth Inhibition of $W1L2:R_{865}$ Cell Line

A cell line was raised with acquired resistance to CB 30865, denoted $W1L2:R_{865}$, by stepwise selection over ~9 months. Initially, W1L2 cells were incubated with 0.002 μm CB 30865 (72 h $IC_{50}$ =0.0028 μm), which was raised in small increments (<twofold) until the cells became resistant to 0.03 μm. When larger increments were attempted, the cells did not survive.

The generated $W1L2:R_{865}$ cell line was routinely cultured in 0.03 μm CB 30865 under the same conditions as W1L2 cells, with cells being grown in the absence of CB 30865 for ~2 weeks before an experiment.

The activity of compounds against $W1L2:R_{865}$ cells was determined within parallel experiments by 72 h growth inhibition assay (Coulter counts). CB 30865 was included in every experiment as an internal control.

TABLE 1

| Compound | Example No. | Inhibition of L1210 TS (A) IRP* | Inhibition of Cell Growth ($IC_{50}$ (nml)) | | | |
|---|---|---|---|---|---|---|
| | | | W1L2 (B) | W1L2 + dThd/HX (C) | W1L2:C1 (B) | W1L2:R865 (D) |
| CB300847 | | 382 | 6.5 ± 1.7 | 4.9 6.2 | 2.7 | 2500 |
| CB30865 | | 16 | 2.8 ± 0.5 | 2.2 ± 0.82 | 2.3 ± 0.15 | 610 |
| CB300919 | 1 | >2500 | 0.49 ± 0.24 | 0.32 0.58 | 0.28 | 13000 ± 4500 |

TABLE 1-continued

| Compound | Example No. | Inhibition of L1210 TS (A) IRP** | Inhibition of Cell Growth (IC$_{50}$ (nml)) | | | |
|---|---|---|---|---|---|---|
| | | | W1L2 (B) | W1L2 + dThd/HX (C) | W1L2:C1 (B) | W1L2:R865 (D) |
| CB300921 | 1 | / | 0.65 ± 0.15 | 0.73 ± 0.10 | 0.62 | >10000 |
| | | | | | 0.54 | |
| CB300922 | 2 | >2500 | 7.1 ± 0.076 | 0.73 ± 0.05 | 0.42 | >50000 |
| CB300923 | 3 | >4211 | 0.8 | 0.78 | / | 14000 |
| | | | 0.8 | | | |
| CB300925 | 4 | | 2.0 ± 0.36 | 2.0 | / | 19000 |
| CB300926 | 5 | | 0.70 | 0.76 | / | 24000 |
| | | | 0.74 | 0.70 | | |
| CB300927 | 6 | | 0.78 | 0.78 | / | 22000 |
| | | | 0.80 | 0.76 | | 20000 |
| CB300928 | 7 | | 18 | 14 | / | 24000 |
| | | | 6.6 | 7.6 | | 19000 |
| CB300930 | 8 | / | 0.70 | / | 0.71 | 22000 |
| | | | 1.9 | | 2.0 | 19000 |
| CB300934 | 9 | / | 7.2 | / | 5.4 | 940 |
| CB300939 | 10 | / | 0.72 | / | 0.70 | 18000 |
| CB300929 | 11 | / | 2.1 | / | 2.3 | 18000 |
| | | | 2.2 | | 2.2 | 14000 |
| CB300942 | 12 | / | >500 | / | >500 | 20000 |
| CB300941 | 13 | / | 9.4 | / | 8.4 | 19 |
| CB300938 | 14 | / | 8.4 | / | 7.4 | >50000 |
| CB300931 | 15 | / | 11 | / | 9.6 | 23000 |
| CB300933 | 16 | / | 2.9 | / | 2.8 | 7200 |
| CB300943 | 17 | / | 28 | / | 26 | >500 |

**IRP = inverse relative potency compared to CB3717 in the same experiment (i.e. TS IC$_{50}$ compound/IC$_{50}$ CB 3717). TS IC$_{50}$ values for CB3717 ranged from 0.012–0.032 μm).

The results shown in column (A) show that the compounds of the invention are not good inhibitors of thymidylate synthase (TS).

The results in columns (B) show that the compounds of the invention are active against the human W1L2 lymphoblastoid cell line despite not being good inhibitors of TS. They are active against W1L2 cells and against W1L2:C1 cells, which latter cells are resistant to TS inhibitors.

The results in column (C) show that the compounds of the invention retain activity despite the presence of folate metabolites. This indicates activity at a non-folate dependent locus.

The results in column (D) demonstrate decreased activity against a cell line resistant to CB 30865. This indicates that the compounds of the invention act at the same locus as CB 30865.

EXAMPLE 19

As adopted by the NCI, the hollow fibre assay (Hollingshead et al. 1995, Life Sciences, 57: 13 1–141) was used as an initial means of assessing the in vivo antitumour activity of CB 300919.

Methods

The hollow fibre assay was performed using the CH$_1$ ovarian carcinoma cell line and the HT29 colon line.

Single cell suspensions were prepared and sealed into 2cm length polyvinylidine fluoride (PVDF) fibres (each cell line using a different colour fibre). Three days later (after incubation of fibres in tissue culture medium), fibres were implanted into nude mice using a trochar (3 fibres/cell lines intraperitoneally (ip) and 3 subcutaneously (sc)). There were 3 mice per dose level and 6 controls. One day later (day 1), CB 300919 was administered by ip injection, daily for 3 days (days 1–3). Six days from implantation (day 5), fibres were removed and numbers of viable cells assessed in treated versus control fibres using the colorimetric MT assay.

Results are expressed as a % Treated/Control (T/C).

Results

Against CH$_1$ cells in the fibres, CB 300919 reduced optical density (indirectly a measure of cell number) to <15% at all doses given IP (0.25–0.75 mg/kg/day×3 days). HT29 cells were less sensitive at these doses. This reflects the ~10 fold lower sensitivity of these cells in vitro. In conclusion, antitumour activity was observed at doses of CB 300919 that were tolerated.

Detailed results are shown in Table 2.

TABLE 2

| Cell Line | Dose (daily x 3 days) (mg/kg/d) | Total dose | O.D. as % control | Dose to give 50% inhibition of tumour growth (mg/kg/d) | Weight loss (up to day 5) | Comments |
|---|---|---|---|---|---|---|
| CH1 ovarian | 0.75 | 2.25 | 13% | | 9–22% wt. loss | ⅓ killed (d4; 22% wt. loss |
| | 0.50 | 1.5 | 13% | | 0–19% wt. loss | |
| | 0.25 | 0.75 | 13% | <0.25 | No sig. wt. loss | |

TABLE 2-continued

| Cell Line | Dose (daily x 3 days) (mg/kg/d) | Total dose | O.D. as % control | Dose to give 50% inhibition of tumour growth (mg/kg/d) | Weight loss (up to day 5) | Comments |
|---|---|---|---|---|---|---|
| HT29 colon | 0.75 | 2.25 | 29% |  | As above | As above |
|  | 0.50 | 1.5 | 34% | 0.4 | As above |  |
|  | 0.25 | 0.75 | 92% |  | As above |  |

Mice injected with CB 300919 i.p. on days 1–3. Tumours harvested on day 5.

MTD (dose at which all mice survive) in nude mice ~0.5–0.75 mg/kg/d×3 days.

MTD in DBA2 mice ~1.5 mg/kg/d×3 days.

What is claimed is:

1. A dihydroquinazoline derivative of formula (I), or a pharmaceutically acceptable salt thereof,

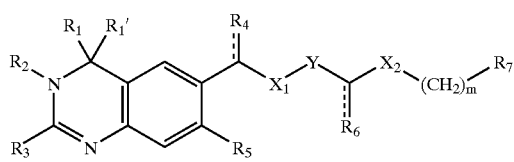

(I)

wherein:
either $R_1$ and $R_1'$ together form an oxo group and $R_2$ is hydrogen, $C_1$–$C_4$ alkyl, —($C_1$–$C_4$ alkyl)—B, —($C_1$–$C_4$ alkyl)—COB, —($C_1$–$C_4$ alkyl)—CO—($C_1$–$C_4$ alkyl)—B, —($C_1$–$C_4$ alkyl)—$CO_2$—($C_1$–$C_4$ alkyl)—B, —($C_1$–$C_4$ alkyl)—$CO_2$—($C_2$–$C_4$ alkenyl)—B or —($C_1$–$C_4$ alkyl)—CONH—($C_1$–$C_4$ alkyl)—B wherein B is —$CO_2$H, hydroxy, $C_1$–$C_4$ alkoxy, amino, ($C_1$–$C_4$ alkyl)amino, di-($C_1$–$C_4$ alkyl) amino or a 5- or 6-membered heterocyclic group, or $R_1'$ and $R_2$ together form a bond and $R_1$ is —S—($C_1$–$C_4$ alkyl), —NHR' or —NHCOR' wherein R' is aryl or $C_1$–$C_4$ alkyl;

$R_3$ is —$(CH_2)_p$—A wherein p is from 1 to 4 and A is a 5- or 6-membered N-containing heterocyclic ring attached via the N atom or A is —NA'A" wherein A' and A" are the same or different and are each a $C_1$–$C_4$ alkyl group;

either $R_4$ is hydrogen, oxo or $C_1$–$C_4$ alkyl and $R_5$ is hydrogen, $C_1$–$C_4$ alkyl or halogen, or $R_4$ and $R_5$, together with the carbon atoms to which they are attached, form a 5- or 6-membered carbocyclic ring, the symbol . . . indicating a double bond to $R_4$ when $R_4$ is oxo and a single bond to $R_4$ when $R_4$ is hydrogen or $C_1$–$C_4$ alkyl or forms a carbocyclic ring with $R_5$;

$X_1$ is —O—, —S— or —NR"— wherein R" is hydrogen, $C_1$–$C_4$ alkyl, $C_2$–$C_4$ alkenyl or $C_2$–$C_4$ alkynyl;

Y is a divalent aryl or heteroaryl group;

$R_6$ is hydrogen, oxo or $C_1$–$C_4$ alkyl, the symbol . . . indicating a double bond to $R_6$ when $R_6$ is oxo and a single bond to $R_6$ when $R_6$ is hydrogen or $C_1$–$C_4$ alkyl;

$X_2$ is —O—, —S— or —NR"— wherein R" is as defined above;

m is from 1 to 4; and $R_7$ is pyridyl, pyrimidyl, imidazolyl, triazolyl, —($C_1$–$C_4$ alkyl)-imidazolyl, or —($C_1$–$C_4$ alkyl)-triazolyl, the aryl moieties in the $R_1$ to $R_7$ substituents being unsubstituted or substituted by 1, 2, 3 or 4 substituents selected from halogen, hydroxyl, $C_1$–$C_4$ alkyl, $C_1$–$C_4$ alkoxy, amino, ($C_1$–$C_4$ alkyl)amino and di-($C_1$–$C_4$ alkyl)amino substituents;

said 5- or 6-membered carbocyclic ring being unsubstituted or substituted by 1 or 2 substituents selected from halogen, hydroxyl, $C_1$–$C_4$ alkyl, $C_1$–$C_4$ alkoxy, amino, ($C_1$–$C_4$ alkyl)amino and di-($C_1$–$C_4$ alkyl)amino substituents;

the said divalent heteroaryl group being unsubstituted or substituted by up to 3 substituents selected from halogen, hydroxyl, $CF_3$, $CCl_3$, $C_1$–$C_4$ alkyl, $C_1$–$C_4$ alkoxy, amino, ($C_1$–$C_4$ alkyl)amino and di-($C_1$–$C_4$ alkyl)amino substituents;

said 5- or 6-membered heterocyclic group being unsubstituted or substituted by 1, 2 or 3 substituents selected from halogen, hydroxyl, $CF_3$, $CCl_3$, $CO_2H$, amino, ($C_1$–$C_4$ alkyl)amino and di-($C_1$–$C_4$ alkyl)amino substituents;

said 5- or 6-membered N-containing heterocyclic ring being unsubstituted or substituted by up to 3 substituents selected from halogen, hydroxyl, $CF_3$, $CCl_3$, $C_1$–$C_4$ alkyl, $C_1$–$C_4$ alkoxy, phenyl, -phenyl-$CO_2H$, -phenyl-$CO_2$—($C_1$–$C_4$ alkyl), amino, ($C_1$–$C_4$ alkyl) amino, di-($C_1$–$C_4$ alkyl)amino, —$CO_2H$, —$CO_2$— ($C_1$–$C_4$ alkyl) and a 5- or 6-membered heterocyclic group; and the alkyl, alkenyl and alkynyl moieties in the $R_1$ to $R_7$ substituents being unsubstituted or substituted with up to 3 substituents selected from hydroxy, halogen, amino, ($C_1$–$C_4$ alkyl)amino and di-($C_1$–$C_4$ alkyl)amino substituents.

2. A compound according to claim 1, wherein:
(a) when $R_1$ and $R_1'$ together form an oxo group, $R_2$ is hydrogen, $C_1$–$C_4$ alkyl, —($C_1$–$C_4$ alkyl)—COB, —($C_1$–$C_4$ alkyl)—CO—($C_1$–$C_4$ alkyl)—B, —($C_1$–$C_4$ alkyl)—$CO_2$—($C_1$–$C_4$ alkyl)—B, —($C_1$–$C_4$ alkyl)—$CO_2$—($C_2$–$C_4$ alkenyl)—B or —($C_1$–$C_4$ alkyl)—CONH—($C_1$–$C_4$ alkyl)—B wherein B is —$CO_2H$, hydroxy, amino, ($C_1$–$C_4$ alkyl)amino, di($C_1$–$C_4$ alkyl) amino or a 5- or 6-membered heterocyclic group; and
(b) $R_7$ is pyridyl, imidazolyl, or —($C_1$–$C_4$ alkyl)-imidazolyl.

3. A compound according to claim 1 or 2, wherein:
the aryl moieties in the $R_1$ to $R_7$ substituents are unsubstituted or substituted by 1, 2, 3 or 4 substituents selected from halogen, hydroxyl, methyl, ethyl, methoxy, ethoxy, amino, ($C_1$–$C_4$ alkyl)amino and di-($C_1$–$C_4$ alkyl)amino substituents;

said 5- or 6-membered carbocyclic ring is unsubstituted or substituted by 1 or 2 substituents selected from halogen, hydroxyl, methyl, ethyl, methoxy, ethoxy, amino, ($C_1$–$C_4$ alkyl)amino, di-($C_1$–$C_4$ alkyl)amino and —($C_1$–$C_4$ alkyl)—OH substituents;

said divalent heteroaryl group is unsubstituted or substituted by 1 or 2 substituents selected from halogen, hydroxyl, CF$_3$, CCl$_3$, methyl, ethyl, methoxy, ethoxy, amino, (C$_1$–C$_4$ alkyl)amino and di-(C$_1$–C$_4$ alkyl)amino substituents;

said 5- or 6-membered heterocyclic group is unsubstituted or substituted by 1, 2 or 3 substituents selected from halogen, hydroxy, CF$_3$, CCl$_3$, —CO$_2$H, amino, (C$_1$–C$_4$ alkyl)amino and di-(C$_1$–C$_4$ alkyl)amino substituents;

said 5- or 6-membered N-containing heterocyclic ring is unsubstituted or substituted by 1 or 2 substituents selected from halogen, hydroxyl, CF$_3$, CCl$_3$, methyl, ethyl, hydroxyethyl, methoxy, ethoxy, phenyl, -phenyl-CO$_2$H, -phenyl-CO$_2$—(C$_1$–C$_4$ alkyl), amino, (C$_1$–C$_4$ alkyl)amino, di-(C$_1$–C$_4$ alkyl)amino, —CO$_2$H, —CO$_2$Me, piperidyl, pyridyl, pyrazinyl, piperazinyl and morpholinyl substituents.

4. A compound according to claim 1, wherein R$_1$ and R$_1$' together form an oxo group or R$_1$' and R$_2$ together form a bond and R$_1$ is —SCH$_3$, —NHCOPh or —NHR' wherein R' is a C$_1$–C$_4$ alkyl group substituted by a di-(C$_1$–C$_4$ alkyl) amino group.

5. A compound according to claim 1, wherein R$_1$ and R$_1$' together form a oxo group and R$_2$ is hydrogen, C$_1$–C$_4$ alkyl, —(C$_1$–C$_4$ alkyl)—CO$_2$H, —(C$_1$–C$_4$ alkyl)—CO$_2$—(C$_1$–C$_4$ alkyl), —(C$_1$–C$_4$ alkyl)—CONR'R" wherein R' and R" are the same or different and are selected from hydrogen and C$_1$–C$_4$ alkyl, —(C$_1$–C$_2$ alkyl)—B, —(C$_1$–C$_2$ alkyl)—CO—(C$_1$–C$_4$ alkyl)—B, —(C$_1$–C$_2$ alkyl)—CO$_2$—(C$_1$–C$_4$ alkyl)—B, —(C$_1$–C$_2$ alkyl)—CONH—(C$_1$–C$_4$ alkyl)—B or —(C$_1$–C$_2$ alkyl)—CO—B' wherein B' is a 5- or 6-membered heterocyclic group.

6. A compound according to claim 5, wherein R$_2$ is hydrogen, C$_1$–C$_4$ alkyl, —(C$_1$–C$_4$ alkyl)—CO$_2$H, —(C$_1$–C$_4$ alkyl)—CO$_2$—(C$_1$–C$_4$ alkyl), —(C$_1$–C$_4$ alkyl)—CONR'R" wherein R' and R" are as defined in claim 5, or —(C$_1$–C$_2$ alkyl)—COB' wherein B' is as defined in claim 5.

7. A compound according to claim 1, in which R$_3$ is —(CH$_2$)$_p$A wherein p is 1 or 2 and A is a piperidyl, piperazinyl, morpholinyl or pyrrolidinyl group which is unsubstituted or substituted by phenyl, hydroxy, methyl, ethyl, hydroxyethyl or —CO$_2$—(C$_1$–C$_4$ alkyl), or A is —NEt$_2$.

8. A compound according to claim 1, wherein R$_5$ is halogen or —CX$_3$ wherein X is a halogen.

9. A compound according to claim 1, wherein —CR$_4$X$_1$— and/or —CR$_6$X$_2$— is —CH$_2$N(CH$_2$CCH)—, —CON(C$_1$–C$_4$ alkyl)—, —CH(C$_1$–C$_4$ alkyl)NH—, —CH(C$_1$–C$_4$ alkyl)N(C$_1$–C$_4$ alkyl)—, —CH$_2$O—, —CH$_2$S— or —CO—NH—.

10. A compound according to claim 1, which is:

4-[N-[7-chloro-3-methyl-2-(4-methyl-piperazin-1-yl)methyl-4-oxo-3,4-dihydroquinazolin-6-ylmethyl]-N-(prop-2-ynyl)amino]-N-(3-pyridylmethyl)benzamide;

4-[N-[2-diethylaminomethyl-7-chloro-3-methyl-4-oxo-3,4-dihydroquinazolin-6-ylmethyl]-N-(prop-2-ynyl)amino-N-(3-pyridylmethyl)benzamide;

4-[N-[7-chloro-3-methyl-4-oxo-2-(piperidin-1-yl)methyl-3,4-dihydroquinazolin-6-ylmethyl]-N-(prop-2-ynyl)amino]-N-(3-pyridylmethyl)benzamide;

4-[N-[7-chloro-3-methyl-2-(morpholin-4-yl)methyl-4-oxo-3,4-dihydroquinazolin-6-ylmethyl]-N-(prop-2-ynyl)amino]-N-(3-pyridylmethyl)benzamide;

4-[N-[7-chloro-3-methyl-2-(pyrrolidin-1-yl)methyl-4-oxo-3,4-dihydroquinazolin-6-ylmethyl]-N-(prop-2-ynyl)amino]-N-(3-pyridylmethyl)benzamide;

4-[N-[7-chloro-3-methyl-2-(4-ethyl-piperazin-1-yl)methyl-4-oxo-3,4-dihydroquinazolin-6-ylmethyl]-N-(prop-2-ynyl)amino]-N-(3-pyridylmethyl)benzamide;

4-[N-[7-chloro-3-methyl-2-(methyl-L-prolin-1-yl)methyl-4-oxo-3,4-dihydroquinazolin-6-ylmethyl]-N-(prop-2-ynyl)amino]-N-(3-pyridylmethyl)benzamide;

4-[N-[7-chloro-3-methyl-2-(4-(2-hydroxyethyl)-piperazin- -yl)methyl-4-oxo-3,4-dihydroquinazolin-6-ylmethyl]-N-(prop-2-ynyl)amino]-N-(3-pyridylmethyl) benzamide, 4-[N-[7-chloro-3-methyl-4-oxo-2-(4-phenylpiperazin- -yl)methyl-3,4-dihydroquinazolin-6-ylmethyl]-N-(prop-2-ynyl)amino]-N-(3-pyridylmethyl)benzamide, 4-[N-[7-chloro-3-methyl-2-(4-hydroxypiperidin-1-yl)methyl-4-oxo-3,4-dihydroquinazolin-6-ylmethyl]-N-(prop-2-ynyl)amino]-N-(3-pyridylmethyl)benzamide, 4-[N-[7-chloro-3-methyl-2-(4-methyl-piperazin-1-yl)methyl-4-oxo-3,4-dihydroquinazolin-6-ylmethyl]-N-(prop-2-ynyl)amino]-N-[3-(1H-imidazol-1-yl)propyl]benzamide, 4-[N-[7-chloro-3-methyl-4-oxo-2-(piperidin-1-yl)methyl-3,4-dihydroquinazolin-6-ylmethyl]-N-(prop-2-ynyl)amino]-N-[(3-(1H-1,2,4-triazol-1-yl)propyl]benzamide, 4-[N-[7-chloro-3-diethylcarbamoylmethyl-4-oxo-2-(piperidin- -yl)methyl-3,4-dihydroquinazolin-6-ylmethyl]-N-(prop-2-ynyl)amino]-N-(3-pyridylmethyl)benzamide, 4-[N-[7-chloro-4-oxo-2-(piperidin-1-yl)methyl-3-piperidinocarbonylmethyl-3,4-hydroquinazolin-6-ylmethyl]-N-(prop-2-ynyl)amino]-N-(3-pyridylmethyl)benzamide, 4-[N-[7-chloro-3-methoxycarbonylmethyl-4-oxo-2-piperidin- -ylmethyl-3,4-dihydroquinazolin-6-ylmethyl]-N-(prop-2-ynyl)amino]-N-(3-pyridylmethyl)benzamide, 4-[N-[7-chloro-3-(2-dimethylaminoethyl)-4-oxo-2-piperidin-1-ylmethyl-3,4-dihydroquinazolin-6-ylmethyl]-N-(prop-2-ynyl)amino]-N-(3-pyridylmethyl)benzamide, 4-[N-[3-methyl-4-oxo-2-(piperidin-1-yl)methyl-3,4,7,8-tetrahydro-6H-cyclopenta[g]quinazolin-6-yl]-N-methylamino]-N-(3-pyridylmethyl)benzamide or a pharmaceutically acceptable salt thereof.

11. A process for preparing a dihydroquinazoline derivative according to claim 1, or a pharmaceutically acceptable salt thereof, which process comprises:

(a) reacting a compound of formula (III)

$$X_2'—(CH_2)_m—R_7 \qquad (III)$$

wherein m and $R_7$ are as defined in claim 1 and $X_2'$ is OH, SH or $NH_2R''$ wherein $R''$ is as defined in claim 1, with a compound of formula (IIa) or (IIb)

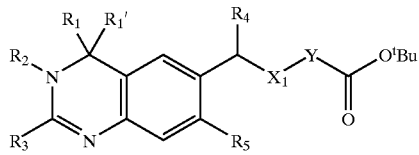

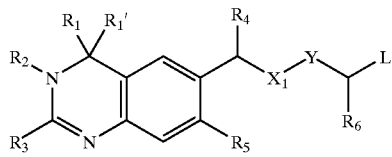

wherein $R_1$, $R_1'$, $R_2$, $R_3$, $R_4$, $R_5$, $X_1$ and Y are as defined in claim 1, $R_6$ is hydrogen or $C_1$–$C_4$ alkyl and L is a leaving group; and (b) optionally salifying the thus obtained compound of formula (I) with a pharmaceutically acceptable acid or base.

12. A pharmaceutical composition comprising a Q dihydroquinazoline derivative according to claim 1, or a pharmaceutically acceptable salt thereof, and a pharmaceutically acceptable carrier or diluent.

13. A method of alleviating breast cancer, liver cancer, cancer of the colon, rectal cancer, stomach cancer, prostate cancer, cancer of the bladder, pancreatic cancer or ovarian cancer in a subject in need of such treatment, which method comprises the administration to the said subject of an effective amount of a dihydroquinazoline derivative according to claim 1, or a pharmaceutically acceptable salt thereof.

* * * * *